(12) United States Patent
Sun

(10) Patent No.: US 10,583,196 B2
(45) Date of Patent: Mar. 10, 2020

(54) POLYMER LINKERS AND THEIR USES

(71) Applicant: NOVACYTE, INC., Needham Heights, MA (US)

(72) Inventor: Binyuan Sun, Needham Heights, MA (US)

(73) Assignee: NOVACYTE, INC., Needham Heights, MA (US)

( * ) Notice: Subject to any disclaimer, the term of this patent is extended or adjusted under 35 U.S.C. 154(b) by 0 days.

(21) Appl. No.: 15/572,720

(22) PCT Filed: Jun. 2, 2017

(86) PCT No.: PCT/US2017/035698
§ 371 (c)(1),
(2) Date: Nov. 8, 2017

(87) PCT Pub. No.: WO2017/210566
PCT Pub. Date: Dec. 7, 2017

(65) Prior Publication Data
US 2019/0083634 A1     Mar. 21, 2019

Related U.S. Application Data

(60) Provisional application No. 62/345,557, filed on Jun. 3, 2016.

(51) Int. Cl.
| | | |
|---|---|---|
| A61K 47/60 | (2017.01) | |
| C08G 65/48 | (2006.01) | |
| C08G 65/00 | (2006.01) | |
| A61K 47/68 | (2017.01) | |
| A61P 35/00 | (2006.01) | |
| A61K 31/4745 | (2006.01) | |
| A61K 47/16 | (2006.01) | |
| A61K 47/22 | (2006.01) | |

(52) U.S. Cl.
CPC .......... *A61K 47/60* (2017.08); *A61K 31/4745* (2013.01); *A61K 47/16* (2013.01); *A61K 47/22* (2013.01); *A61K 47/6855* (2017.08); *A61P 35/00* (2018.01); *C08G 65/00* (2013.01); *C08G 65/48* (2013.01)

(58) Field of Classification Search
None
See application file for complete search history.

(56) References Cited

U.S. PATENT DOCUMENTS

| | | |
|---|---|---|
| 7,790,150 B2 | 9/2010 | Papisov et al. |
| 8,524,214 B2 | 9/2013 | Yurkovetsly et al. |
| 2013/0189218 A1 | 7/2013 | Akullian et al. |

(Continued)

FOREIGN PATENT DOCUMENTS

| | | |
|---|---|---|
| WO | 2013096901 A1 | 6/2013 |
| WO | 2015054669 A1 | 4/2015 |

OTHER PUBLICATIONS

International Search Report and Written Opinion for corresponding PCT/US2017/035698, dated Aug. 29, 2017 (14 pages).

(Continued)

*Primary Examiner* — Karl J Puttlitz
(74) *Attorney, Agent, or Firm* — Melissa Hunter-Ensor; Scott Goncher; Greenberg Traurig, LLP

(57) ABSTRACT

Provided herein are poly-1-hydroxymethylethylene hydroxymethyl formal (PHF)-based drug delivery systems. Also disclosed are methods of making antibody-drug conjugates and methods of treatment using these conjugates.

27 Claims, 3 Drawing Sheets

(56) References Cited

U.S. PATENT DOCUMENTS

2015/0104407 A1    4/2015   Yurkovetskiy et al.
2015/0366982 A1   12/2015   Bodyak et al.
2016/0022829 A1    1/2016   Yurkovetskiy et al.

OTHER PUBLICATIONS

Office Action received in corresponding Korean Application No. 10-2018-7037645, dated Feb. 22, 2019 and English language communication from foreign representative discussing the Office Action (5 pages).

Examination Report No. 1 for corresponding Australian Patent Application No. 2017273871, dated Mar. 8, 2019 (8 pages).

Examination Report No. 2 for corresponding Australian Patent Application No. 2017273871, dated Mar. 12, 2019 (9 pages).

Yurkovetskiy, A.V. et al., "A Polymer-Based Antibody-Vinca Drug Conjugate Platform: Characterization and Preclinical Efficacy," Aug. 2015; Cancer Research, 75(16):3365-3372. (9 pages).

Extended European Search Report dated Nov. 20, 2019, as received in corresponding European Patent Application No. 17807574.3, (8 pages).

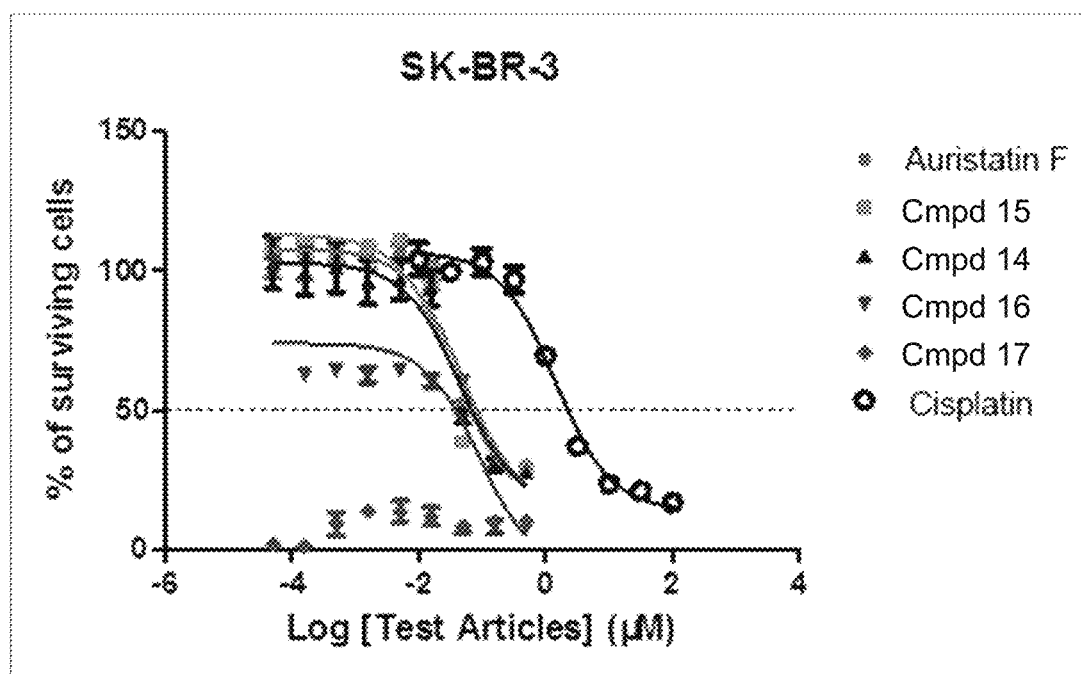
FIG. 4
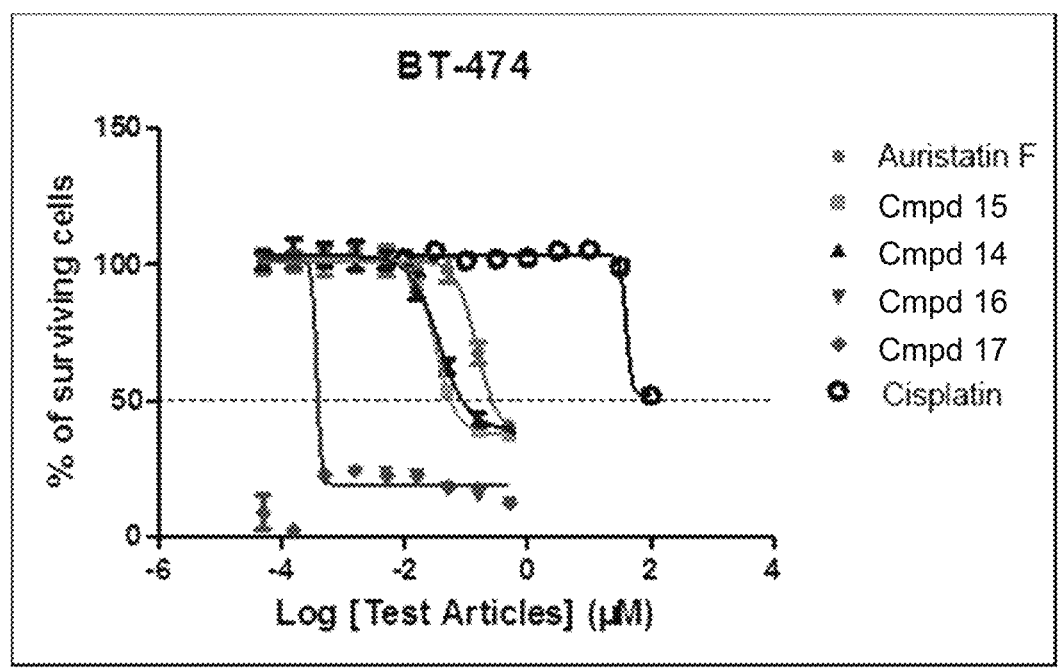

POLYMER LINKERS AND THEIR USES

CROSS-REFERENCE TO RELATED APPLICATION

This application is the U.S. national phase application, pursuant to 35 U.S.C. § 371, of PCT International Application Ser. No.: PCT/US2017/035698, filed Jun. 2, 2017, designating the United States and published in English, which claims priority under 35 U.S.C. § 119(e) to U.S. Provisional Patent Application Ser. No. 62/345,557 filed Jun. 3, 2016, the entire contents of which are hereby incorporated by reference herein.

BACKGROUND

Antibody-drug conjugates are a class of therapeutics that connect an antibody to a drug via a linker. The antibody serves as a drug delivery system to a cell expressing an antigen recognized by the antibody. Linkers such as poly-1-hydroxymethylethylene hydroxymethyl formal ("PHF") have been used in this type of drug delivery system. Highly hydrophilic polyacetal-based PHF polymers can be utilized as a linker to attach multiple hydrophobic drugs to the antibody without affecting the physicochemical properties of the antibody or drug. However, existing PHF-based linkers have significant limitations.

In known PHF-based linkers, drugs or small molecules are attached to the PHF backbone through the acylation of hydroxyl groups on the PHF resulting in ester linkages at the acylation sites. Such PHF-based drugs or small molecules are disclosed in U.S. Pat. No. 8,685,383, hereby incorporated by reference in its entirety. However, these newly formed ester linkage can undergo enzymatic cleavage upon administration to a subject. Additionally, these ester linkages are also cleaved under basic conditions. Moreover, existing PHF-based technology utilizes a second cleavable ester linkage, in addition to the ester linkage of hydroxyl groups on PHF resulting in two enzymatically cleavable sites complicating various mechanistic processes for the compounds. Multiple enzymatically cleavable sites on the linker of antibodydrug conjugates may decrease antitumor activity and increase the risk of toxicity due to premature and nontargeted release of the drug from the antibody. Such premature release may narrow the therapeutic window. Moreover, multiple cleavable sites generally make pharmacokinetics studies more challenging due to more complex kinetic action occurring in linked compounds. Accordingly, delivery of drug payloads with ester linkers can thus be unreliable and difficult to reproduce.

Thus, there is a need in the art to identify non-cleavable linkers that serve as effective antibody-drug conjugates to deliver drugs in a reliable and reproducible manner. The presently disclosed linkers and methods meet this need.

SUMMARY

The drawbacks of PHF-based linkers can be overcome by using a non-cleavable linkage between the drug and the PHF polymer as described herein. When a cleavable linker is needed, an optimizable and cleavable moiety can been introduced in the linkage as required. However, the synthesis of the presently disclosed compounds allows for independent control of the number and type of cleavable linkers between the targeting moiety and the polymer backbone. Additionally, the control of the number and type of cleavable linkers between the therapeutic agent and the polymer backbone is also possible. Such control mitigates several complications associated with known PHF antibody drug conjugates.

PHF has a high solubility in water, but very limited solubility in non-polar organic solvents. PHF is a polyol, so selective chemical transformations of hydroxyl groups on PHF and purifications are challenging. Moreover, PHF contains pH-sensitive acetal groups, and is degradable in acidic conditions. Therefore, selective, mild and clean chemistry is typically required for introducing a non-cleavable linkage to PHF. Also provided herein are methods for synthesizing PHF compounds capable of producing the antibody-drug conjugates. In some embodiments, the synthesis of the compounds described herein comprises:

(a) reacting PHF with an electrophilic reagent to form a polymer comprising an activating group capable of displacement by a thiol;

(b) displacing said activating group by a thiol comprising a linkage capable of covalently bonding (or undergoing a reaction to covalently bond) to a drug or a small molecule.

In some embodiments, the synthesis comprises the synthetic steps shown in Example 1. In some embodiments, the synthesis further comprises the step of converting a portion of the monomer units comprising said linkage into a second linkage capable of covalently bonding (or undergoing a reaction to covalently bond) to a targeting moiety. In some embodiments, the synthesis comprises the synthetic steps shown in Example 6 or Example 7.

The PHF conjugates described herein, which may be produced by any of the described synthetic methods comprise block repeat block monomer units (a) and/or (b) and/or (c) and/or (d)

(I)

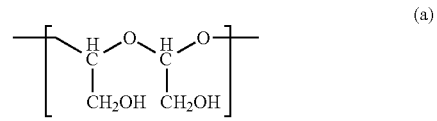
(a)

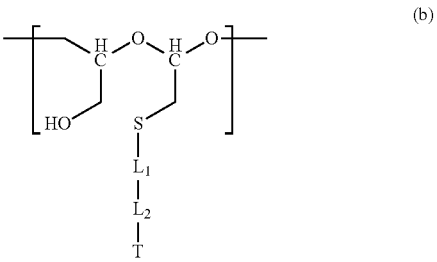
(b)

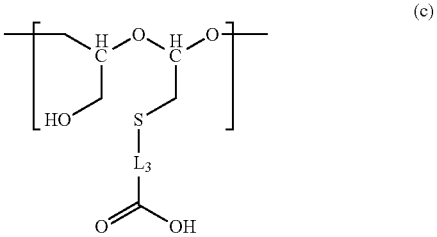
(c)

-continued

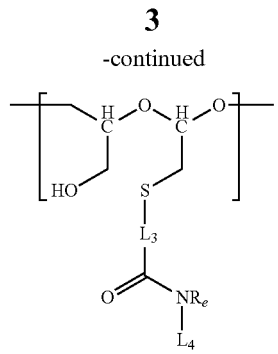

(d)

L$_1$ is a linking group selected from alkylene, heteroalkylene, cycloalkylene, heterocyclylene, arylene, heteroarylene, amidoalkylene, amidoheteroalkylene, and any combination thereof;

L$_2$ is absent, or can be of the formula:

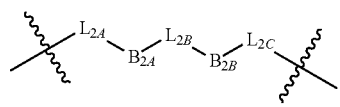

L$_{2A}$ is a linking group selected from alkylene, heteroalkylene, cycloalkylene, heterocyclylene, arylene, heteroarylene, —C(O)—, —N(R$_C$)—, and any combination thereof;

L$_{2B}$ and L$_{2C}$ are independently absent or a linker group selected from alkylene, heteroalkylene, cycloalkylene, heterocyclylene, arylene, heteroarylene, amidoalkylene, amidoheteroalkylene, —C(O)—, —N(R$_C$)—, and any combination thereof;

B$_{2A}$ and B$_{2B}$ are independently absent or a cleavable linker;

T is a therapeutic agent selected from the group consisting of chemotherapeutic agents, microtubule inhibitors, DNA-damaging agents and RNA transcription inhibitors;

L$_3$ is a linker group selected from alkylene, heteroalkylene, cycloalkylene, heterocyclylene, arylene, heteroarylene, amidoalkylene, amidoheteroalkylene, and any combination thereof;

R$_e$ is a substituent selected from hydrogen, alkyl and heteroalkyl;

L$_4$ is a group of the formula:

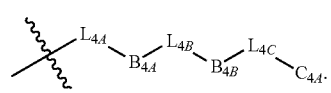

L$_{4A}$ is a linker group selected from alkylene, heteroalkylene, cycloalkylene, heterocyclylene, arylene, heteroarylene, —C(O)—, —N(R$_C$)—, and any combination thereof;

L$_{4B}$ and L$_{4C}$ are independently absent or a linker group selected from alkylene, heteroalkylene, cycloalkylene, heterocyclylene, arylene, heteroarylene, amidoalkylene, amidoheteroalkylene, —C(O)—, —N(R$_C$)—, and any combination thereof;

B$_{4A}$ and B$_{4B}$ are independently absent or a cleavable linker;

C$_{4A}$ is a group selected from

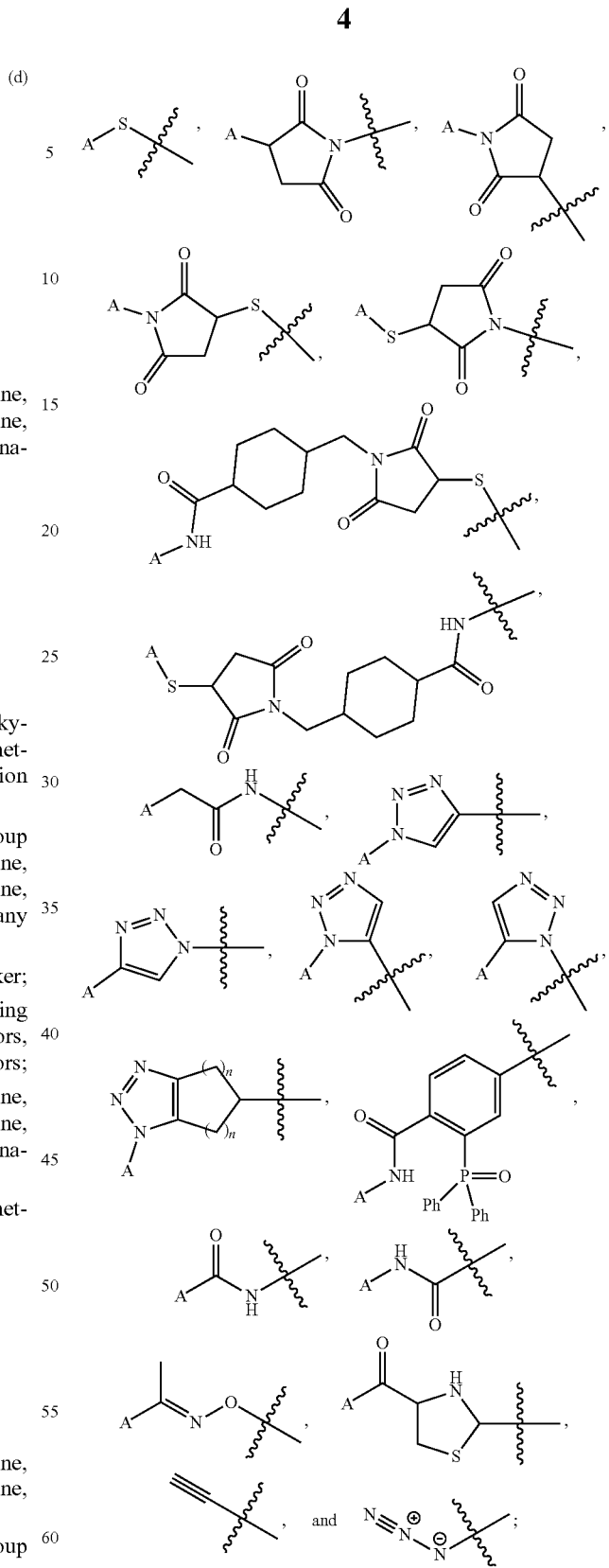

where

A is —H or a targeting moiety selected from the group consisting of an antibody, a synthetically functionalized antibody, a peptide and a targeting ligand;

"n" is independently at each occurrence an integer ranging from 0-5;

$R_c$ and $R_d$ are independently selected at each occurrence from hydrogen, alkyl, heteroalkyl, cycloalkyl, and heterocyclyl;

where each monomer is substituted independently from any additional monomer;

with the proviso that the compound of Formula (I) contains one or more therapeutic agents, T, and one or more targeting moieties A. In some embodiments, the PHF compounds comprise blocks of polymerized monomers (a), (b), (d) and optionally (c):

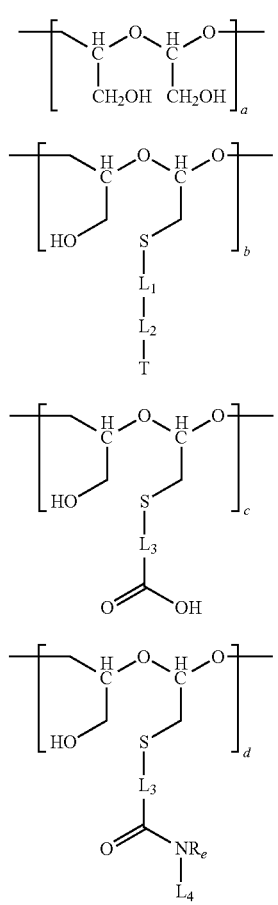

wherein "a" is independently at each occurrence an integer from 1 to about 3000 (e.g., about 1-about 2000, etc.);

"b" is independently at each occurrence an integer from 1 to about 500;

"c" is absent or independently at each occurrence an integer from 1 to about 500;

"d" is independently at each occurrence an integer from 1 to about 200; and each block of monomer unit (a), (b), (c), and (d), is covalently attached to at least one block monomer unit (a), (b), (c), and/or (d) and each block of monomer units is independently substituted from any other block of monomer units. Exemplary cleavable linkers (e.g., biodegradable linkers, etc.) for $B_{2A}$, $B_{2B}$, $B_{4A}$ and $B_{4B}$ may include —S—S—, —C(=O)O—, —OC(=O)—, —C(=O)NR$_c$—, —N(R$_c$)C(=O)—, —OC(=O)O—, —NR$_c$C(=O)O—, —OC(=O)N(R$_c$)— or —N(R$_c$)C(=O)N(R$_d$)—, —C(=O)N(R$_c$)C(=O)—, —C(=O)S—, —SC(=O)—, —SC(=O)S—, —OC(=O)S—, —SC(=O)O—, —OC(=S)O—, —SC(=S)S—, —N(R$_c$)SO$_2$—, —SO$_2$N(R$_c$)—, —N(R$_c$)SO$_2$N(R$_d$)—, —C(=O)N(R$_c$)N(R$_d$)—, —N(R$_c$)N(R$_d$)C(=O)—, —N(R$_c$)N(R$_d$)C(=O)O—, —OC(=O)N(R$_c$)N(R$_d$)—, —C(R$_c$)=N—NH—C(=O)—, —C(=O)NH—N=C(R$_c$), —C(R$_c$)=N—O—, —O—N=C(R$_c$)—,

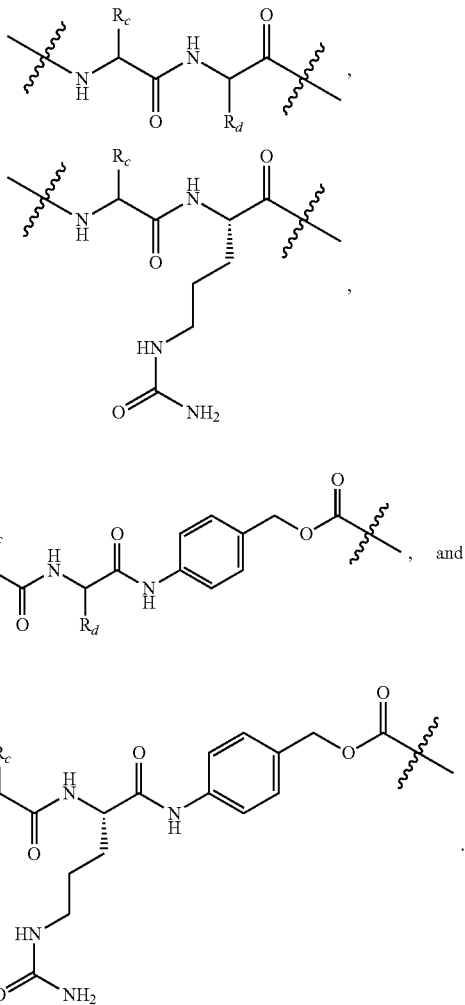

Typically, $L_{2A}$, $L_{2B}$, $L_{2C}$, and combinations thereof (i.e., when $B_{2A}$ and/or $B_{2B}$ are absent) are non-biodegradable linker moieties. Similarly, $L_{4A}$, $L_{4B}$, and $L_{4C}$ and combinations thereof (i.e., when $L_{4A}$ and/or $L_{4B}$ are absent) may be non-biodegradable linker moieties. In some embodiments, $L_2$ does not comprise a cleavable linker.

The compounds may also have the repeat block monomer units (a), (b), and (e)

(II)

(a)

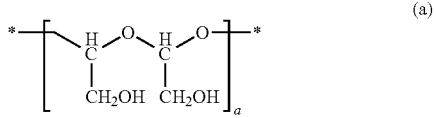

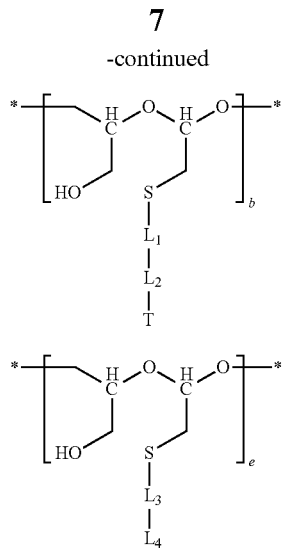

L₁ is a linking group selected from alkylene, heteroalkylene, cycloalkylene, heterocyclylene, arylene, heteroarylene, amidoalkylene, amidoheteroalkylene, and any combination thereof;

L₂ is absent, or can be of the formula:

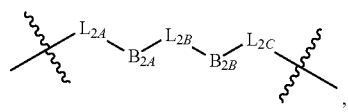

$L_{2A}$ is a linking group selected from alkylene, heteroalkylene, cycloalkylene, heterocyclylene, arylene, heteroarylene, and any combination thereof;

$L_{2B}$ and $L_{2C}$ are independently absent or a linker group selected from alkylene, heteroalkylene, cycloalkylene, heterocyclylene, arylene, heteroarylene, amidoalkylene, amidoheteroalkylene, and any combination thereof;

$B_{2A}$ and $B_{2B}$ are independently absent or a cleavable linker;

T is a therapeutic agent selected from the group consisting of chemotherapeutic agents, microtubule inhibitors, DNA-damaging agents and RNA transcription inhibitors;

L₃ is a linker group selected from alkylene, heteroalkylene, cycloalkylene, heterocyclylene, arylene, heteroarylene, amidoalkylene, amidoheteroalkylene, and any combination thereof;

L₄ is a group of the formula:

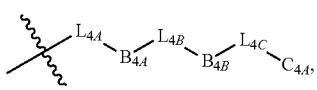

$L_{4A}$ is a linker group selected from alkylene, heteroalkylene, cycloalkylene, heterocyclylene, arylene, heteroarylene, and any combination thereof;

$L_{4B}$ and $L_{4C}$ are independently absent or a linker group selected from selected from alkylene, heteroalkylene, cycloalkylene, heterocyclylene, arylene, heteroarylene, amidoalkylene, amidoheteroalkylene and any combination thereof;

$B_{4A}$ and $B_{4B}$ are independently absent or a cleavable linker $C_{4A}$ is a group selected from

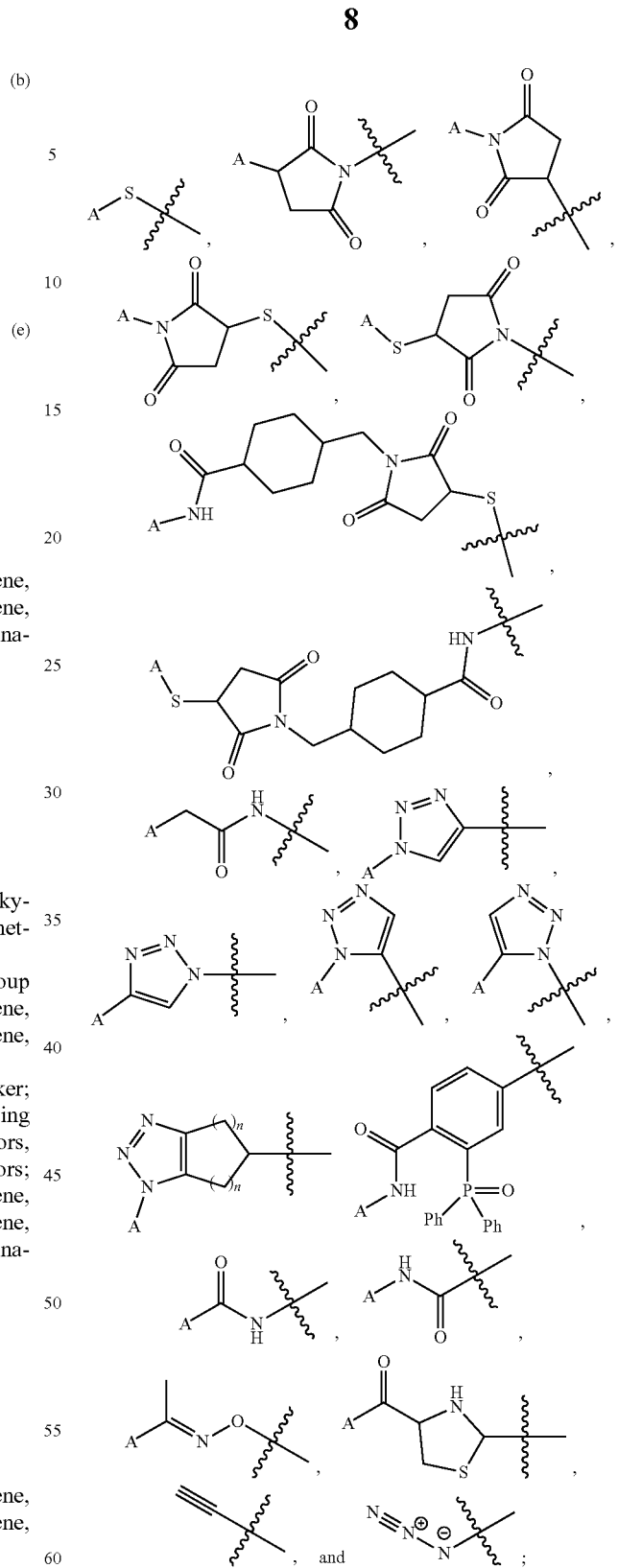

A is —H or a targeting moiety selected from the group consisting of an antibody, a synthetically functionalized antibody, a peptide and a targeting ligand;

"n" is independently at each occurrence an integer ranging from 0-5;

R$_c$ and R$_d$ are independently selected at each occurrence from hydrogen, alkyl, heteroalkyl, cycloalkyl, and heterocyclyl;

where each monomer is substituted independently from any additional monomer;

with the proviso that the compound of Formula (II) contains one or more therapeutic agent and one or more targeting moiety. In some embodiments, the compound may comprise blocks of polymerized monomers (a), (b), and (e):

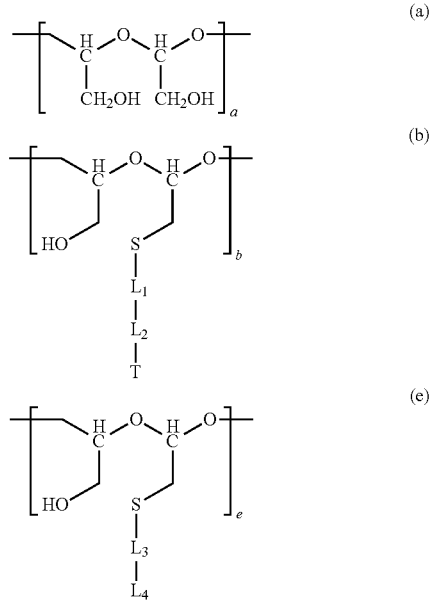

wherein "a" is independently at each occurrence an integer from 1-1860;

"b" is independently at each occurrence an integer from 1-372;

"e" is independently at each occurrence an integer from 1-186; and each block of monomer unit (a), (b), and (e), is covalently attached to at least one block monomer unit (a), (b), and/or (e); and each block of monomer units is independently substituted from any other block of monomer units. Typically, L$_{2A}$, L$_{2B}$, L$_{2C}$, and combinations thereof (i.e., when B$_{2A}$ and/or B$_{2B}$ are absent) are non-biodegradable linker moieties. Similarly, L$_{4A}$, L$_{4B}$, and L$_{4C}$ and combinations thereof (i.e., when L$_{4A}$ and/or L$_{4B}$ are absent) may be non-biodegradable linker moieties. In some embodiments, L$_2$ does not comprise a cleavable linker.

Pharmaceutical compositions are also described comprising any of the compounds or pharmaceutically acceptable salts or solvates thereof. The pharmaceutical compositions may be used in a method of inhibiting cancer cells comprising contacting the cancer cells with a pharmaceutical composition comprising an effective amount of one or more compounds. The pharmaceutical composition may also be used in a method for treating or inhibiting cancer in a patient comprising contacting cancer cells with an anti-cancer effective amount of a pharmaceutical composition comprising the compounds. In some embodiments, the treatment may comprise administering an effective amount of the pharmaceutical composition to a patient in need thereof.

BRIEF DESCRIPTION OF THE DRAWINGS

The following detailed description of exemplary embodiments can be better understood when read in conjunction with the appended drawings. It should be understood, however, that the disclosure is not limited to the precise arrangements and instrumentalities of the embodiments shown in the drawings.

FIG. 3 depicts a dose response curve of the % surviving SKBR3 cells treated with Auristatin F, Compounds 14-17 and Cisplatin.

FIG. 4 depicts a dose response curve of the % surviving BT-474 cells treated with Auristatin F, Compounds 14-17 and Cisplatin.

DETAILED DESCRIPTION

Definitions

Figure 1:
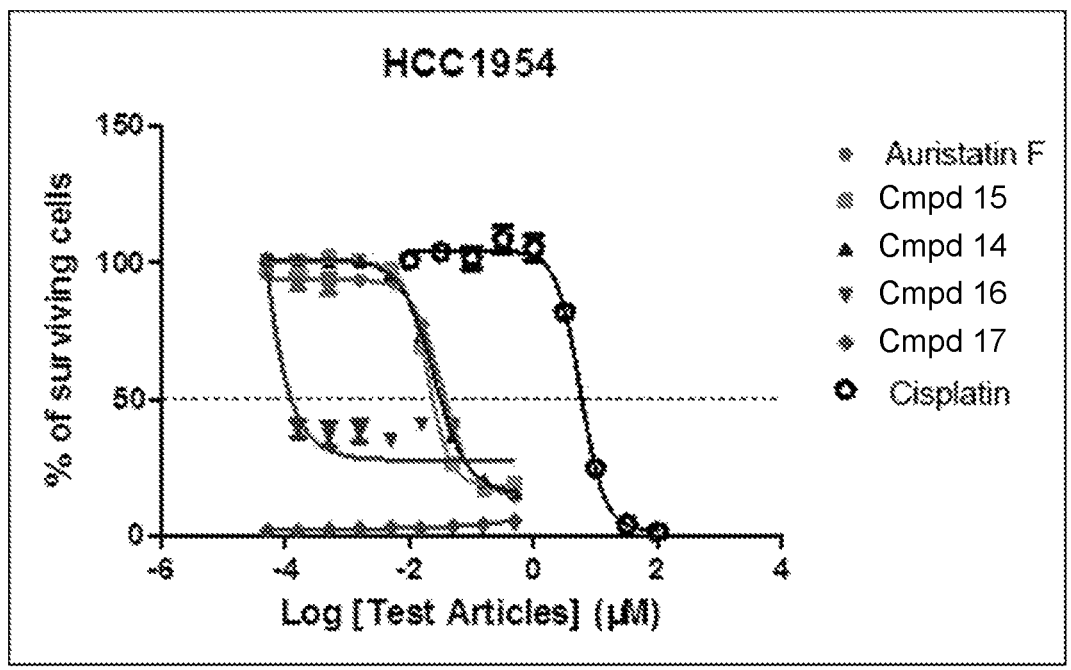
FIG. 1 depicts a dose response curve of the % surviving HCC 1954 cells treated with Auristatin F, Compounds 14-17 and Cisplatin.

Unless defined otherwise, all technical and scientific terms used herein generally have the same meaning as commonly understood by one of ordinary skill in the art to which this disclosure pertains. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). Generally, the nomenclature used herein and the laboratory procedures in medicine, organic chemistry and polymer chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, such as ±5%, such as ±1%, and such as ±0.1% from the specified value, as such variations are appropriate to perform the disclosed methods.

As used herein, the term "alkyl", by itself or as part of another substituent means, unless otherwise stated, a branched or unbranched saturated hydrocarbon group. The term "n-alkyl" refers to an unbranched alkyl group. The term "C$_x$-C$_y$ alkyl" refers to an alkyl group having between x and y carbon atoms, inclusively, in the branched or unbranched hydrocarbon group. By way of illustration, but without limitation, the term "C$_1$-C$_8$ alkyl" refers to a straight chain or branched hydrocarbon moiety having from 1, 2, 3, 4, 5, 6, 7, or 8 carbon atoms. "C$_1$-C$_6$" refers to a straight chain or branched hydrocarbon moiety having from 1, 2, 3, 4, 5, or 6 carbon atoms. "C$_1$-C$_4$ alkyl" refers to a straight chain or branched hydrocarbon moiety having from 1, 2, 3, or 4 carbon atoms, including methyl, ethyl, n-propyl, iso-propyl, n-butyl, iso-butyl, sec-butyl, and tert-butyl. The term "C$_1$-C$_4$ n-alkyl" refers to straight chain hydrocarbon moieties that have 1, 2, 3, or 4 carbon atoms including methyl, ethyl, n-propyl, and n-butyl. An "alkylene" is an alkyl substituent which is covalently bound to two substituents or a single substituent twice.

As used herein, the term "aromatic" refers to a carbocycle or heterocycle with one or more polyunsaturated rings and having aromatic character, i.e. having (4n+2) delocalized π(pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl. An "arylene" is an aryl substituent which is covalently bound to two substituents or a single substituent twice.

As used herein, the term "heteroalkyl", by itself or as part of another substituent means, unless otherwise stated, a branched or unbranched alkyl group in which one or more carbon atoms in the main chain have been substituted with heteroatoms. The heteroatoms include, but not limited to, oxygen, sulfur, silicon, phosphorus, nitrogen atoms, or a combination thereof. A "heteroalkylene" is a heteroalkyl substituent which is covalently bound to two substituents or a single substituent twice.

As used herein, the term "amidoalkyl" refers to an alkyl group that has a —C(O)NR$_a$— or —NR$_a$C(O)— group at either terminus of the alkyl group or within the alkyl group. For example, R$_a$ is selected from H, alkyl and heteroalkyl. An "amidoalkylene" is an amidoalkyl substituent which is covalently bound to two substituents or a single substituent twice.

As used herein, the term "amidoheteroalkyl" refers to an heteroalkyl group that has a C(O)NR$_a$— or —NR$_a$C(O)— group at either terminus of the heteroalkyl group or within the chain of the heteroalkyl group. For example, R$_a$ is selected from H, alkyl and heteroalkyl. An "amidoheteroalkylene" is an amidoheteroalkyl substituent which is covalently bound to two substituents or a single substituent twice.

As used herein, the term "alkoxy" by itself or as part of another substituent means, unless otherwise stated, an —O-alkyl group, including from 1 to 10 carbon atoms of a straight, branched, saturated cyclic configuration and combinations thereof, attached to the parent molecular structure through an oxygen. Examples include methoxy, ethoxy, propoxy, isopropoxy, butoxy, t-butoxy, pentoxy, cyclopropyloxy, cyclohexyloxy and the like. In some embodiments, an alkoxy group can have one to six carbons denoted C$_1$-C$_3$. In some embodiments, C$_{1-4}$ alkoxy is an alkoxy group which encompasses both straight and branched chain alkyls of from 1 to 4 carbon atoms. In some aspects, the alkoxy group is a (C$_1$-C$_3$)alkoxy, such as, but not limited to, ethoxy and methoxy.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl. A "heterocyclylene" is a heterocyclyl substituent which is covalently bound to two substituents or a single substituent twice.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl. A "heteroarylene" is a heteroaryl substituent which is covalently bound to two substituents or a single substituent twice.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "δ" with reference to nuclear magnetic resonance results refers to the measaured chemical shifts for measured nucleii. Unless otherwise specified, δ is in units of ppm.

As used herein, the term "DMSO" refers to dimethylsulfoxide.

As used herein, the term "halo" or "halogen" employed alone or as part of another substituent means, unless otherwise stated, a fluorine, chlorine, bromine, or iodine atom, such as fluorine, chlorine, or bromine, further such as, fluorine or chlorine.

As used herein, "hydroxyl" refers to —OH.

As used herein, the term "reaction condition" refers to a physical treatment, chemical reagent, or combination thereof, which is required or optionally required to promote a reaction. Non-limiting examples of reaction conditions are electromagnetic radiation, heat, a catalyst, a chemical reagent (such as, but not limited to, an acid, base, electrophile or nucleophile), and a buffer.

As used herein, the term "salt" refers to a salt of a compound contemplated herein, including inorganic acids, organic acids, inorganic bases, organic bases, solvates, hydrates, or clathrates thereof. As used herein, the term "salt" embraces addition salts of free acids or free bases that are compounds useful in the methods described herein. In some cases, undesired salts may nonetheless possess properties such as high crystallinity, which may have utility in the practice of the methods described herein, such as, for example, utility in process of synthesis or purification of compounds described herein.

Suitable acid addition salts may be prepared from an inorganic acid or an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxy-ethanesulfonic, p-toluenesulfonic, sulfanilic, cyclohexylaminosulfonic, stearic, alginic, β-hydroxybutyric, salicylic, galactaric and galacturonic acid. Suitable base addition salts of disclosed compounds include, for example, metallic salts including alkali metal, alkaline earth metal and transition metal salts such as, for example, lithium, calcium, magnesium, potassium, ammonium, sodium and zinc salts. Acceptable base addition salts also include organic salts made from basic amines such as, for example, N,N'-dibenzyl-ethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

As used herein, the term "substituted" means that an atom or group of atoms has replaced hydrogen as the substituent attached to another group. Unless stated otherwise, any group recited herein may be substituted.

For aryl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_1$-$C_6$ alkyl, —OH, $C_1$-$C_6$ alkoxy, halo, amino, acetamido and nitro. As used herein, where a substituent is an alkyl or alkoxy group, the carbon chain may be branched, straight or cyclic, such as straight.

As used herein, the term "targeting moiety" is a chemical moiety able to bind to a biological entity. The term targeting moiety may refer to a chemical species such as an antibody, an enzyme, a protein or peptide or any other biological binding ligand.

The term "effective amount" or "therapeutically effective amount" of an agent, as used herein, is that amount sufficient to effect beneficial or desired results, such as clinical results, and, as such, an "effective amount" depends upon the context in which it is being applied. For example, in the context of administering an agent that is an anticancer agent, an effective amount of an agent is, for example, an amount sufficient to achieve alleviation or amelioration or prevention or prophylaxis of one or more symptoms or conditions; diminishment of the extent of cancer, disorder, or condition; stabilized (i.e., not worsening) state of cancer, disorder, or condition; preventing spread of cancer, disorder, or condition; delay or slowing the progress of the disease, disorder, or condition; amelioration or palliation of the disease, disorder, or condition; and remission (whether partial or total), whether detectable or undetectable, as compared to the response obtained without administration of the agent.

The term "pharmaceutical composition," as used herein, represents a composition containing a compound described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein (see below).

Useful pharmaceutical carriers for the preparation of the compositions hereof, can be solids, liquids, or gases. Thus, the compositions can take the form of tablets, pills, capsules, suppositories, powders, enterically coated or other protected formulations (e.g., binding on ion-exchange resins or packaging in lipid-protein vesicles), sustained release formulations, solutions, suspensions, elixirs, and aerosols. The carrier can be selected from the various oils including those of petroleum, animal, vegetable or synthetic origin, e.g., peanut oil, soybean oil, mineral oil, and sesame oil. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, and ethanol. The compositions may be subjected to conventional pharmaceutical additives such as preservatives, stabilizing agents, wetting or emulsifying agents, salts for adjusting osmotic pressure, and buffers. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for administration to the recipient.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc., and to give compounds which are not inherently unstable. For example, any carbon atom will be bonded to two, three, or four other atoms, consistent with the four valence electrons of carbon.

Throughout this disclosure, various aspects of the disclosure may be presented in a range format. It should be understood that the description in range format is merely for convenience and brevity and should not be construed as an inflexible limitation on the scope of the present claims. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6, and so forth, as well as individual numbers within that range, for example, 1, 2, 2.7, 3, 4, 5, 5.3, and 6. This applies regardless of the breadth of the range.

Compounds and Compositions

Provided herein are drug delivery systems that include an antibody-drug conjugate formed from a polymer backbone, a first linker connected to an antibody and a second linker connected to a therapeutic agent or small molecule. In one embodiment, the polymer is a poly-1-hydroxymethylethylene hydroxymethyl formal (PHF)-based polymer. In some embodiments, the first linker includes a sulfide (—S—) bonded to the polymer which is covalently attached to a targeting moiety, such as an antibody. In some embodiments, the second linker includes a sulfide (—S—) bonded to the polymer which is attached to a therapeutic agent. In other embodiments, the second linker is attached to a protein. The protein may comprise cysteine and/or lysine. In some embodiments, cysteine and/or lysine may be the point of conjugation to the protein.

In certain embodiments, the polymer of the invention is a polyacetal, e.g., a poly-1-hydroxymethylethylene hydroxymethyl formal (PHF). In other embodiments, the polyacetal has a molecular weight ranging from about 10 kDa to 250 kDa.

In certain embodiments, the targeting moieties are selected from the group consisting of antibodies, synthetically functionalized antibodies, peptides and other targeting ligands. Examples of targeting antibodies can include, but are not limited to, monoclonal antibodies that are specific for antigens which are overexpressed in cancer cells, antigens regulated from driver oncogenes, antigens in tumor stroma and vasculature or antigens found in haematological malignancies. In certain embodiments, the targeting moieties can include, but are not limited to, HER-2, EGFR, GPNMB, CD56, TACSTD2 (TROP2), CEACAM5, folate receptor-a, mesothelin, ENPP3, guanylyl cyclase C, SLC44A4, NaPi2b, CD70, mucin 1, STEAP1, nectin 4, 5T4, SLTRK6, SC-16, LIV-1, P-Cadherin, PSMA, Fibronectin Extra-domain B, Endothelin receptor ETB, Tenascin c, Collagen IV, VEGFR2, Periostin, CD30, CD79b, CD19, CD22, CD138, CD37, CD33, CD74, CD19 and CD98. In certain embodiments, the targeting moiety is selected from trastuzumab and pertuzumab.

Without being limited to any one theory, the targeting moiety can allow the therapeutic agents or small molecules to be localized at a particular targeting site, for example, a tumor or a tissue. This can effectively increase the efficacy of therapeutic agents at the targeting site, while minimizing unwanted side-effects on normal cells.

In certain embodiments, the therapeutic agent is a chemotherapeutic agent (e.g., a quinolone alkaloid such as camptothecin, etc.). In some embodiments, the therapeutic agent (e.g., chemotherapeutic agent) can include, but is not limited to, microtubule inhibitors, DNA-damaging agents, and RNA transcription inhibitors, and any combinations thereof. In yet other embodiments, the microtubule inhibitors can be one or more selected from, but not limited to, the group consisting of, auristatin, maytansinoid, taxol derivative, vinca alkaloid and any derivatives thereof. In yet other embodiments, the DNA-damaging agents can be one or more selected from, but not limited to, the group consisting of a calicheamicin, a duocarmycin, a doxorubicin, a CC-1065 analog, a methotrexate, a pyrrolobenzodiazepine (PBD) and any derivatives thereof. In yet other embodiments, the RNA transcription inhibitor can be an amanitin, including α-amanitin, β-amanitin, γ-amanatin and ε-amanatin and any derivatives thereof. The therapeutic agent may be tublysin, kinase inhibitor, MEK inhibitor, KSP inhibitor or any combination thereof.

The invention provides an antibody-drug conjugate of Formula (I) as shown below, comprising hydroxy monomeric blocks (a) and/or (b) and/or (c) and/or (d).

(I)

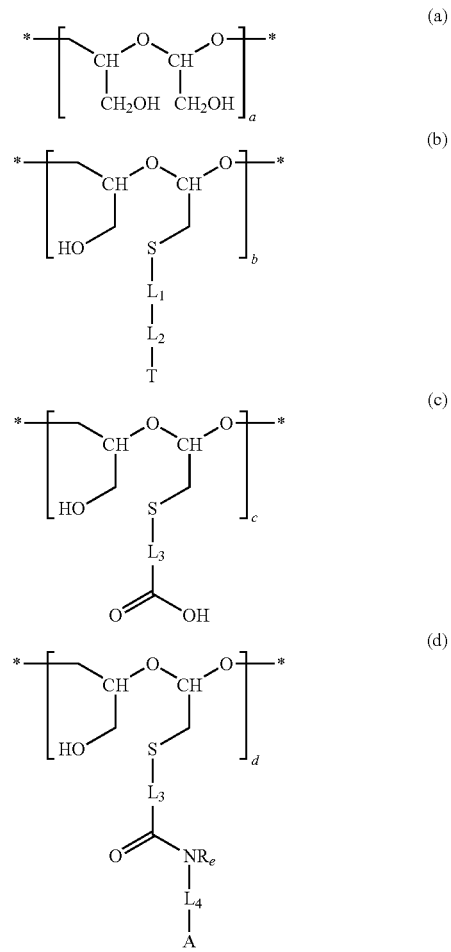

"*" indicates a covalent bond to an additional section of free hydroxy monomer of a formula selected from the group consisting of (a), (b), (c) and (d) wherein each monomer is substituted independently from any additional monomer;

$L_1$ is a linking group selected from alkylene, heteroalkylene, cycloalkylene, heterocyclylene, arylene, heteroarylene, amidoalkylene, amidoheteroalkylene, and any combination thereof;

$L_2$ is absent, or can be of the formula:

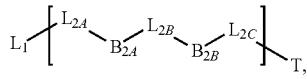

wherein:

$L_{2A}$ is a linking group selected from alkylene, heteroalkylene, cycloalkylene, heterocyclylene, arylene, heteroarylene, and any combination thereof;

$B_{2A}$ is absent or a cleavable linker selected from —S—S—, —C(=O)O—, —OC(=O)—, —C(=O)NR$_c$—, —NR$_c$C(=O)—, —OC(=O)O—, —NR$_c$C(=O)O—, —OC(=O)NR$_c$— or —NR$_c$C(=O)NR$_d$—, —C(=O) NR$_c$C(=O)—, —C(=O)S—, —SC(=O)—, —SC(=O) S—, —OC(=O)S—, —SC(=O)O—, —OC(=S)O—, —SC(=S)S—, —NR$_c$SO$_2$—, —SO$_2$NR$_c$—, —NR$_c$SO$_2$NR$_d$—, —C(=O)NR$_c$NR$_d$—, —NR$_c$NR$_d$C (=O)—, —NR$_c$NR$_d$C(=O)O—, —OC(=O)NR$_c$NR$_d$—, —CR$_c$=N—NH—C(=O)—, —C(=O)NH—N=CR$_c$—, —CR$_c$=N—O—, and —O—N=CR$_c$—, wherein R$_c$ and R$_d$ are each a substituent independently selected from hydrogen, alkyl, heteroalkyl, cycloalkyl, and heterocyclyl;

$L_{2B}$ can be absent or a linker group selected from alkylene, heteroalkylene, cycloalkylene, heterocyclylene, arylene, heteroarylene, amidoalkylene, amidoheteroalkylene, and any combination thereof;

$B_{2B}$ can be absent or a cleavable linker selected from —S—S—, —C(=O)O—, —OC(=O)—, —C(=O) NR$_c$—, —NR$_c$C(=O)—, —OC(=O)O—, —NR$_c$C(=O) O—, —OC(=O)NR$_c$— or —NR$_c$C(=O)NR$_d$—, —C(=O) NR$_c$C(=O)—, —C(=O)S—, —SC(=O)—, —SC(=O) S—, —OC(=O)S—, —SC(=O)O—, —OC(=S)O—, —SC(=S)S—, —NR$_c$SO$_2$—, —SO$_2$NR$_c$—, —NR$_c$SO$_2$NR$_d$—, —C(=O)NR$_c$NR$_d$—, —NR$_c$NR$_d$C (=O)—, —NR$_c$NR$_d$C(=O)O—, —OC(=O)NR$_c$NR$_d$—, —CR$_c$=N—NH—C(=O)—, —C(=O)NH—N=CR$_c$—, —CR$_c$=N—O—, and —O—N=CR$_c$—, wherein R$_c$ and R$_d$ are each a substituent independently selected from hydrogen, alkyl, heteroalkyl, cycloalkyl, and heterocyclyl;

$L_{2C}$ is absent or a linker group selected from alkylene, heteroalkylene, cycloalkylene, heterocyclylene, arylene, heteroarylene, amidoalkylene, amidoheteroalkylene, and any combination thereof;

T is a therapeutic agent;

$L_3$ is a linker group selected from alkylene, heteroalkylene, cycloalkylene, heterocyclylene, arylene, heteroarylene, amidoalkylene, amidoheteroalkylene, and any combination thereof;

$R_e$ is a substituent selected from hydrogen, alkyl and heteroalkyl;

$L_4$ is a group of the formula:

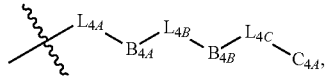

wherein:

$L_{4A}$ is a linker group selected from alkylene, heteroalkylene, cycloalkylene, heterocyclylene, arylene, heteroarylene, and any combination thereof;

$B_{4A}$ is absent or is a cleavable linker selected from —S—S—, —C(=O)O—, —OC(=O)—, —C(=O) NR$_c$—, —NR$_c$C(=O)—, —OC(=O)O—, —NR$_c$C(=O) O—, —OC(=O)NR$_c$— or —NR$_c$C(=O)NR$_d$—, —C(=O) NR$_c$C(=O)—, —C(=O)S—, —SC(=O)—, —SC(=O) S—, —OC(=O)S—, —SC(=O)O—, —OC(=S)O—, —SC(=S)S—, —NR$_c$SO$_2$—, —SO$_2$NR$_c$—, —NR$_c$SO$_2$NR$_d$—, —C(=O)NR$_c$NR$_d$—, —NR$_c$NR$_d$C (=O)—, —NR$_c$NR$_d$C(=O)O—, —OC(=O)NR$_c$NR$_d$—, —CR$_c$=N—NH—C(=O)—, —C(=O)NH—N=CR$_c$—, —CR$_c$=N—O—, —O—N=CR$_c$—, wherein R$_c$ and R$_d$ are each a substituent independently selected from hydrogen, alkyl, heteroalkyl, cycloalkyl, and heterocyclyl;

$L_{4B}$ is absent or is a linker group selected from alkylene, heteroalkylene, cycloalkylene, heterocyclylene, arylene, heteroarylene, amidoalkylene, amidoheteroalkylene and any combination thereof;

$B_{4B}$ is absent or is a cleavable linker selected from —S—S—, —C(=O)O—, —OC(=O)—, —C(=O) NR$_c$—, —NR$_c$C(=O)—, —OC(=O)O—, —NR$_c$C(=O) O—, —OC(=O)NR$_c$— or —NR$_c$C(=O)NR$_d$—, —C(=O) NR$_c$C(=O)—, —C(=O)S—, —SC(=O)—, —SC(=O) S—, —OC(=O)S—, —SC(=O)O—, —OC(=S)O—, —SC(=S)S—, —NR$_c$SO$_2$—, —SO$_2$NR$_c$—, —NR$_c$SO$_2$NR$_d$—, —C(=O)NR$_c$NR$_d$—, —NR$_c$NR$_d$C (=O)—, —NR$_c$NR$_d$C(=O)O—, —OC(=O)NR$_c$NR$_d$, —CR$_c$=N—NH—C(=O)—, —C(=O)NH—N=CR$_c$—, —CR$_c$=N—O—, —O—N=CR$_c$—, wherein R$_c$ and R$_d$ are each a substituent independently selected from hydrogen, alkyl, heteroalkyl, cycloalkyl, and heterocyclyl;

$L_{4C}$ is absent or is a linker group selected from alkylene, heteroalkylene, cycloalkylene, heterocyclylene, arylene, heteroarylene, amidoalkylene, amidoheteroalkylene and any combination thereof;

$C_{4A}$ is a linker group selected from:

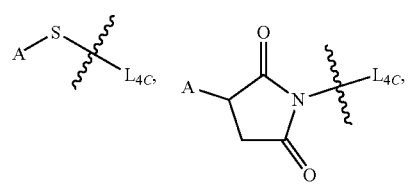

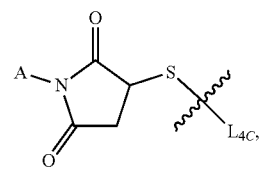

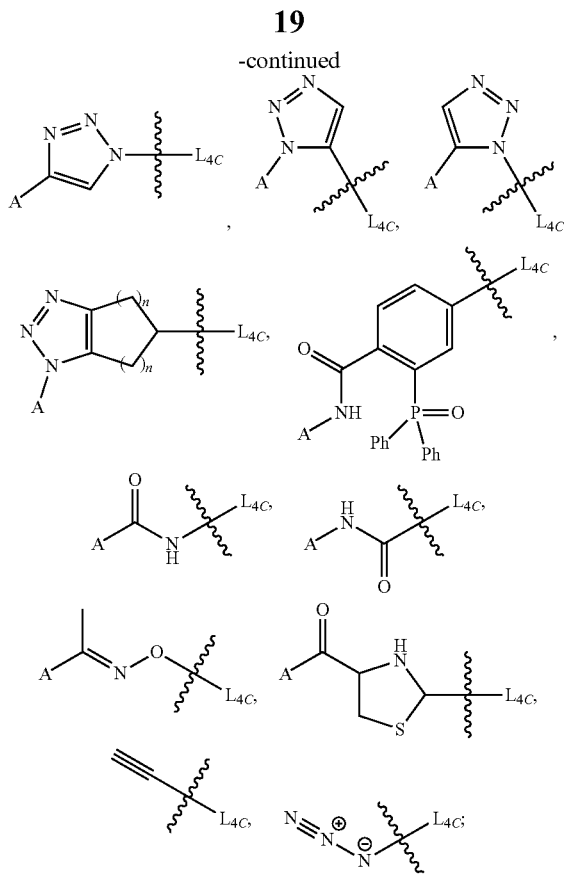

A is a targeting moiety, as described above, or H;

n is an integer ranging from 0-5 a is an integer from 1-1860;

b is an integer from 1-372;

c is an integer from 0-465;

d is an integer from 1-186; and with the proviso that the antibody-drug conjugate of Formula (I) must contain one or more therapeutic agent and one or more targeting moiety.

The invention also provides an antibody-drug conjugate of Formula (II) as shown below, comprising hydroxy monomeric blocks (a), (b) and (e):

(II)

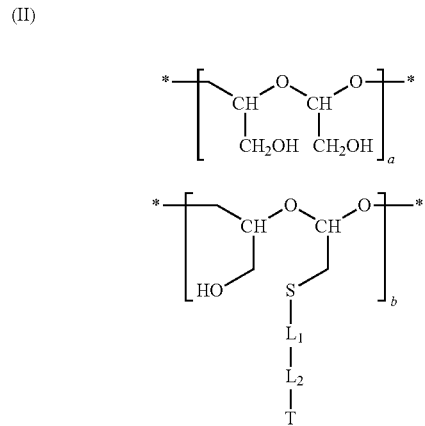

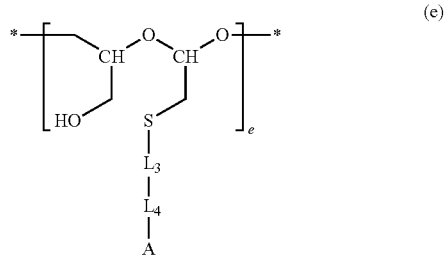

wherein *, $L_1$, $L_2$, T, $L_3$, $L_4$ and A are as described above;

a is an integer from 1-1860;

b is an integer from 1-372;

e is an integer from 1-186;

with the proviso that the antibody-drug conjugate of Formula (II) must contain one or more therapeutic agent and one or more targeting moiety.

In certain embodiments, cleavable linkers $B_{2A}$, $B_{2B}$, $B_{4A}$ and $B_{4B}$ can be enzymatically cleaved, be biodegradable, or can be cleaved by changes in pH (e.g. acid or base labile). Linkers that are cleavable under reducing or oxidizing conditions may also be used (review: Jain et al., Pharm. Res. 2015, 32, Pages 3526-3540). Cleavable linkers may be selected from, but are not limited to, one or more of the following structures:

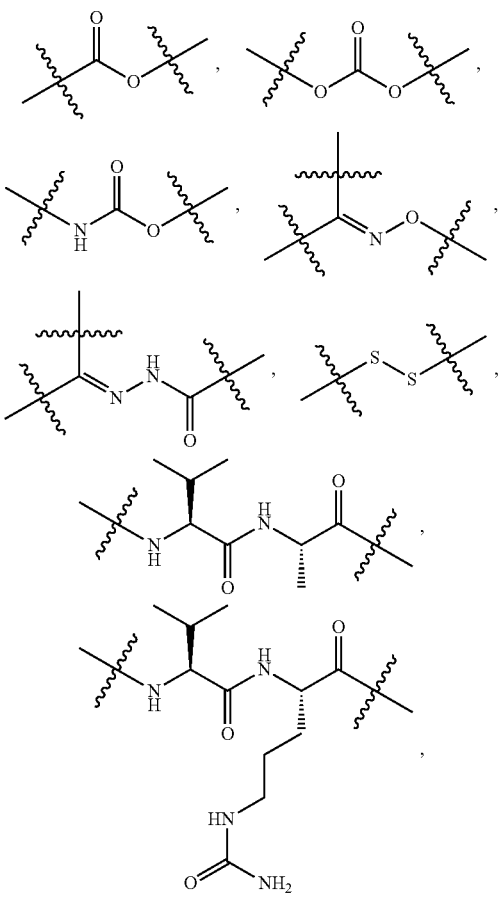

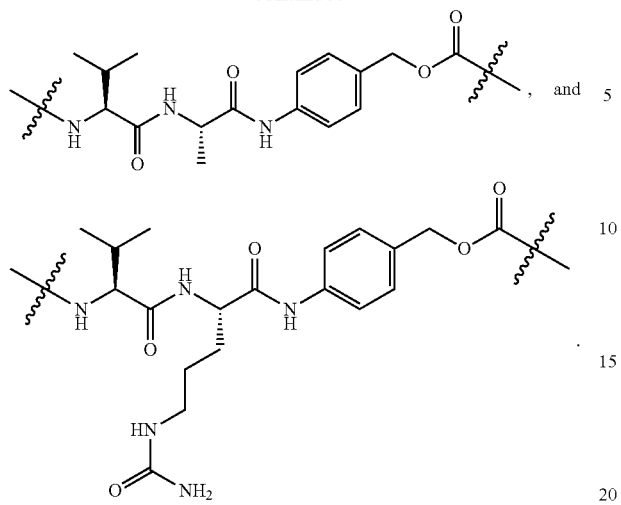, and

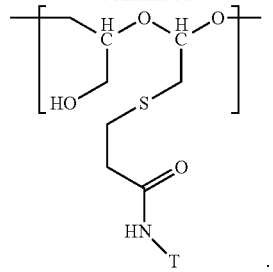

In certain embodiments, the targeting moiety possesses a nucleophilic group, allowing it to react with the electrophilic $C_{4A}$. In other embodiments, the targeting moiety comprises a site-specific modified non-natural amino acid with a chemical side chain that allows for biorthogonal conjugation chemistry with $C_{4A}$. In certain embodiments, the targeting moiety is modified with an azide or alkyne to allow for [3+2] cycloaddition with an alkyne or azide, respectively, on $C_{4A}$.

In yet other embodiments, the targeting moiety (A) can be linked to $L_{4C}$ through a cross-linking reagent selected from the group consisting of N-succinimidyl-4-(maleimidomethyl)cyclohexanecarboxylate (SMCC), sulfosuccinimidyl 4-(N-maleimidomethyl) cyclohexane-1-carboxylate (sulfo-SMCC), maleimide-polyethyleneglycol-N-hydroxysuccinimide, N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB), N-succinimidyl iodoacetate (SIA), N-succinimidyl bromoacetate (SBA) and N-succinimidyl 3-(bromoacetamido)propionate (SBAP).

Typically, the mole ratio of the therapeutic agent (T) to targeting moiety (A) is generally greater than 1:1. In some embodiments, the ratio is greater than about 5:1 or greater than about 8:1 or greater than about 10:1 or greater than about 12:1 or greater than about 15:1 or greater than about 18:1. In some embodiments, the ratio is between about 1:1 to about 20:1 (e.g., between about 5:1 to about 15:1, between about 8:1 to about 13:1, etc.).

In some embodiments, the compound of Formula (I) is Compound 16, Compound 17, Compound 25, or Compound 30:

In other embodiments, the linker $L_2$ does not have a cleavable linkage ($B_{2A}$ and $B_{2B}$ are both absent) and the therapeutic agent, T, can be cleaved off by antibody degradation (See U.S. Publication No. 2005/0238649 and reference herein). In some embodiments, monomer unit (b) has the structure:

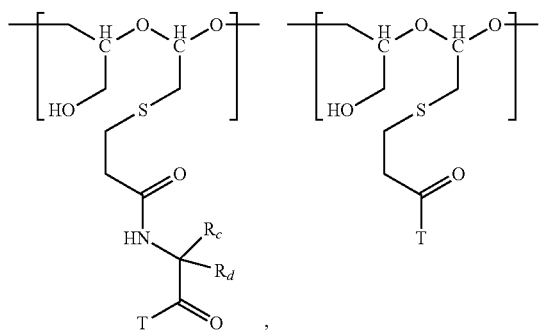, or

16

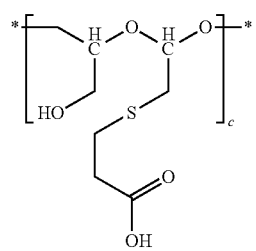

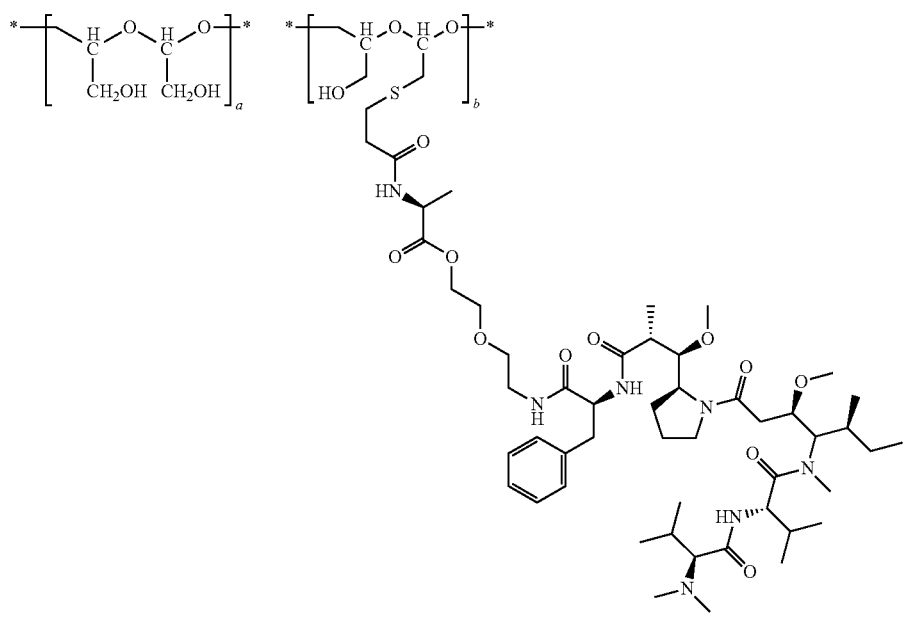

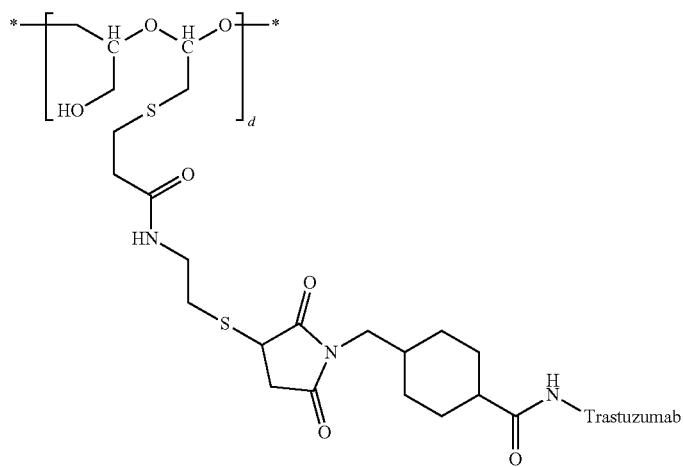
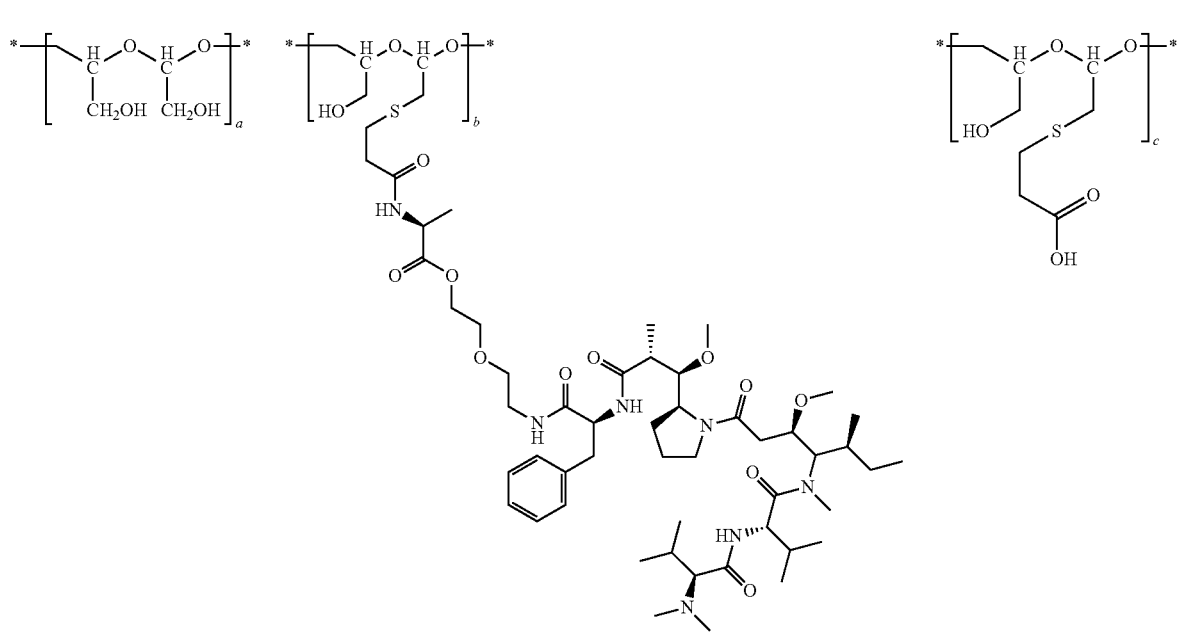
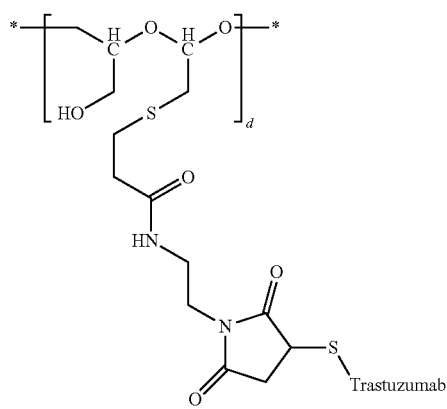

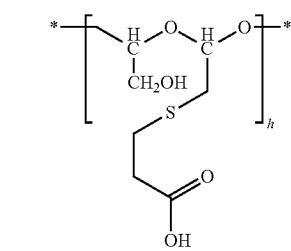
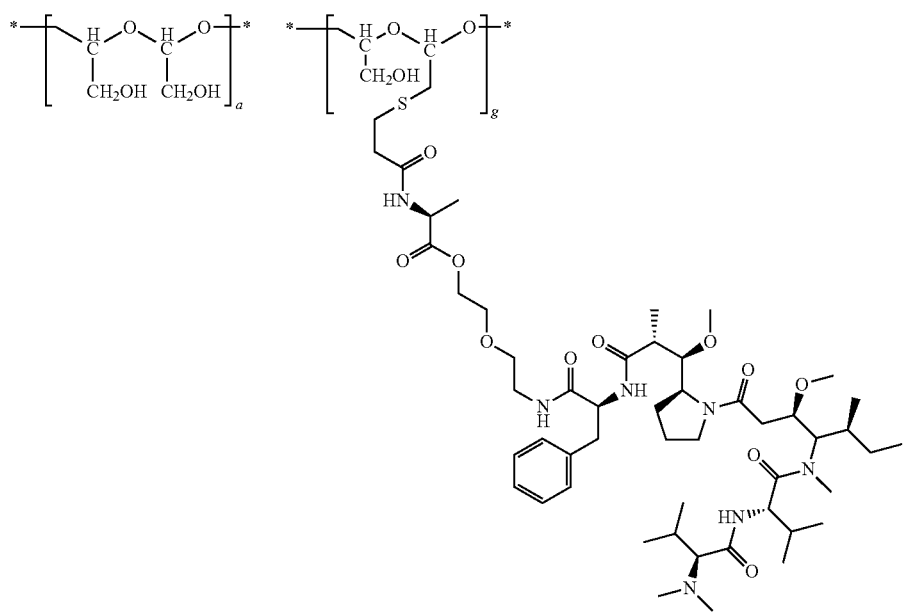
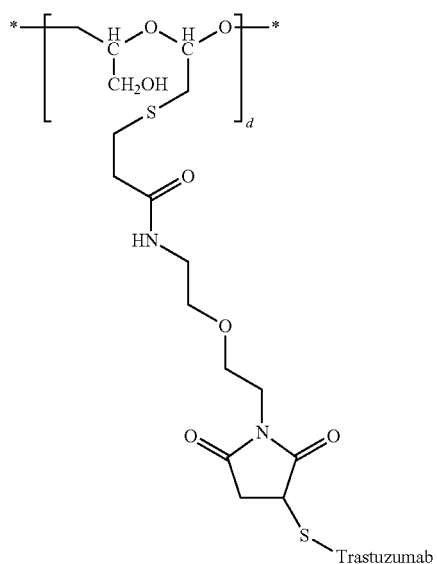

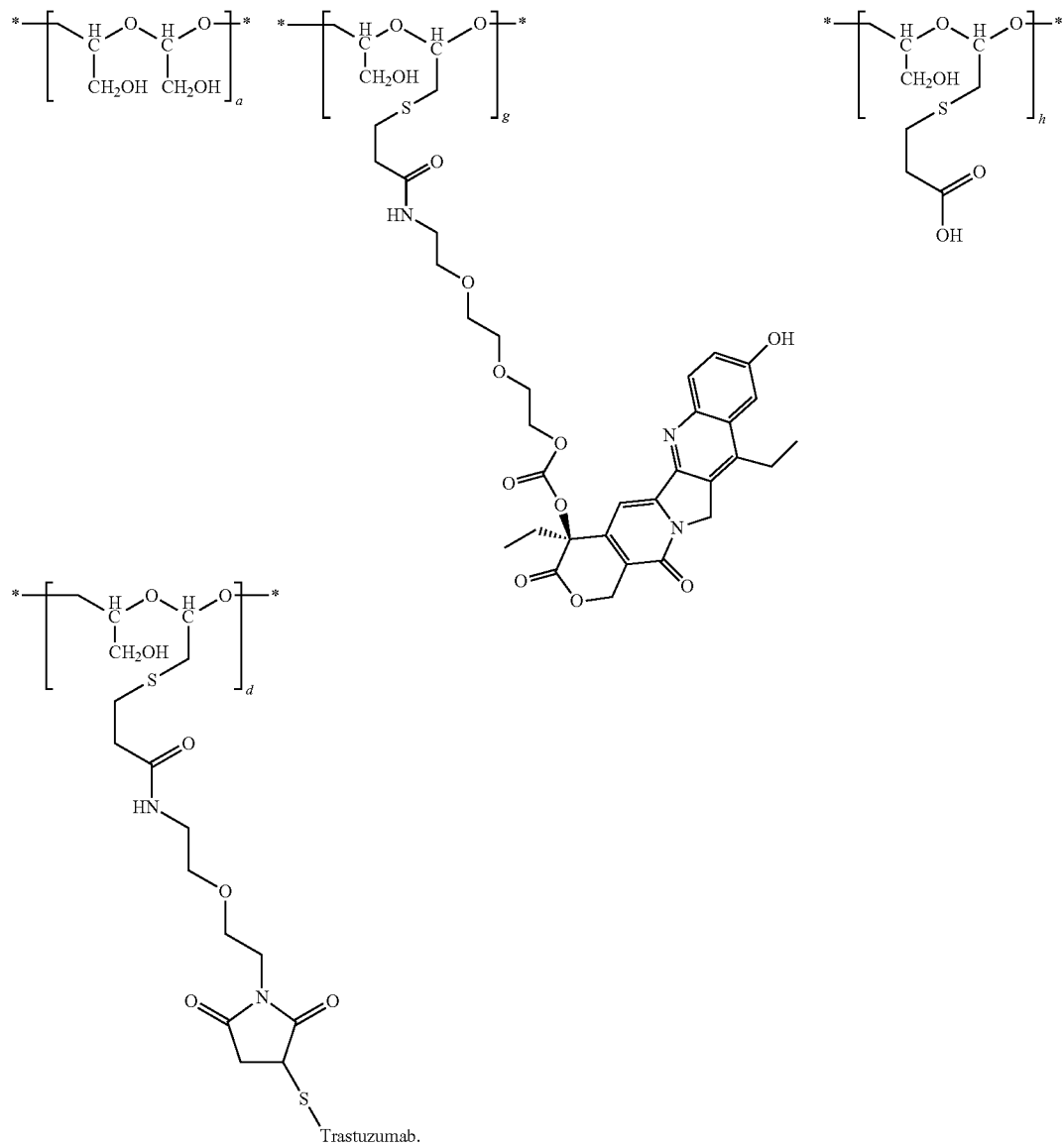
The invention also provides auristatin derivatives of Formula (III):
(III)
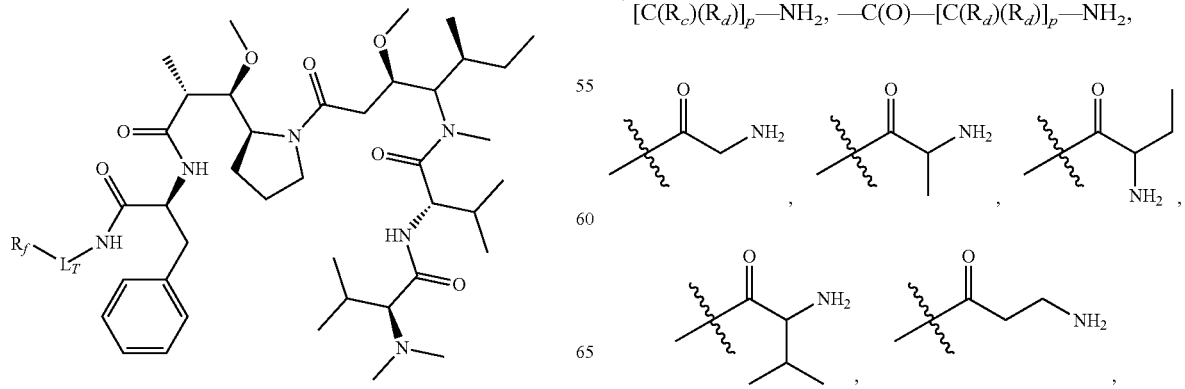
wherein $L_T$ is a linking moiety selected from —$(CH_2)_m$—, —$(OCH_2)_m$—, —$(OCH_2CH_2)_m$—, and —$(CH_2CH_2O)_m$—, "m" is an integer from 0 (i.e. $L_T$ is a bond) to 6; and
$R_f$ is selected from hydrogen, —$NH_2$, —C(O)—$NH_2$, —[C($R_c$)($R_d$)]$_p$—$NH_2$, —C(O)—[C($R_d$)($R_d$)]$_p$—$NH_2$,

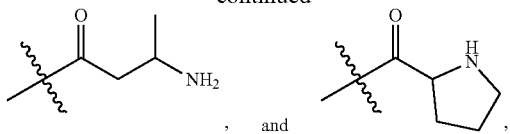

and "p" is an integer from 1-4. In some embodiments, the auristarin derivative has the structure:

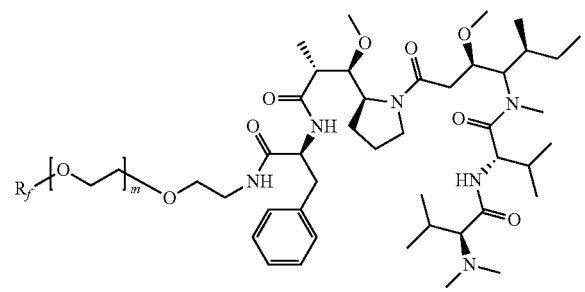

wherein "m" is an integer from 1-6; and $R_f$ is selected from:

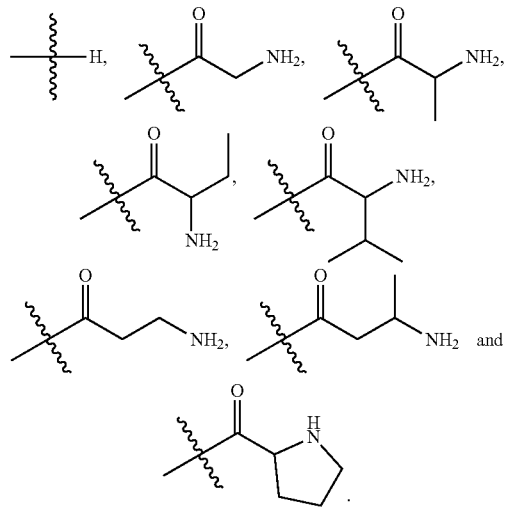

In some embodiments the auristarin derivative may be connected to a PHF polymer via a contacting the $R_f$ moiety with a polymer with a suitable functional group to form a covalent bond between the polymer and the auristarin derivative. In some embodiments, $R_f$ comprises the point of attachment of said camptothecin derivative to said compound. $R_f$ may be hydrogen (and if $R_f$ is hydrogen and the point of attachment, then it is a bond) or

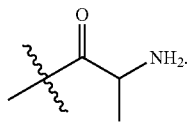

The invention also provides camptothecin derivatives having the structure of formula (IV):

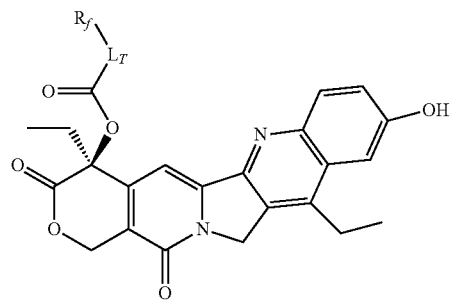

wherein $L_T$ is a linking moiety selected from —$(CH_2)_m$—, —$(OCH_2)_m$—, —$(OCH_2CH_2)_m$—, and —$(CH_2CH_2O)_m$—, "m" is an integer from 0 (i.e. $L_T$ is a bond) to 6; and $R_f$ is selected from hydrogen, —$NH_2$, —C(O)—$NH_2$, —[C($R_c$)($R_d$)]$_p$—$NH_2$, —C(O)—[C($R_c$)($R_d$)]$_p$—$NH_2$,

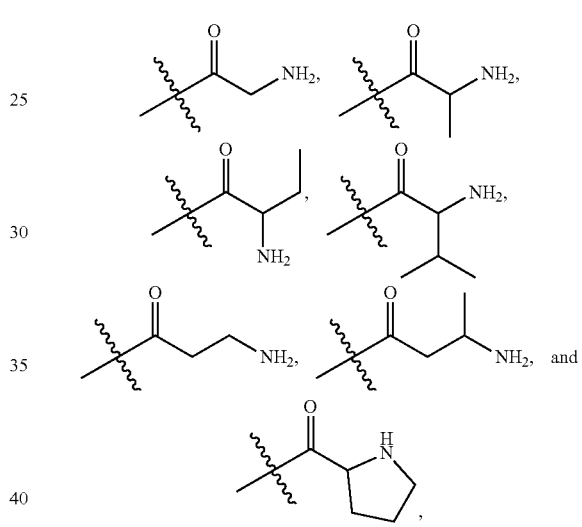

and "p" is an integer from 1-4. In some embodiments the camptothecin derivative may be connected to a PHF polymer via a contacting the $R_f$ moiety with a polymer with a suitable functional group to form a covalent bond between the polymer and the camptothecin derivative. In some embodiments, $R_f$ comprises the point of attachment of said camptothecin derivative to said compound. $R_f$ may be hydrogen (and if $R_f$ is hydrogen and the point of attachment, then it is a bond) or

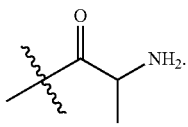 [SMILES: *C(=O)C(C)N]

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or mixtures thereof, or in the case where two or more chiral center are present, all diastereomers or mixtures thereof.

In certain embodiments, the compounds of the invention exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}H$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

In all of the embodiments provided herein, examples of suitable optional substituents are not intended to limit the scope of the claimed invention. The compounds of the invention may contain any of the substituents, or combinations of substituents, provided herein.

Salts

The compounds described herein may form salts with acids or bases, and such salts are included in the present invention. The term "salts" embraces addition salts of free acids or bases that are useful within the methods of the invention. The term "pharmaceutically acceptable salt" refers to salts that possess toxicity profiles within a range that affords utility in pharmaceutical applications. In certain embodiments, the salts are pharmaceutically acceptable salts. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Methods

The invention also provides a method of inhibiting cancer cells, the method comprising administering an anti-cancer effective amount of a composition comprising a compound of Formula (I). In another embodiment, provided herein is a method of inhibiting cancer cells, the method comprising administering an anti-cancer effective amount of a composition comprising a compound of Formula (II). In certain embodiments, the invention provides a method of treating or inhibiting cancer in a subject, the method comprising administering a composition comprising a compound of Formula (I) or Formula (II) to a subject in need thereof.

In some embodiments, the cancer can be HER2-positive cancer. In some embodiments, the cancer can be breast cancer. In some embodiments, the cancer can be HER2-positive breast cancer.

In some embodiments of the method, the HER2 is overexpressed in breast cancer cells. In some instances, the compound of Formula (I) or Formula (II) comprises an anti-neopalastic agent, such as Auristatin F, linked to the PHF polymer, such as in compound 16 or 17. In some embodiments, the compound of Formula (I) or Formula (II) includes an antibody, such as Trastuzumab, linked to the PHF polymer. Trastuzumab is known to bind to the extracellular domain of HER2 protein in HER2 overexpressing breast cancer cells. The compounds of the invention can enable the drug to be targeted to the cancer cell, thus minimizing off-target activity or toxicity.

In certain embodiments, the methods of the invention comprise administering a compound of Formula (I) or Formula (II) as part of a pharmaceutical composition, further comprising one or more additional ingredients. In some embodiments the compounds of the invention can be packaged as a lyophilized cake which can be reconstituted with a volume of sterile water.

In certain embodiments, the methods of the invention comprise administering a compound of Formula (I) or Formula (II) in combination with another compound or therapeutic agent such as an anti-tumor agent, chemotherapeutic, anti-cell proliferation agent or any combination thereof. In certain embodiments, the methods of the invention comprise administering a compound of Formula (I) or Formula (II) in combination with another standard breast cancer treatment method including, but not limited to, surgical intervention and radiation therapy.

In certain embodiments of the methods, the compounds of the invention can be administered to a subject in a dosage of between 1 ng/kg/day and 500 mg/kg/day. In some preferred embodiments, the compounds of the invention can be administered to a subject in a dosage of between 0.1 mg/kg to about 10 mg/kg. In some embodiments, the compounds are administered daily. In some embodiments, the compounds are administered every other day. In some embodiments, the compounds are administered once a week, once every other week, once a month or once every other month. In some embodiments, the compounds are administered as part of a standard chemotherapy regimen.

Synthesis

The compounds can be prepared from commercially available starting materials, compounds known in the literature, or readily prepared intermediates, by employing standard synthetic methods and procedures known to those skilled in the art. The compounds may also be prepared from the synthetic schema outlined in Examples 1-27. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

Synthetic chemistry transformations (including protecting group methodologies) useful in synthesizing the compounds described herein are known in the art and include, for example, those such as described in R. C. Larock, *Comprehensive Organic Transformations,* 2d. Ed., Wiley-VCH Publishers (1999); P. G. M. Wuts and T. W. Greene, *Protective Groups in Organic Synthesis,* 4th Ed., John Wiley and Sons (2007); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), and subsequent editions thereof.

The processes described herein can be monitored according to any suitable method known in the art. For example, product formation can be monitored by spectroscopic means, such as nuclear magnetic resonance spectroscopy (e.g., $^{1}H$ or $^{13}C$), infrared spectroscopy (FT-IR), spectrophotometry (e.g., UV-visible), or mass spectrometry (MS), or by chromatography such as high performance liquid chromatography (HPLC) or thin layer chromatography (TLC).

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis,* 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of compounds can be carried out by any of numerous methods known in the art. An example method includes preparation of the Mosher's ester or amide derivative of the corresponding alcohol or amine, respectively. The absolute configuration of the ester or amide is then determined by proton and/or $^{19}F$ NMR spectroscopy. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids. Resolution of racemic mixtures can also be carried out by elution on a column packed with an optically active resolving agent (e.g., dinitrobenzoylphenylglycine). Suitable elution solvent compositions can be determined by one skilled in the art.

Pharmaceutical Compositions and Formulations

The invention also encompasses the use of pharmaceutical compositions of at least one compound of the invention or a salt thereof to practice the methods of the invention.

Such a pharmaceutical composition may consist of at least one compound of the invention or a salt thereof, in a form suitable for administration to a subject, or the pharmaceutical composition may comprise at least one compound of the invention or a salt thereof, and one or more pharmaceutically acceptable carriers, one or more additional ingredients, or some combination of these. The at least one compound of the invention may be present in the pharmaceutical composition in the form of a physiologically acceptable salt, such as in combination with a physiologically acceptable cation or anion, as is well known in the art.

In certain embodiments, the pharmaceutical compositions useful for practicing the method of the invention may be administered to deliver a dose of between 1 ng/kg/day and 100 mg/kg/day. In other embodiments, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it may include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A non-limiting preservative is a combination of about 0.5% to 2.0% benzyl alcohol and 0.05% to 0.5% sorbic acid.

The composition preferably includes an antioxidant and a chelating agent which inhibit the degradation of the compound. Exemplary antioxidants for some compounds are BHT, BHA, alpha-tocopherol and ascorbic acid in the preferred range of about 0.01% to 0.3%, for example BHT in the range of 0.03% to 0.1% by weight by total weight of the composition. The chelating agent may be present in an amount of from 0.01% to 0.5% by weight by total weight of the composition. Exemplary chelating agents include edetate salts (e.g. disodium edetate) and citric acid in the weight range of about 0.01% to 0.20%, for example in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethyl cellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Administration/Dosing

The regimen of administration may affect what constitutes an effective amount. The therapeutic formulations may be administered to the patient either prior to or after surgical intervention related to cancer. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat cancer in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of cancer in a patient.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regimen and the precise dosage and composition to be administered to any patient will be determined by the attending physical taking all other factors about the patient into account.

Compounds of the invention for administration may be in the range of from about 1 mg to about 7,500 mg, about 20 mg to about 7,000 mg, about 40 mg to about 6,500 mg, about 80 mg to about 6,000 mg, about 100 mg to about 5,500 mg, about 200 mg to about 5,000 mg, about 400 mg to about 4,000 mg, about 800 mg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments therebetween. In certain preferred embodiments, the compounds of the invention can be administered to a subject in a dosage from about 0.1 mg/kg body weight to about 10 mg/kg body weight.

In some embodiments, the dose of a compound of the invention is from about 0.5 mg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of cancer in a patient.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing cancer in a patient.

Routes of Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pats. Nos. 4,256,108; 4,160,452; and 4,265,874 to form osmotically controlled release tablets.

Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compounds of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the methods of the invention, and a further layer providing for the immediate release of one or more compounds useful within the methods of the invention. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution or as a lyophilized cake which can be reconstituted by the addition of a solvent. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells.

One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Controlled Release Formulations and Drug Delivery Systems

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples are put forth so as to provide those of ordinary skill in the art with a complete disclosure and description of how to make and use the assay, screening, and methods, and are not intended to limit the scope of what the inventor(s) regard(s) as the invention.

EXAMPLES

The compounds disclosed herein may be synthesized using techniques well-known in the art of organic synthesis. The starting materials and intermediates required for the synthesis may be obtained from commercial sources, and/or synthesized according to methods known to those skilled in the art and/or disclosed elsewhere herein.

The following Examples are provided for the purpose of illustration only, and the disclosure is not limited to these Examples, but rather encompasses all variations that are evident as a result of the teachings provided herein.

Abbreviations
  µl=microliters
  Boc or BOC=tert-butoxycarbonyl
  DMAP=4-Dimethylaminopyridine
  DMSO=dimethyl sulfoxide
  DTT=dithiothreitol
  EDC=1-ethyl-3-(3-dimethylaminopropyl)carbodiimide
  ESI or ES=Electrospray ionization
  g=grams
  h=hour
  HPLC=high-performance liquid chromatography
  LC=liquid chromatography
  LCMS=liquid chromatography mass spectrometry
  min=minute
  mg=milligrams
  ml=milliliters
  mmol=millimoles
  MS=mass spectrometry
  MWCO=molecular weight cut off
  NMR=nuclear magnetic resonance spectroscopy
  PBS=phosphate-buffered saline, 0.9% NaCl
  SPA=3-sulfanylpropionic acid
  SSPy=2-(pyridine-2-yldisulfanyl)
  TEAA=triethylammonium acetate
  TFA=trifluoroacetic acid
  Ts or tosyl=p-toluenesulfonyl Variables *, a, b, c, d and e have the ranges as described above and herein.

Example 1

General Preparation Methods

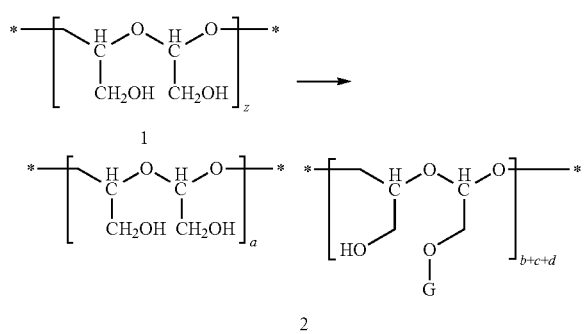

Poly-1-hydroxymethylethylene hydroxymethyl formal (PHF) 1 may be reacted with an electrophilic reagent to form polymer 2 where G is an activating group, such as tosyl, methanesulfonyl, or trifluoromethanesulfonyl. Generally, more than 3 must be present in polymer 1. Variables a, b, c and d are as described above. In this described general preparation method, z is a+b+c+d which is < or =1862.

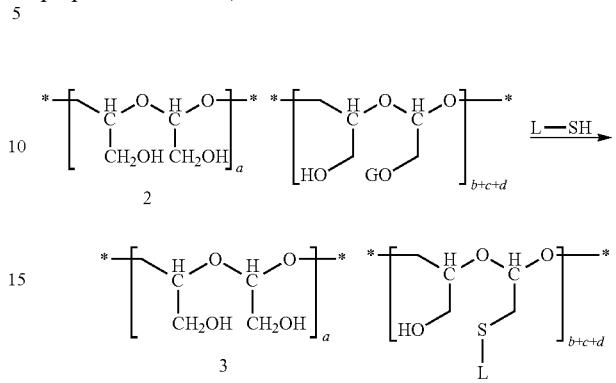

The activating group G can be displaced by thiol L-SH to form polymer 3 having a sulfide linker. In one embodiment, L is a group that can be covalently linked to a drug or small molecule. In another embodiment, L is a group already linked to a drug or small molecule.

Alternatively, the sulfide linker can also be formed as follows:

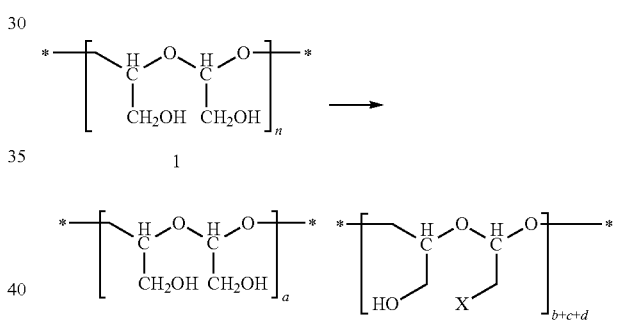

Here, a leaving group X such as bromo or chloro is installed by through a nucleophilic substitution reaction to give polymer 4. A thiol L-SH can then displace the halide to form the sulfide 3 as shown below.

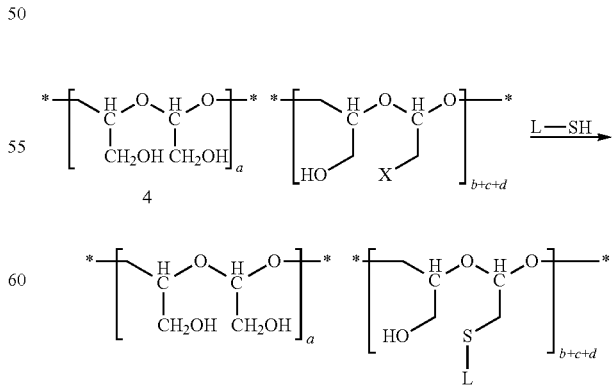

Example 2

Synthesis of poly(1-carbonylethylene carbonyl formal) (Compound 6)

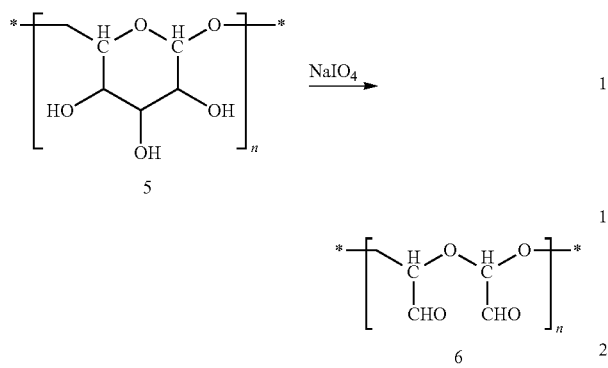

Dextran (5, 8.0 g, Mn 15 KDa-25 KDa, from *Leuconostoc* spp.) was dissolved in 20 ml of deionized water. A solution of sodium metaperiodate (26.38 g, 0.123 mol) dissolved in 480 ml of deionized water was added into the dextran solution at 0-5° C. in a light protected flask. The reaction mixture was stirred for 3 h at 0-5° C., and then at 25° C. for 11 hours. The reaction mixture was desalted using diafiltration (Amicon Ultra-15 centrifugal filter, molecular weight cut off (MWCO): 3K), and concentrated to 60 ml. The pH of the product solution was adjusted to 8-9 by adding 5.0 N sodium hydroxide solution dropwise. The poly(1-carbonylethylene carbonyl formal) (compound 6) solution was directly used in the next step.

Example 3

Synthesis of poly(1-hydroxymethylethylene hydroxy-methyl formal) (Compound 1)

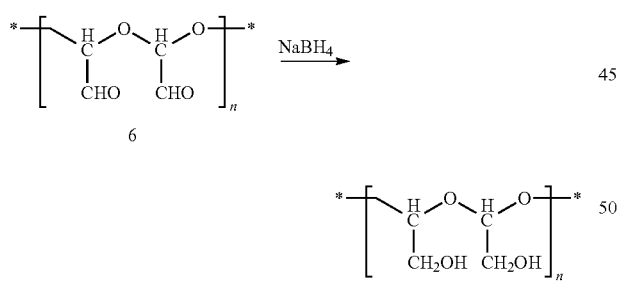

Sodium borohydride (4.31 g, 0.113 mol) was added into 10 ml deionized water, and stirred for 2 min at 0° C., followed by the addition of starting poly(1-carbonylethylene carbonyl formal) (compound 6, 6.42 g, in 60 ml water) at 0° C. The reaction mixture was stirred at 0° C. for 2 hours. The pH of the reaction solution was adjusted to pH 7, by slowly adding 1.0 N aqueous hydrogen chloride solution. The resultant solution was desalted by diafiltration, using Amicon Ultra-15 centrifugal filter (MWCO: 3K). The solution was lyophilized to give poly(1-hydroxymethylethylene hydroxy-methyl formal) (compound 1) as a colorless solid (1.2 g). 1H NMR (400 MHz, DMSO-$d_6$:$D_2O$=95:5) δ ppm 3.30-3.41 (m, 2H), 3.46 (d, J=4.89 Hz, 2H), 3.60-3.67 (m, 2H), 3.67-3.75 (m, 1H), 4.64 (t, J=5.26 Hz, 1H).

Example 4

Synthesis of poly(1-hydroxymethylethylene hydroxy-methyl formal)-tosyl (Compound 7)

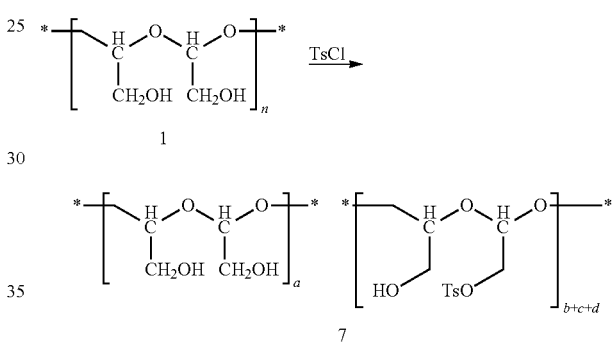

Poly(1-hydroxymethylethylene hydroxy-methyl formal) (compound 1, 0.21 g) was dissolved in anhydrous pyridine (2.2 ml) at 0° C., followed by the addition of tosyl chloride (90 mg). The reaction mixture was first stirred for one hour 0° C., then warmed to 25° C. and stirred for 16 hours. Pyridine was evaporated in vacuo and the product (poly(1-hydroxymethylethylene hydroxy-methyl formal)-tosyl, compound 7) was directly used in the next step, without isolation or purification.

Example 5

Synthesis of poly(1-hydroxymethylethylene hydroxy-methyl formal)-SPA (Compound 8)

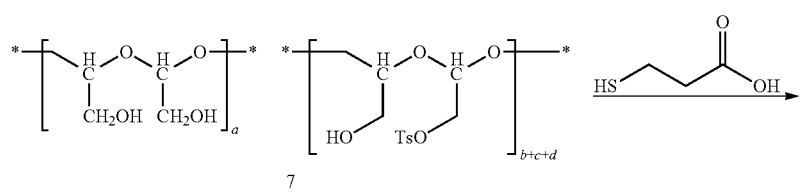

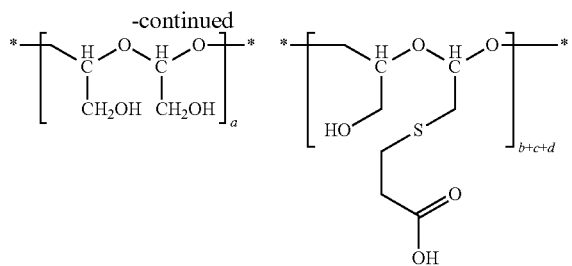

8

Potassium carbonate (2.14 g, 15.5 mmol) was added into a solution of poly(1-hydroxymethylethylene hydroxy-methyl formal)-tosyl (compound 7) in methanol (10.0 ml) at 15° C., followed by the addition of 3-mercaptopropionic acid (0.329 g, 0.27 ml, 3.10 mmol). The reaction mixture was stirred at 15° C. for 16 hours. 3-mercaptopropionic acid (0.11 g, 0.09 ml, 1.03 mmol) was added and the reaction mixture was heated to 40° C. for 8 hours. The reaction solution was cooled to room temperature and concentrated in vacuo. Water (15.0 ml) was added and stirred for 30 minutes at 15° C. The solid was filtered and the filtrate was desalted by diafiltration, using Amicon Ultra-15 centrifugal filter (MWCO: 3K). The desalted solution was lyophilized to afford poly(1-hydroxymethylethylene hydroxy-methyl formal)-SPA (compound 8) as a colorless solid (298 mg). $^1$H NMR (400 MHz, D$_2$O) shows the methylene group adjacent to acid (δ ppm 2.39, t, J=6.35 Hz). The 3-sulfanylpropionic acid content was found to be 12%, as determined by NMR.

Example 6

Synthesis of poly(1-hydroxymethylethylene hydroxy-methyl formal)-SPA-maleimide (Compound 9)

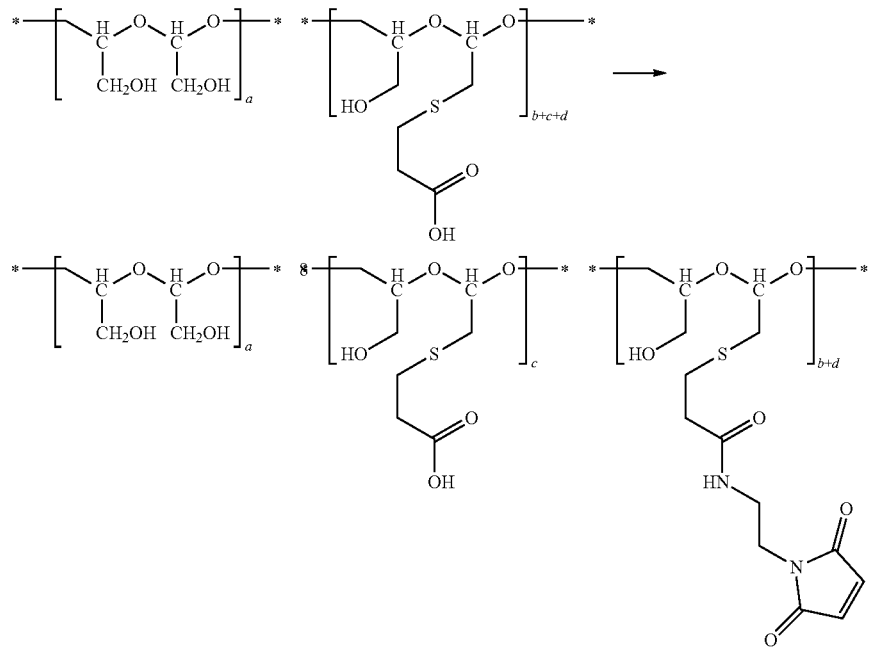

9

N-Hydroxysuccinimide (18 mg, 0.155 mmol) was added into a solution of poly(1-hydroxymethylethylene hydroxy-methyl formal)-SPA (compound 8, 200 mg, 3-sulfanylpropionic acid content: 19%) in deionized water (1 ml) at 0° C. EDC (24 mg, 0.027 ml, 0.155 mmol) was added into the reaction solution at 0° C., followed by the addition of N-(2-aminoethyl)maleimide trifluoroacetic acid salt (39 mg, 0.155 mmol). The reaction solution was warmed to 20° C. and stirred for 16 hours. The reaction mixture was filtered and the filtrate was desalted by diafiltration, using Amicon Ultra-15 centrifugal filter (MWCO: 3K). The desalted solution was lyophilized to give poly(1-hydroxymethylethylene hydroxy-methyl formal)-SPA-maleimide (compound 9) as a colorless solid (106 mg). The maleimide content was found to be 6%, as determined by NMR.

Example 7

Synthesis of poly(1-hydroxymethylethylene hydroxy-methyl formal)-SPA-SSPy (Compound 10)

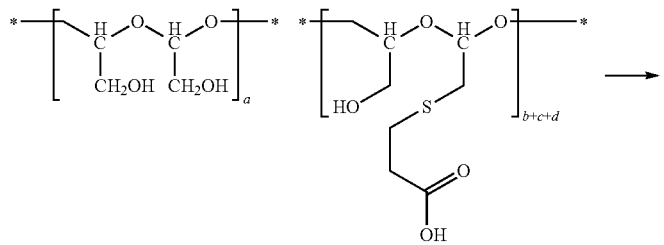

8

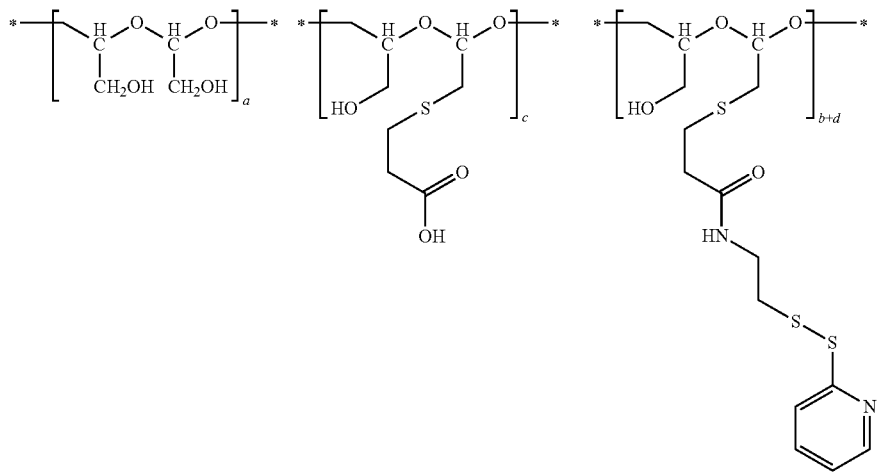

10

N-Hydroxysuccinimide (7 mg, 0.062 mmol) was added into a solution of poly(1-hydroxymethylethylene hydroxy-methyl formal)-SPA (compound 8, 149 mg, 3-sulfanylpropionic acid content: 12%) in deionized water (1 ml) at 0° C. EDC (10 mg, 0.011 ml, 0.062 mmol) was added into the reaction solution at 0° C., followed by the addition of pyridine dithioethylamine hydrochloride (14 mg, 0.062 mmol). The reaction solution was warmed to 20° C. and stirred for 16 hours. The reaction mixture was filtered and the filtrate was desalted by diafiltration, using Amicon Ultra-15 centrifugal filter (MWCO: 3K). The desalted solution was lyophilized to give poly(1-hydroxymethylethylene hydroxy-methyl formal)-SPA-SSPy (compound 7) as a colorless solid (100 mg). 1H NMR (400 MHz, D$_2$O) shows the pyridine group on SSPy: δ ppm 8.33 (br.s, 1H), 7.77 (br.s, 1H), 7.23 (br.s, 1H). The SSPy content was found to be 4%, as determined by NMR.

Example 8

Synthesis of auristatin F 2-(2-hydroxy-ethoxy)-ethylamide (Compound 11)

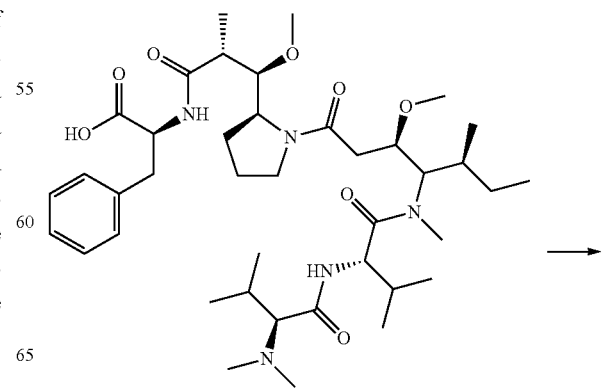

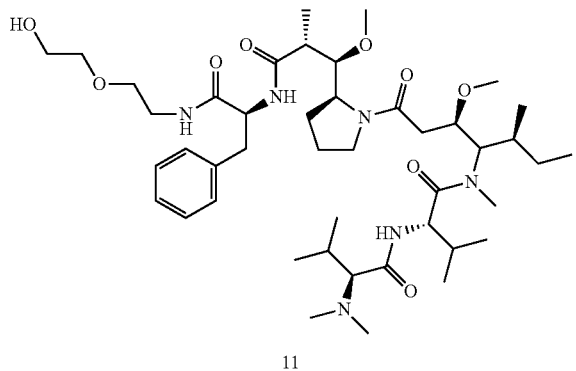

11

N,N-Diisopropylethylamine (26 mg, 0.034 ml, 0.198 mmol) was added into a solution of auristatin F hydrochloride (52 mg, 0.066 mmol) in anhydrous DMF (1.4 ml) at 10° C., followed by the addition of (1-[bis(dimethylamino) methylene]-1H-1,2,3-triazolo[4,5-b]pyridinium-3-oxid hexafluorophosphate) (50 mg, 0.132 mmol). Reaction solution was stirred at 10° C. for 15 min, then 2-(2-amino-ethoxy)-ethanol (0.021 mg, 0.020 ml, 0.198 mmol) was added and the reaction solution was stirred at 10° C. for 16 hours. The solvent was removed in vacuo, and the residue was purified by reverse-phase preparatory HPLC to afford auristatin F 2-(2-hydroxy-ethoxy)-ethylamide (compound 11, TFA salt, 16.9 mg) as a white solid. Mass calculated for $C_{44}H_{76}N_6O_9+H$, $[M+H]^+$ 833.57, observed LC/MS (ESI) m/z 833.29 $[M+H]^+$, 855.25 $[M+Na]^+$.

Example 9

Synthesis of auristatin F 2-(2-hydroxy-ethoxy)-ethylamide Boc-L-Alanine (Compound 12)

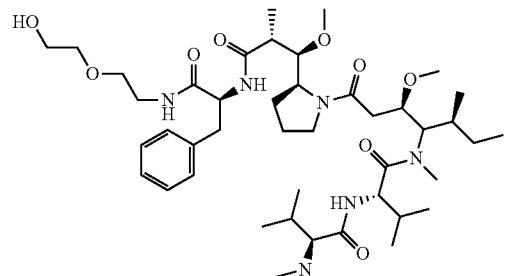

11

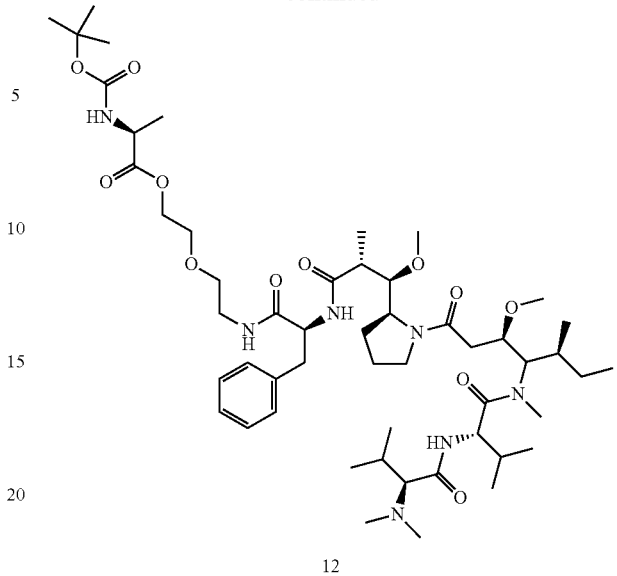

12

Boc-L-Alanine (14 mg, 0.072 mmol) and DMAP (11 mg, 0.09 mmol) was dissolved in anhydrous dichloromethane (2.0 ml), followed by the addition of diisopropylcarbodiimide (9 mg, 0.072 mmol) at 0° C. Auristatin F 2-(2-hydroxyethoxy)-ethylamide (compound 11, TFA salt, 16.9 mg) was added at 0° C., and the reaction mixture was stirred at 23° C. for 21 hours. The reaction mixture was concentrated in vacuo, and the residue was purified by reverse-phase preparatory HPLC to afford auristatin F 2-(2-hydroxy-ethoxy)-ethylamide Boc-L-Alanine (compound 12, TFA salt, 11.6 mg) as a white solid. Mass calculated for $C_{52}H_{89}N_7O_{12}+H$, $[M+H]^+$ 1004.66, observed LC/MS (ESI) m/z 1004.33 $[M+H]^+$, 1026.29 $[M+Na]^+$.

Example 10

Synthesis of auristatin F 2-(2-hydroxy-ethoxy)-ethylamide L-alanine (Compound 13)

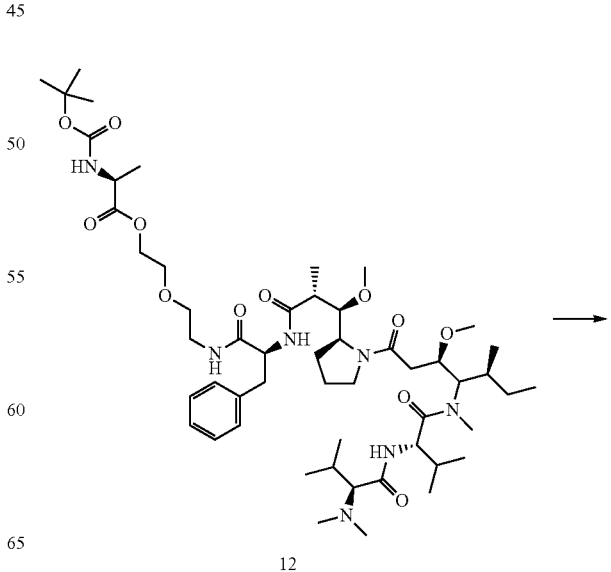

12

-continued

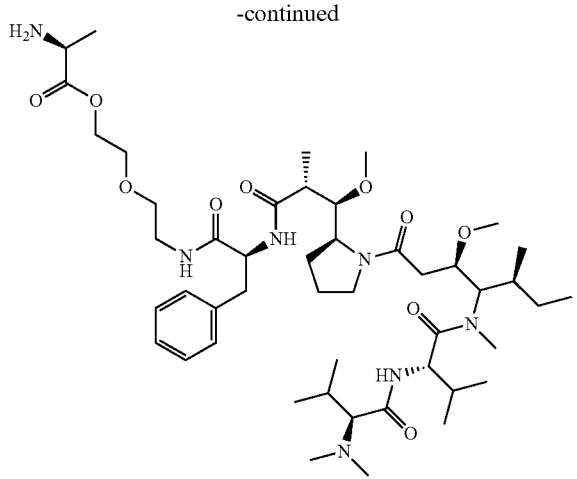

13

Trifluoroacetic acid (0.10 ml) was added dropwise to a solution of auristatin F 2-(2-hydroxy-ethoxy)-ethylamide Boc-L-Alanine (compound 12, TFA salt, 11.6 mg, 0.01 mmol) in dichloromethane (0.3 ml), and the reaction solution was stirred for one hour at 25° C. The reaction mixture was concentrated in vacuo. The residue was dissolved in dichloromethane (1 ml), followed by the addition of ethyl acetate. The precipitation was collected to give auristatin F 2-(2-hydroxy-ethoxy)-ethylamide L-Alanine (compound 12, TFA salt, 10 mg). Mass calculated for $C_{47}H_{81}N_7O_{10}$+H, $[M+H]^+$ 904.60, observed LC/MS (ESI) m/z 904.27 $[M+H]^+$, 926.30 $[M+Na]^+$.

Example 11

Synthesis of poly(1-hydroxymethylethylene hydroxy-methyl formal)-SPA-(auristatin F 2-(2-hydroxy-ethoxy)-ethylamide L-Alanine)-maleimide (Compound 14)

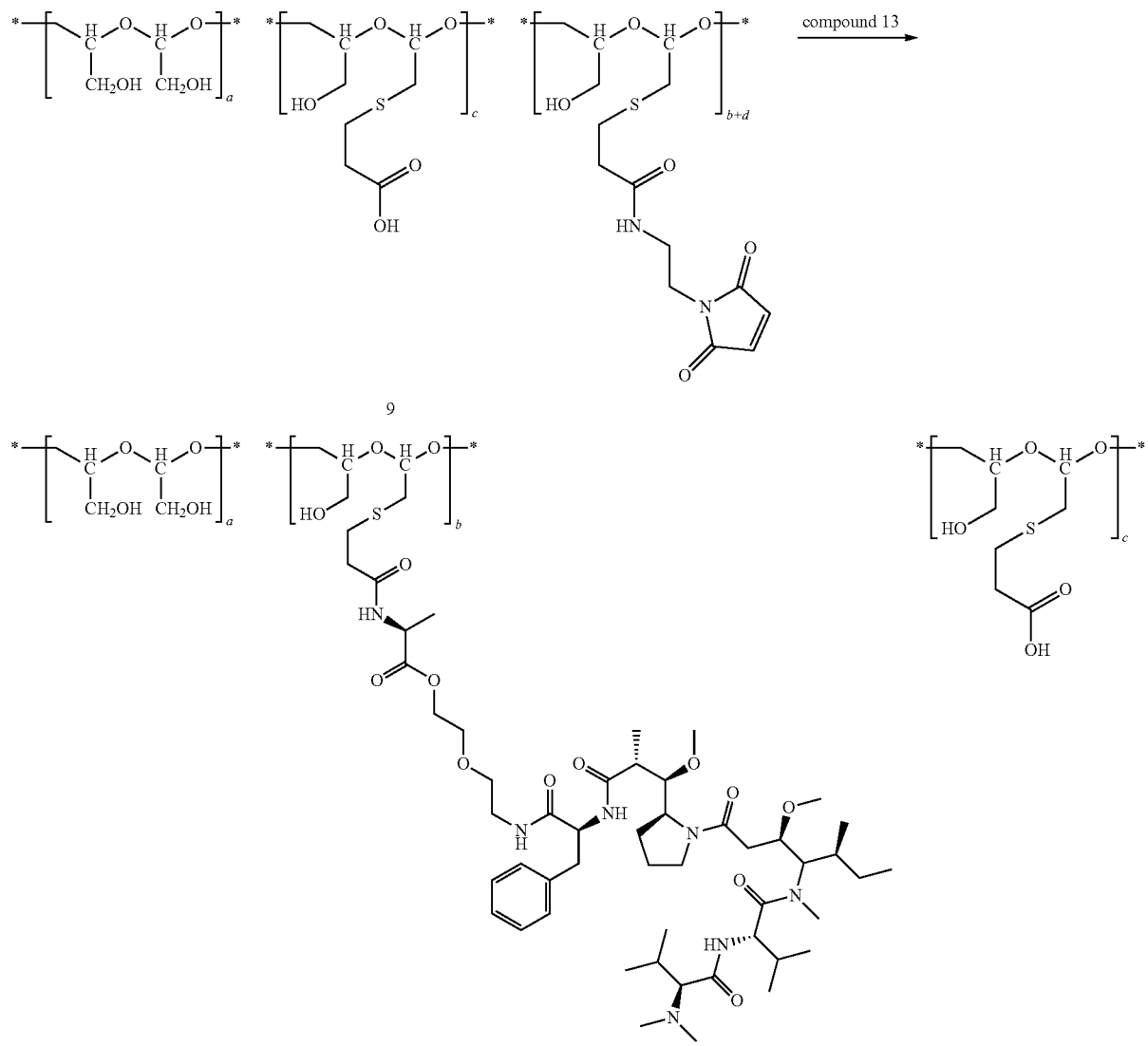

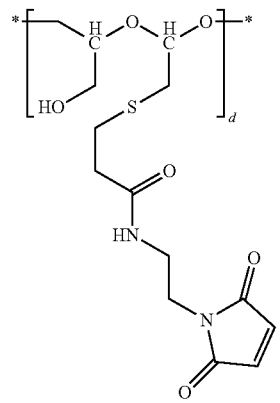

14

N-Hydroxysuccinimide (1.5 mg, 0.013 mmol) was added into a solution of poly(1-hydroxymethylethylene hydroxy-methyl formal)-SPA-maleimide (compound 9, 15 mg, 3-sulfanylpropionic acid content: 13%, maleimide content: 6%) in deionized water (0.8 ml) at 10° C. EDC (2.0 mg, 2.3 µl, 0.013 mmol) was added into the reaction solution at 10° C., followed by the addition of auristatin F 2-(2-hydroxy-ethoxy)-ethylamide L-Alanine (compound 13, TFA salt, 5 mg) in acetonitrile (0.4 ml). The reaction solution was warmed to 23° C. and stirred for 18 hours. The reaction mixture was filtered and concentrated in vacuo. The residue was diluted with deionized water (1.0 ml) and desalted by diafiltration, using Amicon Ultra-15 centrifugal filter (MWCO: 3K). The desalted solution was lyophilized to give poly(1-hydroxymethylethylene hydroxy-methyl formal)-SPA-(auristatin F 2-(2-hydroxy-ethoxy)-ethylamide L-Alanine)-maleimide (compound 14) as a colorless solid. 1H NMR (400 MHz, D$_2$O) shows the phenyl group on auristatin F: δ ppm 7.11-7.31 (m, 5H). The auristatin F 2-(2-hydroxy-ethoxy)-ethylamide L-Alanine content was found to be 6%, as determined by NMR.

Example 12

Synthesis of poly(1-hydroxymethylethylene hydroxy-methyl formal)-SPA-(auristatin F 2-(2-hydroxy-ethoxy)-ethylamide L-Alanine)-SSPy (Compound 15)

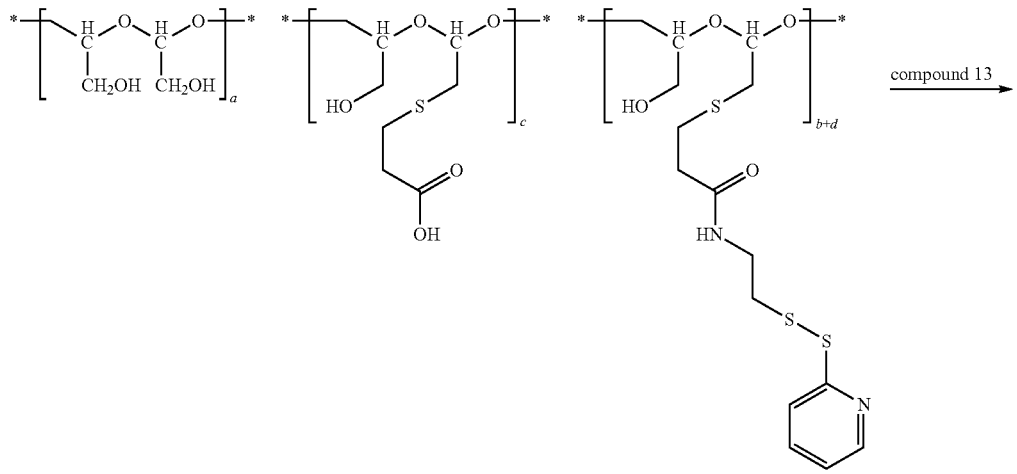

10

-continued

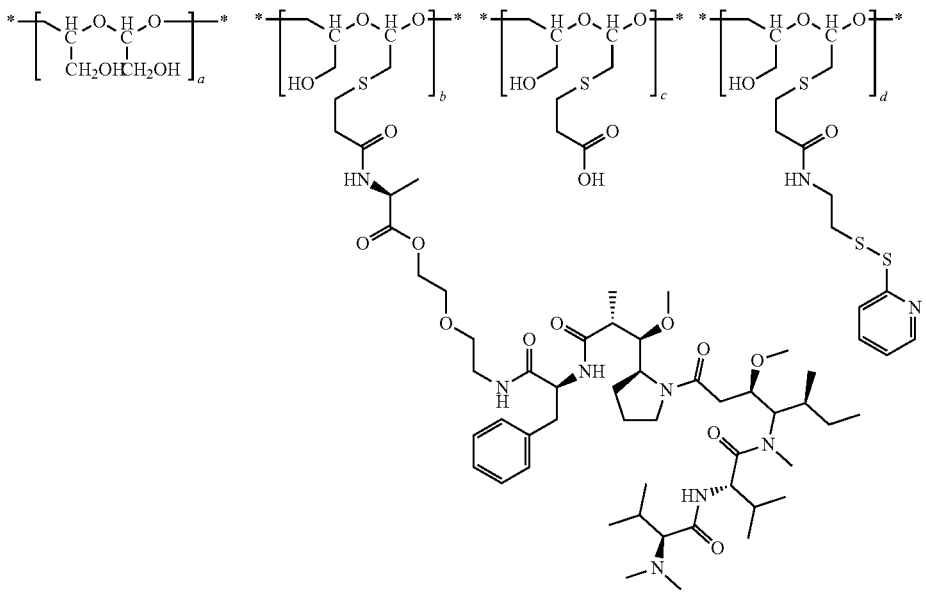

15

N-Hydroxysuccinimide (1.5 mg, 0.013 mmol) was added into a solution of poly(1-hydroxymethylethylene hydroxymethyl formal)-SPA-SSPy (compound 10, 15 mg, 3-sulfanylpropionic acid content: 8%, SSPy content: 4%) in deionized water (0.8 ml) at 10° C. EDC (2.0 mg, 2.3 μl, 0.013 mmol) was added into the reaction solution at 10° C., followed by the addition of auristatin F 2-(2-hydroxy-ethoxy)-ethylamide L-Alanine (compound 13, TFA salt, 5 mg) in acetonitrile (0.4 ml). The reaction solution was warmed to 23° C. and stirred for 18 hours. The reaction mixture was filtered and concentrated in vacuo. The residue was diluted with deionized water (1.0 ml) and desalted by diafiltration, using Amicon Ultra-15 centrifugal filter (MWCO: 3K). The desalted solution was lyophilized to give poly(1-hydroxymethylethylene hydroxy-methyl formal)-SPA-(auristatin F 2-(2-hydroxy-ethoxy)-ethylamide L-Alanine)-SSPy (compound 15) as a colorless solid. 1H NMR (400 MHz, D₂O) shows the phenyl group on auristatin F: δ ppm 7.11-7.31 (m, 5H). The auristatin F 2-(2-hydroxy-ethoxy)-ethylamide L-Alanine content was found to be 4.8%, as determined by NMR.

Example 13

Preparation of poly(1-hydroxymethylethylene hydroxy-methyl formal)-SPA-(auristatin F 2-(2-hydroxy-ethoxy)-ethylamide L-Alanine)-(Trastuzumab-MCC) (Compound 16)

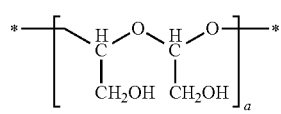

16

-continued

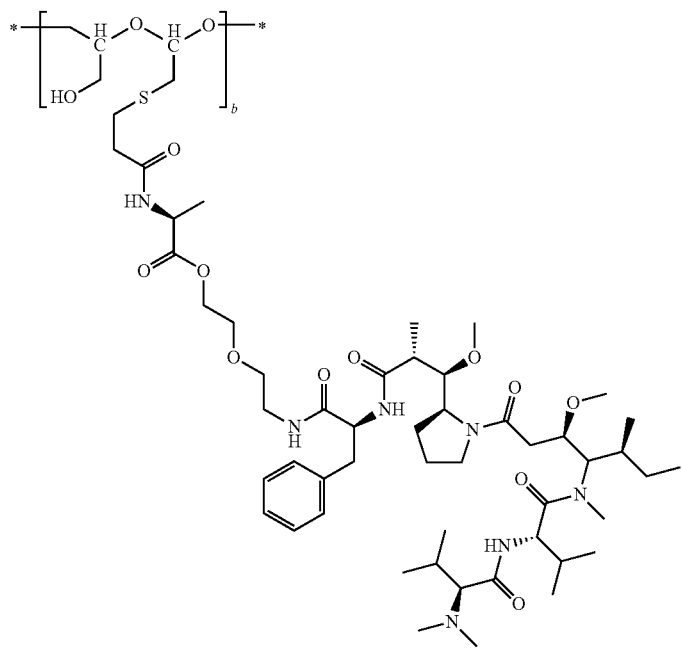
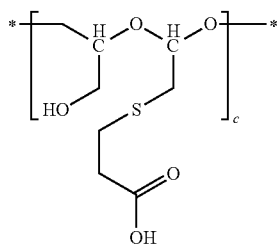
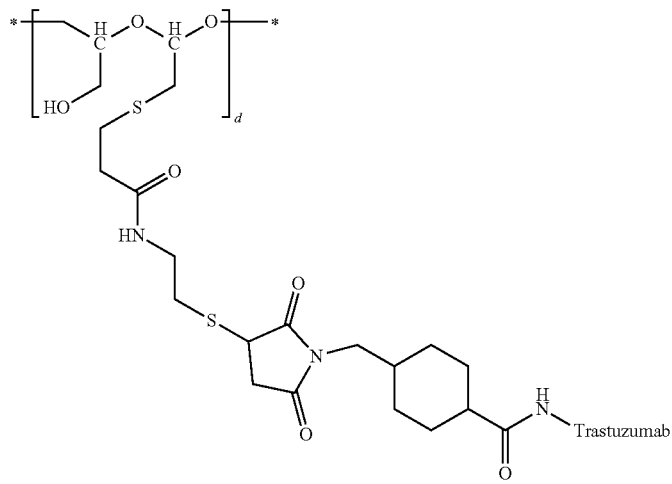

A solution of succinimidyl-4-(N-maleimidomethyl)cyclohexane-1-carboxylate (SMCC) in DMSO (5 µl, 15 mg/ml) was added into a solution of Trastuzumab (5 mg) in TEAA buffer (1.0 ml, pH=7.0). The reaction mixture was stirred for 3 hours at 25° C. The reaction mixture was desalted by diafiltration, using Amicon Ultra centrifugal filter (MWCO: 30K) to give Trastuzumab-MCC. Trastuzumab-MCC was stored in PBS buffer (pH=7.0, 20 mg/ml).

Dithiothreitol (DTT, 5.0 mg) was added into a solution of poly(1-hydroxymethylethylene hydroxy-methyl formal)-SPA-(auristatin F 2-(2-hydroxy-ethoxy)-ethylamide L-Alanine)-SSPy (compound 15, 5 mg) in deionized water (0.25 ml). The mixture was stirred at 23° C. for 30 min, the diluted with deionized water (1 ml). The reaction solution was purified with Amicon Ultra-15 centrifugal filter (cutoff: 3K) to give poly(1-hydroxymethylethylene hydroxy-methyl formal)-SPA-(auristatin F 2-(2-hydroxy-ethoxy)-ethylamide L-Alanine)-SH (stored concentration: 20 mg/ml in deionized water).

A solution of poly(1-hydroxymethylethylene hydroxymethyl formal)-SPA-(auristatin F 2-(2-hydroxy-ethoxy)-ethylamide L-Alanine)-SH (3 mg) in deionized water (150 µl) was added into a solution of Trastuzumab-MCC (3 mg) in PBS buffer (pH=7.0, 350 µl). The reaction mixture was stirred for 5 hours at 23° C., and purified by size-exclusion chromatography using Superose-6 column (eluant: PBS buffer, pH=7.0) to give poly(1-hydroxymethylethylene hydroxy-methyl formal)-SPA-(auristatin F 2-(2-hydroxy-ethoxy)-ethylamide L-Alanine)-(Trastuzumab-MCC) (compound 16). HPLC analysis determined molar ratio of auristatin F to Trastuzumab is about 9:1 to 12:1.

Example 14

Preparation of poly(1-hydroxymethylethylene hydroxy-methyl formal)-SPA-(auristatin F 2-(2-hydroxy-ethoxy)-ethylamide L-Alanine)-Trastuzumab (Compound 17)

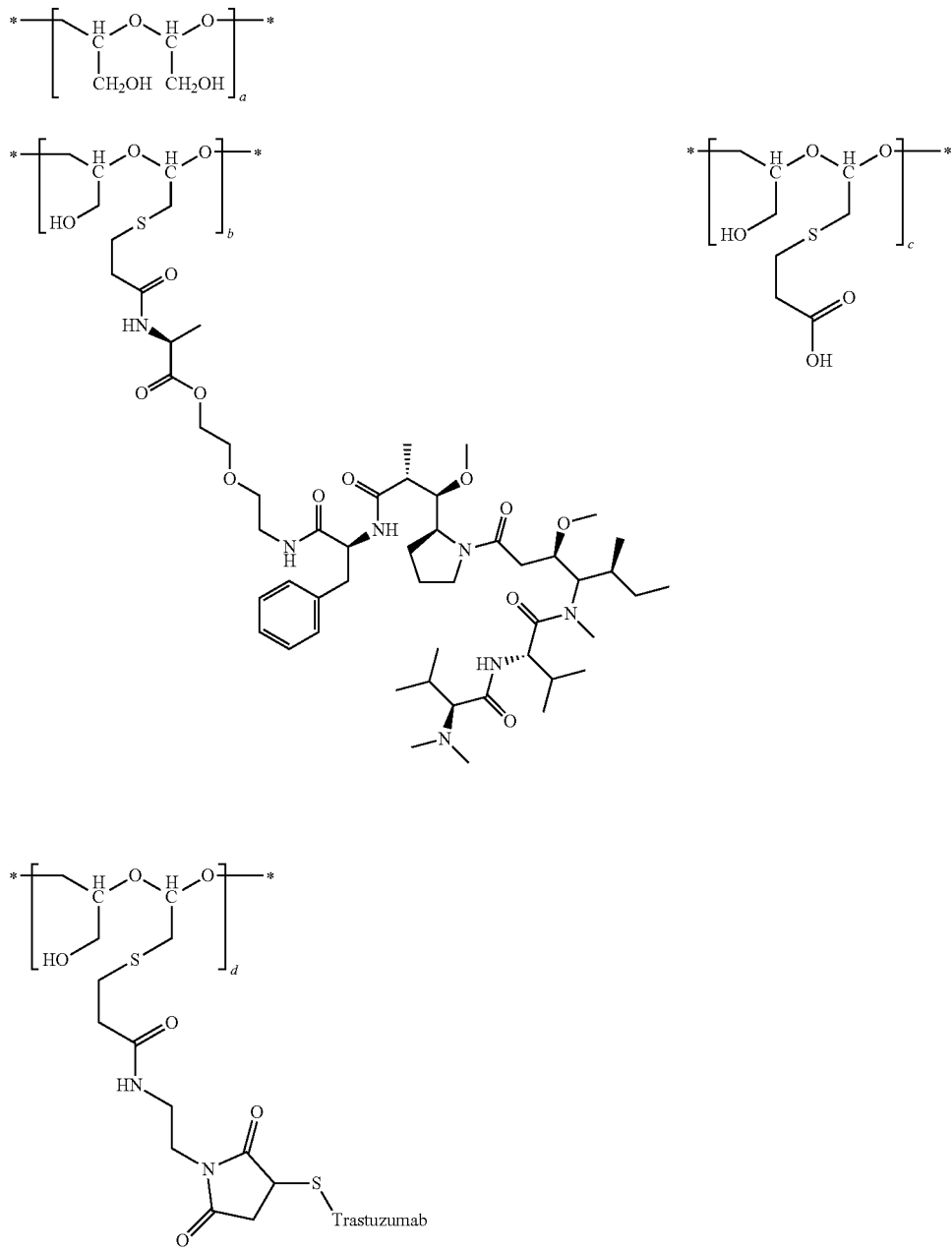

Tris(2-carboxyethyl)phosphine hydrochloride (TCEP, 54 µl, 2.0 mM solution in TEAA buffer, pH=7.4) was added into a solution of Trastuzumab (3 mg) in TEAA buffer (400 µl pH=7.4), and the solution was incubated at 37° C. for one hour. A solution of poly(1-hydroxymethylethylene hydroxy-methyl formal)-SPA-(auristatin F 2-(2-hydroxy-ethoxy)-ethylamide L-Alanine)-maleimide (compound 14, 912 µg) in deionized water (45.6 µl) was added, and the solution was incubated at 25° C. for 6 hours. The product was purified by size-exclusion chromatography using Superose-6 column (eluant: PBS buffer, pH=7.0) to give poly(1-hydroxymethylethylene hydroxy-methyl formal)-SPA-(auristatin F 2-(2-hydroxy-ethoxy)-ethylamide L-Alanine)-Trastuzumab (compound 17). HPLC analysis determined molar ratio of auristatin F to Trastuzumab is about 12:1 to 15:1.

Example 15

Synthesis of 2,5-dioxopyrrolidin-1-yl 3-(2-(2-(3-(2,5-dioxo-2,5-dihydro-1H-pyrrol-1-yl)propanamido)ethoxy)ethoxy)propanoate (Compound 18)

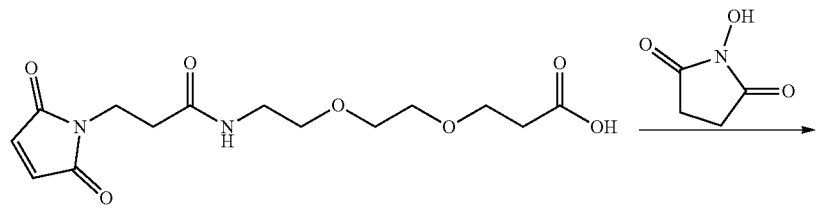

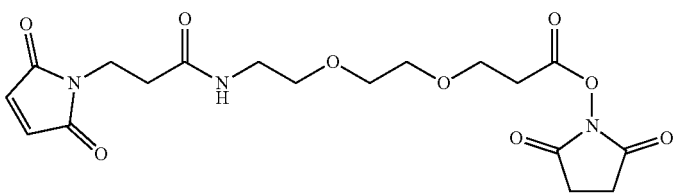

18 I

N-hydroxysuccinimide (105.2 mg, 0.914 mmol) was added into a solution of 3-(2-(2-(3-(2,5-dioxo-2,5-dihydro-1H-pyrrol-1-yl)propanamido)ethoxy)ethoxy)propanoic acid (300 mg, 0.914 mmol) in 5 ml anhydrous dichloromethane at room temperature, followed by the addition of N,N'-dicyclohexylcarbodiimide (198 mg, 0.96 mmol). The reaction mixture was stirred for 2 hours at room temperature. The white solid formed was filtered and the filtrate was concentrated under vacuum to give the crude product (compound 18, 346 mg) which was used directly in the next step.

Example 16

Synthesis of tert-butyl (16-(2,5-dioxo-2,5-dihydro-1H-pyrrol-1-yl)-4,14-dioxo-7,10-dioxa-3,13-diazahexadecyl)carbamate (Compound 19)

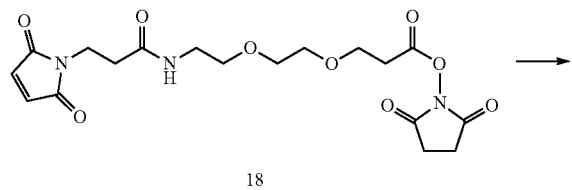

18

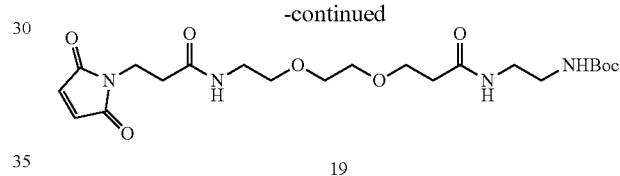

19 tert-Butyl (2-aminoethyl)carbamate (139.5 mg, 0.138 ml, 0.871 mmol) was added into a solution of 2,5-dioxopyrrolidin-1-yl 3-(2-(2-(3-(2,5-dioxo-2,5-dihydro-1H-pyrrol-1-yl)propanamido)ethoxy)ethoxy)propanoate (compound 18) in 4 ml anhydrous acetonitrile at room temperature, followed by the addition of triethyl amine (88.1 mg, 0.121 ml, 0.871 mmol).

The reaction mixture was stirred at room temperature for 16 hours. The mixture was filtered and the filtrate was concentrated under vacuum to give a light yellow oil (compound 19).

Example 17

Synthesis of N-(2-aminoethyl)-3-(2-(2-(3-(2,5-dioxo-2,5-dihydro-1H-pyrrol-1-yl)propanamido)ethoxy)ethoxy)propanamide (Compound 20)

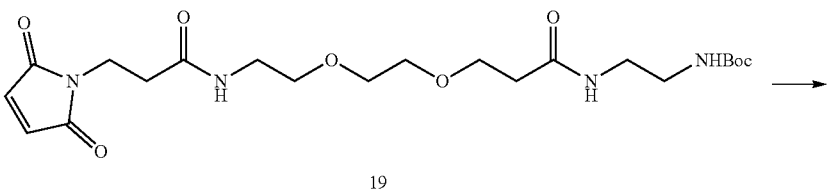

19

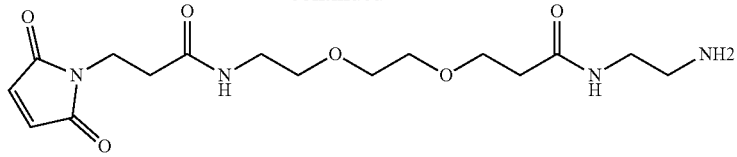

20

Trifluoroacetic acid (1.0 ml) was added dropwise into a solution of tert-butyl (16-(2,5-dioxo-2,5-dihydro-1H-pyrrol-1-yl)-4,14-dioxo-7,10-dioxa-3,13-diazahexadecyl)carbamate (compound 19) in dichloromethane (3.0 ml) and the reaction solution was stirred for 2 hours at room temperature. The reaction mixture was concentrated in vacuo, and the residue was purified by reverse-phase preparatory HPLC to afford N-(2-aminoethyl)-3-(2-(2-(3-(2,5-dioxo-2,5-dihydro-1H-pyrrol-1-yl)propanamido)ethoxy)ethoxy)propanamide (compound 20, TFA salt) as a colorless oil. Mass calculated for $C_{16}H_{26}N_4O_6$+H, $[M+H]^+$ 371.19, observed LC/MS (ESI) m/z 371.43 $[M+H]^+$.

N-Hydroxysuccinimide (2.2 mg, 0.019 mmol) was added into a solution of poly(1-hydroxymethylethylene hydroxymethyl formal)-SPA (compound 8, 30 mg, 3-sulfanylpropionic acid content: 10.7%) in deionized water (2 ml) at 20° C. N-(2-aminoethyl)-3-(2-(2-(3-(2,5-dioxo-2,5-dihydro-1H-pyrrol-1-yl)propanamido)ethoxy)ethoxy)propanamide. TFA (9.0 mg, 0.019 mmol) was added into the reaction solution at 20° C. The pH of reaction mixture was adjusted to 6 using 0.05 N NaOH solution. EDC.HCl (4.5 mg, 0.024 mmol) was added and the reaction solution was stirred 20° C. for 40 min. After 40 min, EDC.HCl (4.5 mg, 0.024 mmol) was added again and the reaction solution was stirred for 18 hours. The reaction mixture was filtered and the filtrate was desalted by diafiltration, using Amicon Ultra-15 centrifugal filter (MWCO: 3K). The desalted solution was lyophilized to give poly(1-hydroxymethylethylene hydroxy-methyl formal)-SPA-maleimide as a colorless solid (33 mg, compound 21). 1H NMR (400 MHz, $D_2O$) shows the maleimide group: δ ppm 6.76 (s, 2H). The maleimide content was found to be 2.9%, as determined by NMR.

Example 18

Synthesis of poly(1-hydroxymethylethylene hydroxy-methyl formal)-SPA-maleimide (Compound 21)

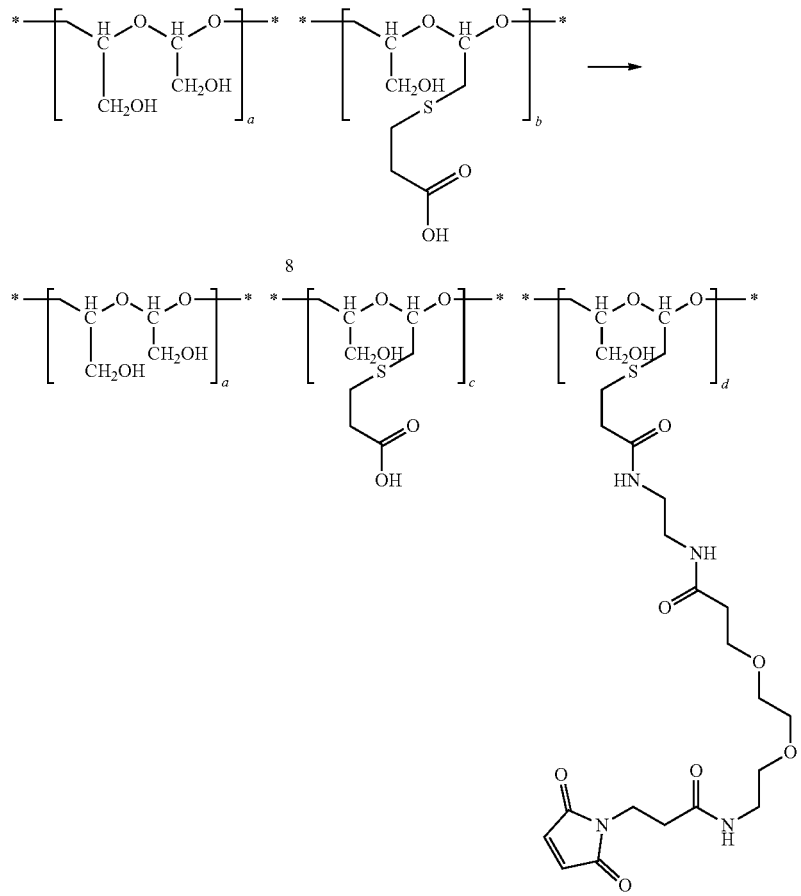

Example 19
Synthesis of poly(1-hydroxymethylethylene hydroxy-methyl formal)-SPA-(auristatin F 2-(2-hydroxy-ethoxy)-ethylamide L-Alanine)-maleimide (Compound 22)
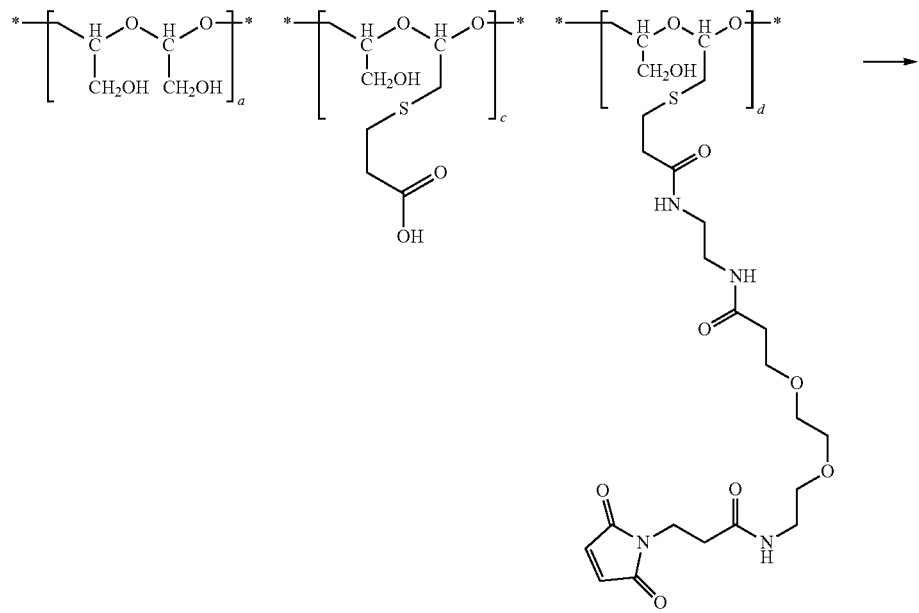
21
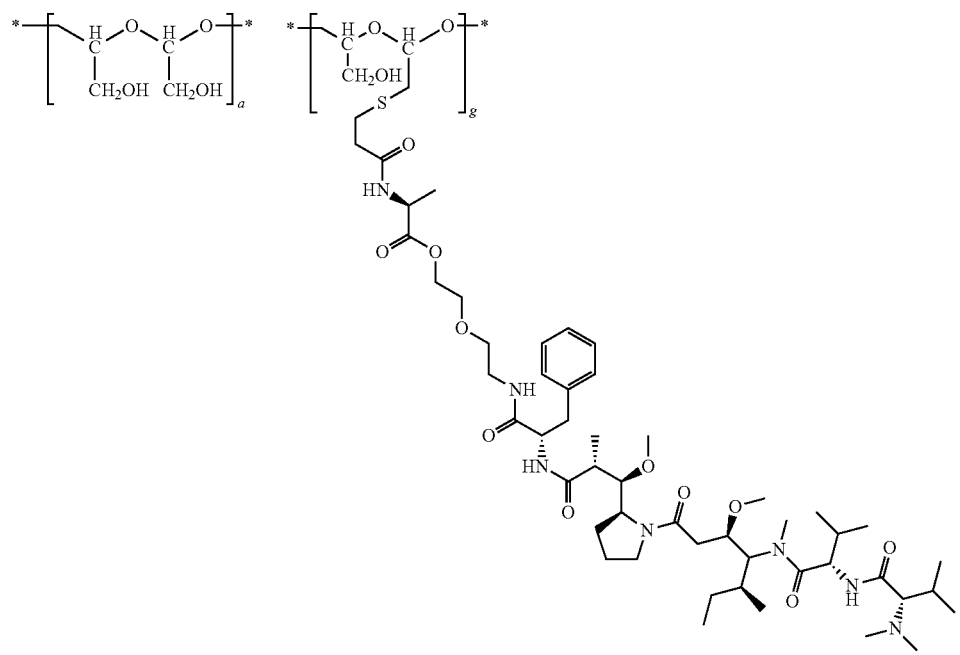

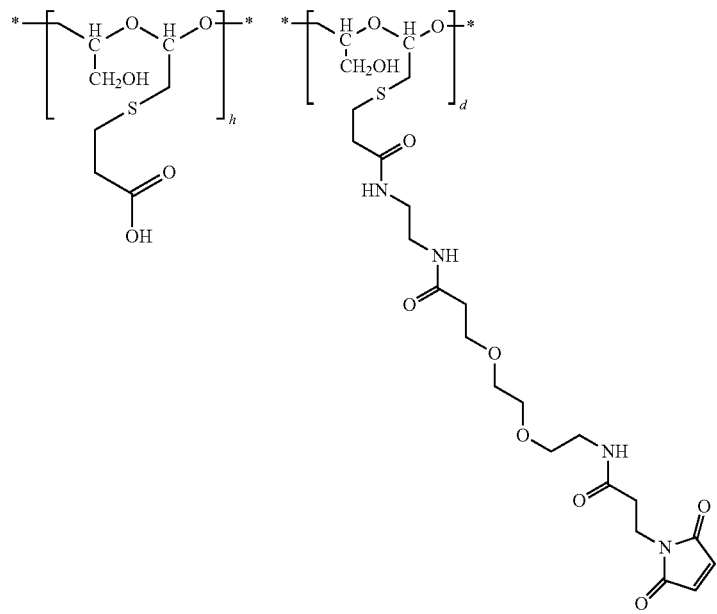

22

N-Hydroxysuccinimide (2.0 mg, 0.014 mmol) was added into a solution of poly(1-hydroxymethylethylene hydroxy-methyl formal)-SPA-maleimide (compound 21, 16 mg, 3-sulfanylpropionic acid content: 7.8%, maleimide content: 2.9%) in deionized water (1.0 ml) at 10° C. Auristatin F 2-(2-hydroxy-ethoxy)-ethylamide L-Alanine (TFA salt, 14 mg) was added into the reaction solution at 10° C. The pH of reaction mixture was adjusted to 6 using 0.05N NaOH solution. EDC.HCl (4 mg, 0.021 mmol) was added and the reaction solution was stirred 20° C. for 40 min. EDC.HCl (4 mg, 0.021 mmol) was added again to the solution and the solution was then stirred for 18 hours. The reaction mixture was filtered and the filtrate was desalted by diafiltration, using Amicon Ultra-15 centrifugal filter (MWCO: 3K). The desalted solution was lyophilized to give the product as a white solid (compound 22, 18 mg). 1H NMR (400 MHz, $D_2O$) shows the phenyl group on auristatin F: δ ppm 7.16-7.26 (m, 5H). The auristatin F 2-(2-hydroxy-ethoxy)-ethylamide L-Alanine content was found to be 7%, as determined by NMR.

Example 20

Synthesis of poly(1-hydroxymethylethylene hydroxy-methyl formal)-SPA-maleimide (Compound 23)

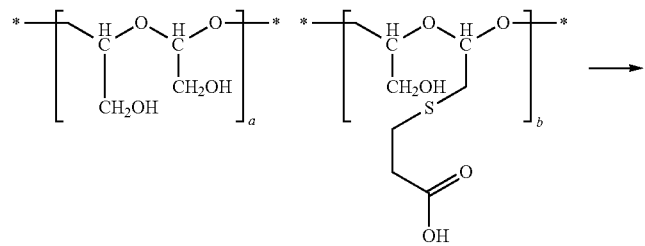

8

-continued

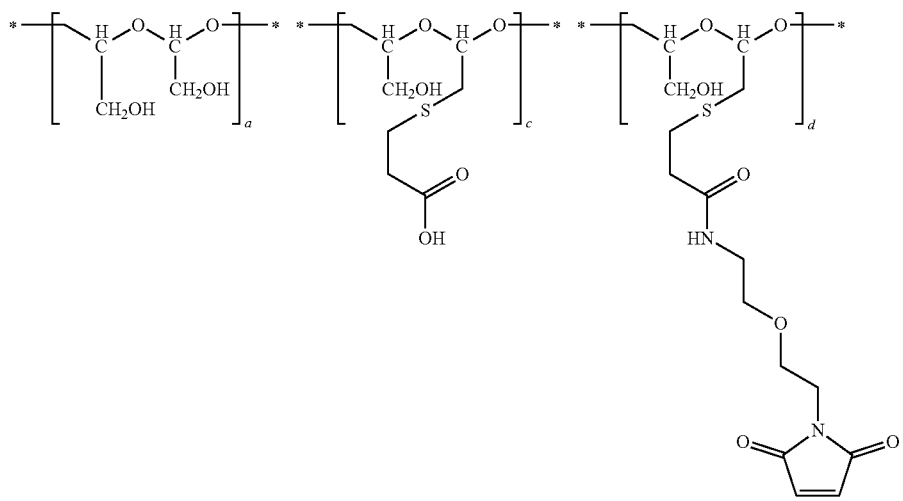

23

N-Hydroxysuccinimide (10 mg, 0.090 mmol) was added into a solution of poly(1-hydroxymethylethylene hydroxymethyl formal)-SPA (compound 8, 86 mg, 3-sulfanylpropionic acid content: 21%) in deionized water (3.0 ml) at 20° C. 1-[2-(2-Aminoethoxy)-ethyl]maleimide-HCl (20.0 mg, 0.090 mmol) was added into the reaction solution at 20° C. The pH of reaction mixture was adjusted to 6 using 0.05 N NaOH solution. EDC.HCl (17.5 mg, 0.090 mmol) was added and the reaction solution was stirred 20° C. for 40 min. EDC.HCl (17.5 mg, 0.090 mmol) was added again to the reaction mixture which was then stirred for 18 hours. The reaction mixture was filtered and the filtrate was desalted by diafiltration, using Amicon Ultra-15 centrifugal filter (MWCO: 3K). The desalted solution was lyophilized to give poly(1-hydroxymethylethylene hydroxy-methyl formal)-SPA-maleimide (compound 23, 89 mg) as a colorless solid. 1H NMR (400 MHz, D$_2$O) shows the maleimide group: δ ppm 6.76 (s, 2H). The maleimide content was found to be 5.8%, as determined by NMR.

Example 21

Synthesis of poly(1-hydroxymethylethylene hydroxy-methyl formal)-SPA-(auristatin F 2-(2-hydroxy-ethoxy)-ethylamide L-Alanine)-maleimide (Compound 24)

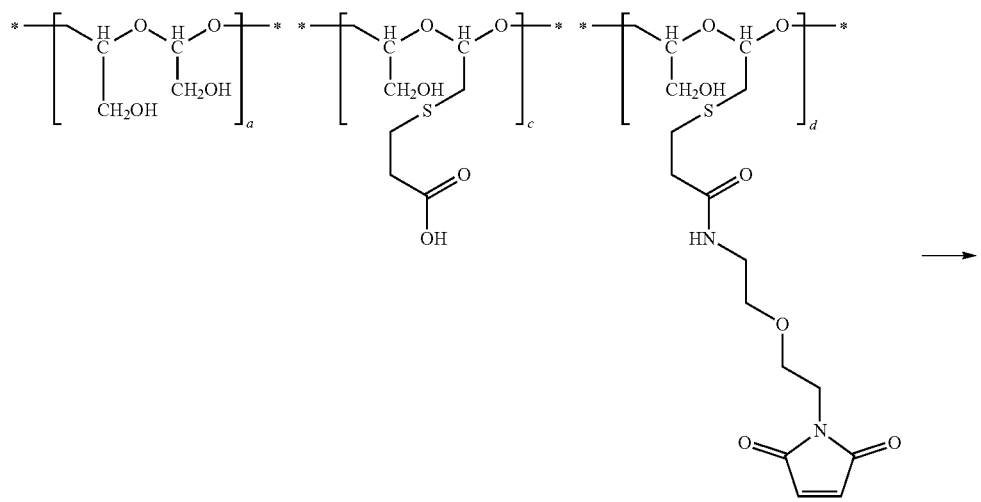

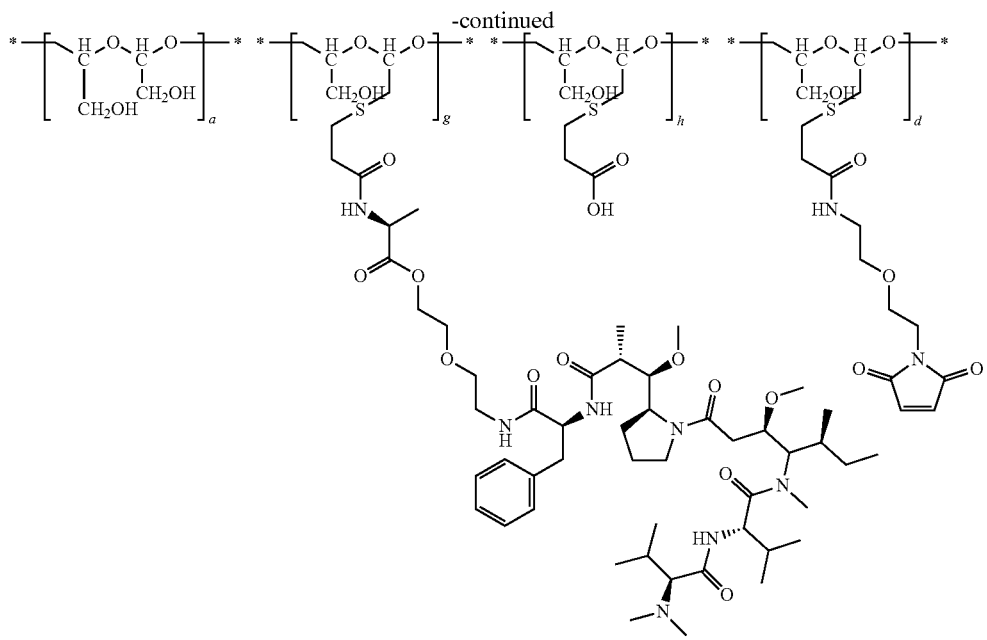

24

N-Hydroxysuccinimide (9.4 mg, 0.066 mmol) was added into a solution of poly(1-hydroxymethylethylene hydroxy-methyl formal)-SPA-maleimide (75 mg, 3-sulfanylpropionic acid content: 15.2%, maleimide content: 5.8%) in deionized water (4.5 ml) at 10° C. Auristatin F 2-(2-hydroxy-ethoxy)-ethylamide L-Alanine (TFA salt, 66 mg, 0.065 mmol) was added into the reaction solution at 10° C. The pH of reaction mixture was adjusted to 6 using 0.05 N NaOH solution. EDC.HCl (19 mg, 0.099 mmol) was added and the reaction solution was stirred 20° C. for 40 min. EDC.HCl (19 mg, 0.099 mmol) was added a second time to the reaction solution which was then stirred for 18 hours. The reaction mixture was filtered and the filtrate was desalted by diafiltration, using Amicon Ultra-15 centrifugal filter (MWCO: 3K). The desalted solution was lyophilized to give the product as a white solid (68 mg). 1H NMR (400 MHz, D$_2$O) shows the phenyl group on auristatin F: δ ppm 7.18-7.26 (m, 5H). The auristatin F 2-(2-hydroxy-ethoxy)-ethylamide L-Alanine (compound 24) content was found to be 7.7%, as determined by NMR.

Example 22

Preparation of poly(1-hydroxymethylethylene hydroxy-methyl formal)-SPA-(auristatin F 2-(2-hydroxy-ethoxy)-ethylamide L-Alanine)-Trastuzumab (Compound 25)

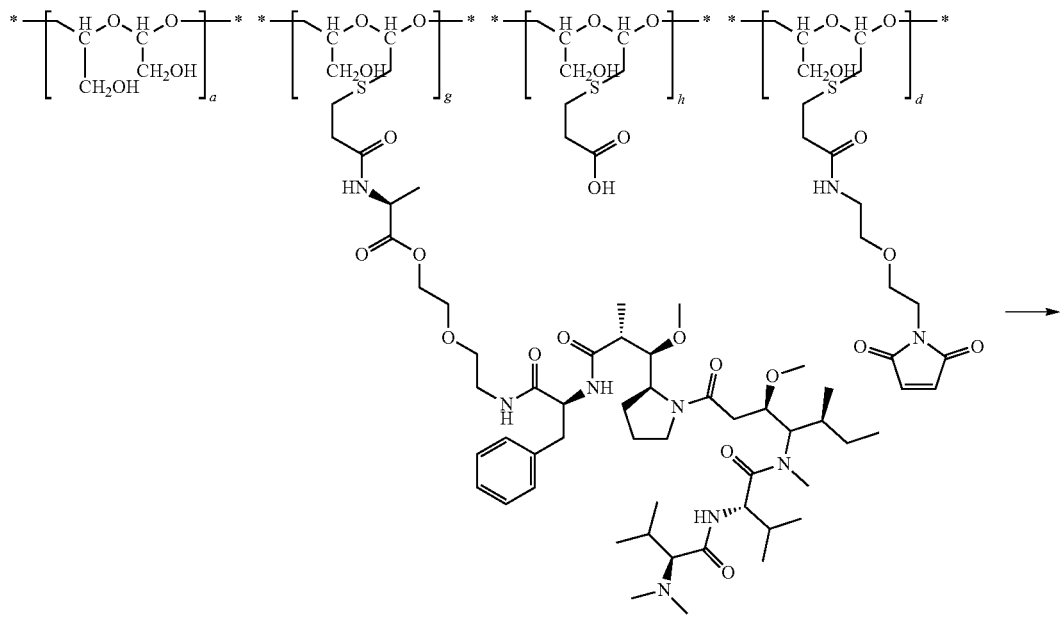

24

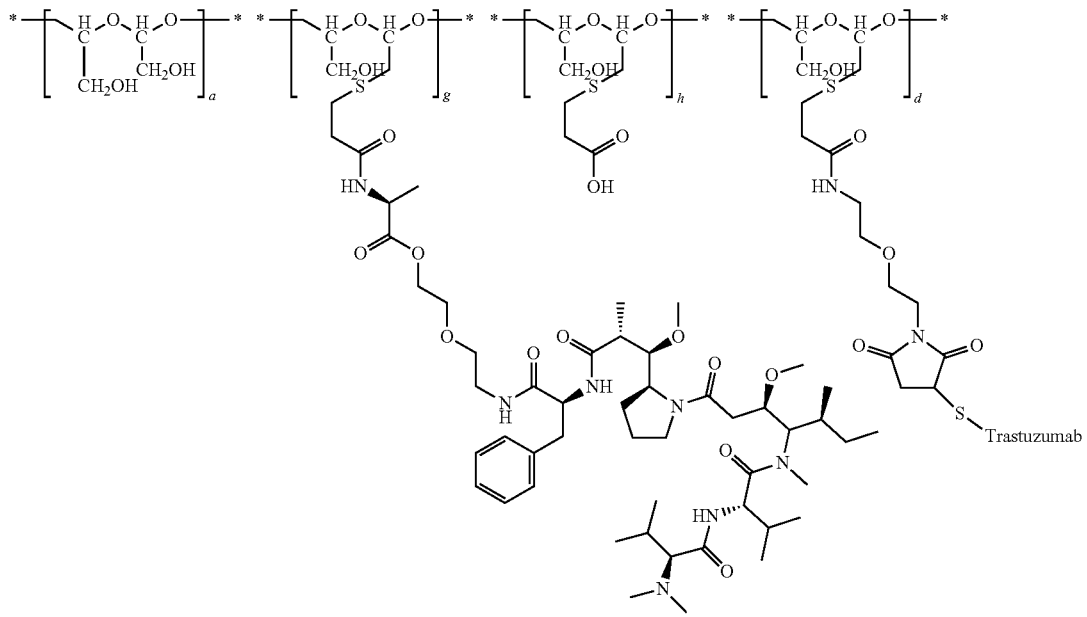

25

Tris(2-carboxyethyl)phosphine hydrochloride (TCEP, 510 μl, 1.02 μmol, 2.0 mM solution in TEAA, pH=7.4) was added into a solution of Trastuzumab (30 mg, 0.2895 μmol) in TEAA buffer (1.5 ml, pH=7.4) under Ar, and the solution was incubated at 37° C. for two hours. The reaction mixture was cooled to 0° C. The partially reduced Trastuzumab solution was added into a solution of poly(1-hydroxymethylethylene hydroxy-methyl formal)-SPA-(auristatin F 2-(2-hydroxy-ethoxy)-ethylamide L-Alanine)-maleimide (compound 24, 37.5 mg) in deionized water (1.5 ml) at 0° C. The solution was stirred at 0° C. for 30 min, then warmed to room temperature and stirred for 4 hours. The reaction was quenched with an aqueous solution of cysteine hydrochloride (21 mg). The reaction mixture was stirred at room temperature for one hour. The product was purified by size-exclusion chromatography using Superose-6 column (eluant: PBS buffer, pH=7.0) to give poly(1-hydroxymethylethylene hydroxy-methyl formal)-SPA-(auristatin F 2-(2-hydroxy-ethoxy)-ethylamide L-Alanine)-Trastuzumab (compound 25). Average ratio of auristatin F to Trastuzumab is about 8.

Example 23

Synthesis of (S)-tert-butyl (4,11-diethyl-4-hydroxy-3,14-dioxo-3,4,12,14-tetrahydro-1H-pyrano[3',4':7]indolizino[1,2-b]quinolin-9-yl) carbonate (Compound 26)

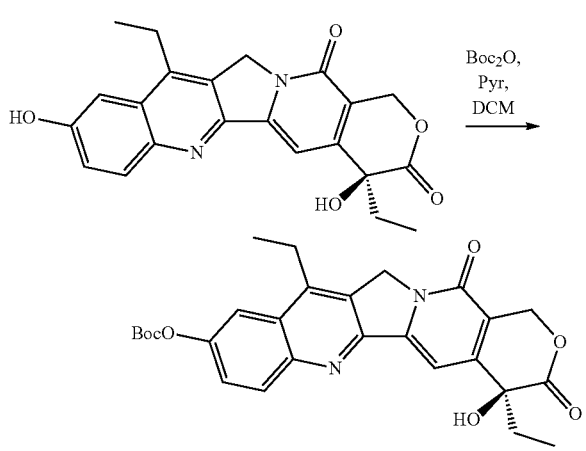

26

Di-tert-butyl dicarbonate (144 mg, 0.629 mol) was added into a suspension of 7-ethyl-10-hydroxy-camptothecin (SN-38, 190 mg, 0.484 mmol) in 19 mL of anhydrous dichloromethane, followed by the addition of anhydrous pyridine (1.157 mL, 14.365 mmol). The reaction suspension was stirred overnight at room temperature. The suspension was filtered and the filtrate was extracted with 0.5 N HCl (3×12 mL) and saturated NaHCO$_3$ (1×12 mL). The organic phase was dried overMgSO$_4$, filtered and evaporated under vacuum to give a pale yellow solid (compound 26, 232 mg, yield: 97.3%).

Example 24

Synthesis of tert-butyl (s)-(2-(2-(2-((((9-((tert-butoxycarbonyl)oxy)-4,11-diethyl-3,14-dioxo-3,4,12,14-tetrahydro-1H-pyrano[3',4':6,7]indolizino[1,2-b]quinolin-4-yl)oxy)carbonyl)oxy)ethoxy)ethoxy)ethyl)carbamate (Compound 27)

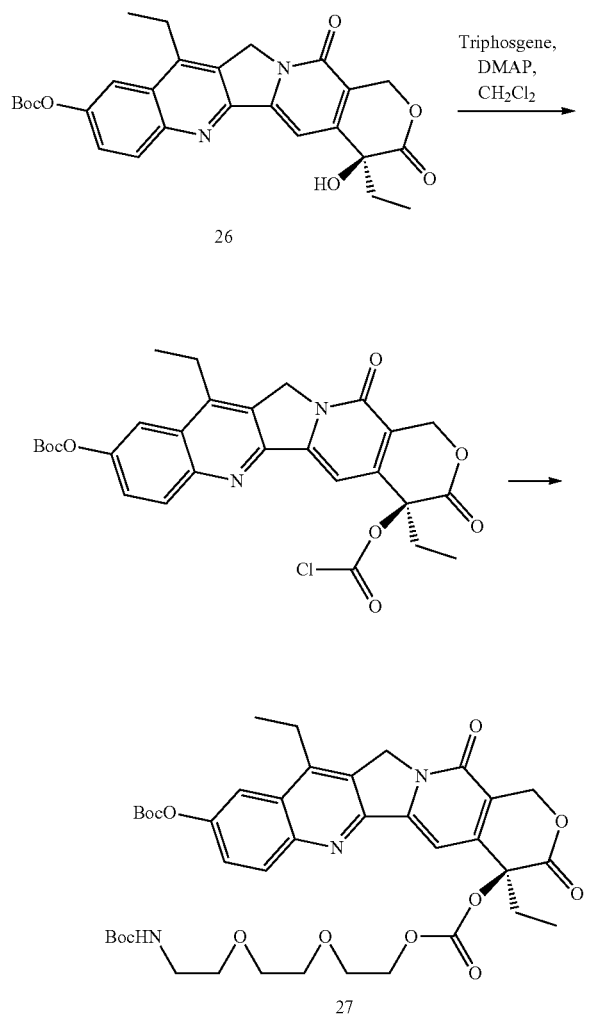

(S)-Tert-Butyl-4,11-Diethyl-4-Hydroxy-3,14-Dioxo-3,4,12,14-Tetrahydro-1H-pyrano[3',4',6,7]indolizino[1,2-b]quinolin-9-yl) carbonate (compound 29, 0.232 g, 0.471 mmol), DMAP (0.173 g, 1.413 mmol), and triphosgene (0.061 g, 0,207 mmol) were added into a round bottomed flask, followed by the addition of dichloromethane (1.0 mL), The reaction mixture was stirred for a few minutes and monitored by TLC. 2-[2-(2-Boc-aminoethoxy)ethoxy]ethanol (0.143 g, 0.575 mmol) was added into the above solution. The reaction mixture was stirred for 5 min, and then purified by flash chromatography using ethyl acetate to give compound 27 (279 mg, yiele: 77%). Mass calculated for C$_{39}$H$_{49}$N$_3$O$_{13}$+H, [M+H]$^+$ 768.3, observed LC/MS (ESI) m/z 768.2 [M+H]$^-$, 790.2 [M+Na]$^+$.

Example 25

Synthesis of (S)-2-(2-(2-aminoethoxy)ethoxy)ethyl (4,11-diethyl-9-hydroxy-3,14-dioxo-3,4,12,14-tetrahydro-1H-pyrano[3',4':6,7]indolizino[1,2-b]quinolin-4-yl) carbonate (Compound 28)

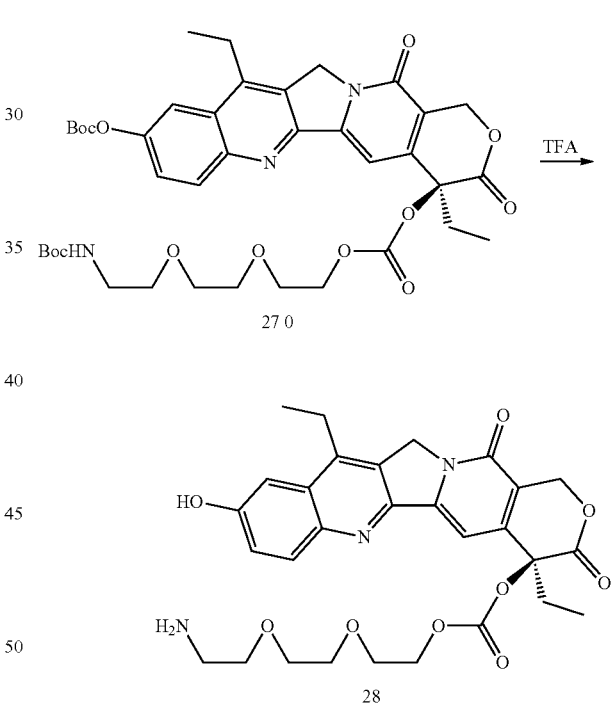

tert-Butyl (S)-(2-(2-(2-((((9-((tert-butoxycarbonyl)oxy)-4,11-diethyl-3,14-dioxo-3,4,12,14-tetrahydro-1H-pyrano[3',4':6,7]indolizino[1,2-b]quinolin-4-yl)oxy)carbonyl)oxy)ethoxy)ethoxy)ethyl)carbamate (compound 27, 123 mg, 0.16 mmol) was dissolved in 0.4 mL TFA and stirred for 5 min at room temperature. To the reaction solution was added 4 mL diethyl ether and the mixture was stirred for 5 min. The suspension was filtered and the solid was collected, and lyophilized to give compound 28 (82 mg). Mass calculated for C$_{29}$H$_{33}$N$_3$O$_9$, [M+H]$^+$ 568.2, observed LC/MS (ESI) m/z 568.2 [M+H]$^+$, 590.2 [M+Na]$^+$.

Example 26

Synthesis of poly(1-hydroxymethylethylene hydroxy-methyl formal)-SPA-(7-ethyl-10-hydroxy-camptothecin)-maleimide (Compound 29)

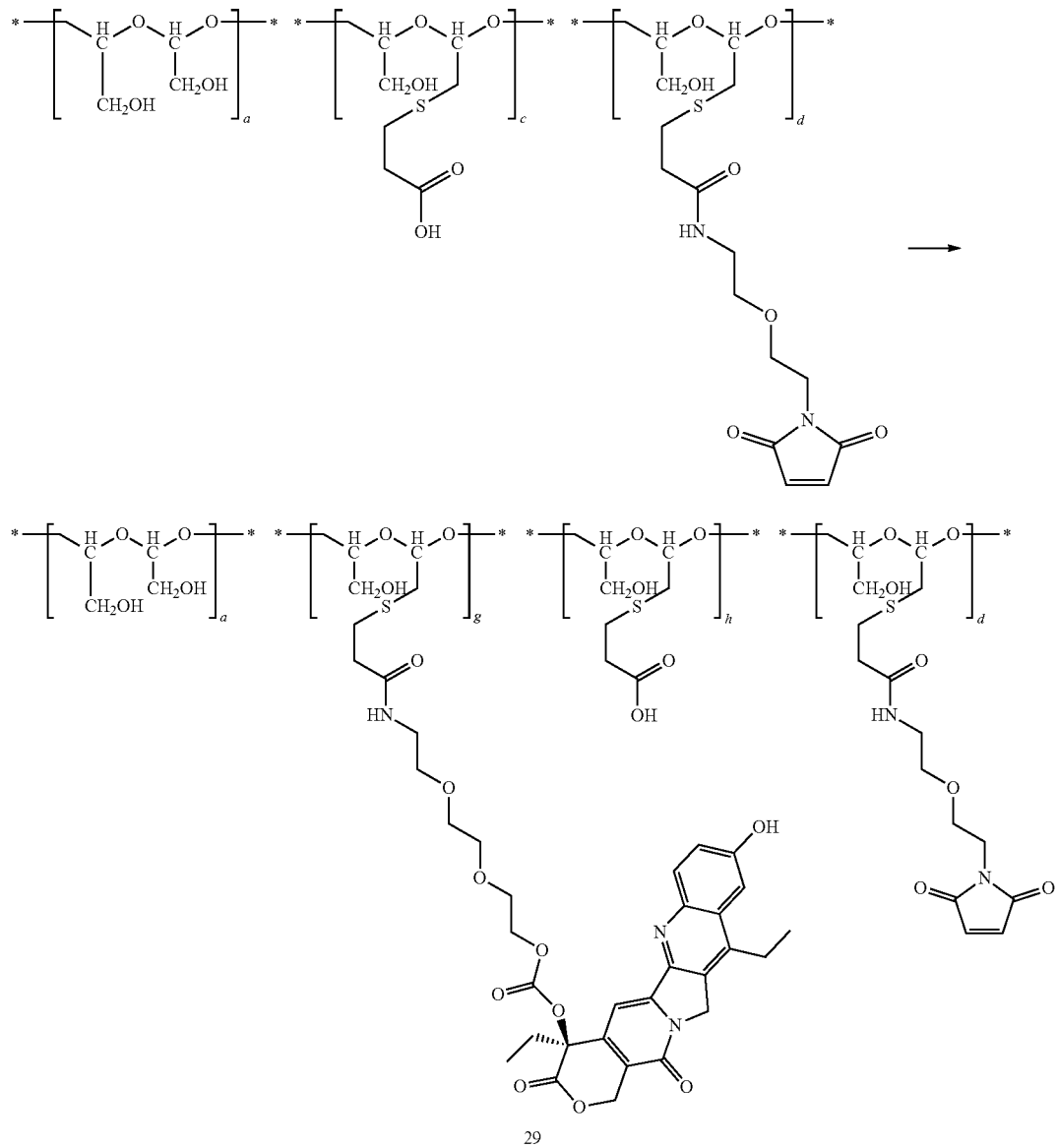

N-Hydroxysuccinimide (4 mg, 0.033 mmol) was added into a solution of poly(1-hydroxymethylethylene hydroxy-methyl formal)-SPA-maleimide (compound 8, 50 mg, 3-sulfanylpropionic acid content: 27.6%, maleimide content: 3%, 10 K poly(1-hydroxymethylethylene hydroxy-methyl formal)) in deionized water (1.0 ml) at 20° C. (S)-2-(2-(2-aminoethoxy)ethoxy)ethyl (4,11-diethyl-9-hydroxy-3,14-dioxo-3,4,12,14-tetrahydro-1H-pyrano[3',4':6,7]indolizino[1,2-b]quinolin-4-yl) carbonate (compound 28, TFA salt, 24 mg, 0.036 mmol) was added into the reaction solution at 20° C. The resulting mixture was cooled to 5-10° C., and the pH of reaction mixture was adjusted to 6 using 0.05 N NaOH solution. EDC.HCl (11 mg, 0.054 mmol) was added and the reaction solution was stirred at 5-10° C. for 40 min. EDC.HCl (11 mg, 0.054 mmol) was added a second time to the reaction solution and the solution was stirred for 18 hours at 20° C. The reaction mixture was filtered and the filtrate was desalted by diafiltration, using Amicon Ultra-15 centrifugal filter (MWCO: 3K). The desalted solution was lyophilized to give the product (44 mg). 1H NMR (400 MHz, $D_2O$) shows the aromatic hydrogen on camptothecin: δ ppm 7.41, 6.94. The camptothecin content was found to be 8%, as determined by NMR.

Example 27

Preparation of poly(1-hydroxymethylethylene hydroxy-methyl formal)-SPA-(7-ethyl-10-hydroxy-camptothecin)-Trastuzumab (Compound 30)

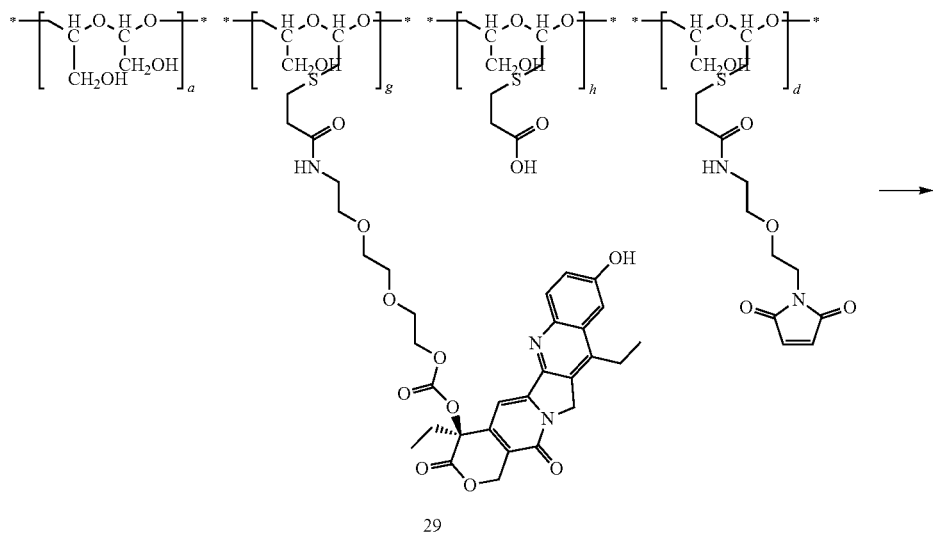

29

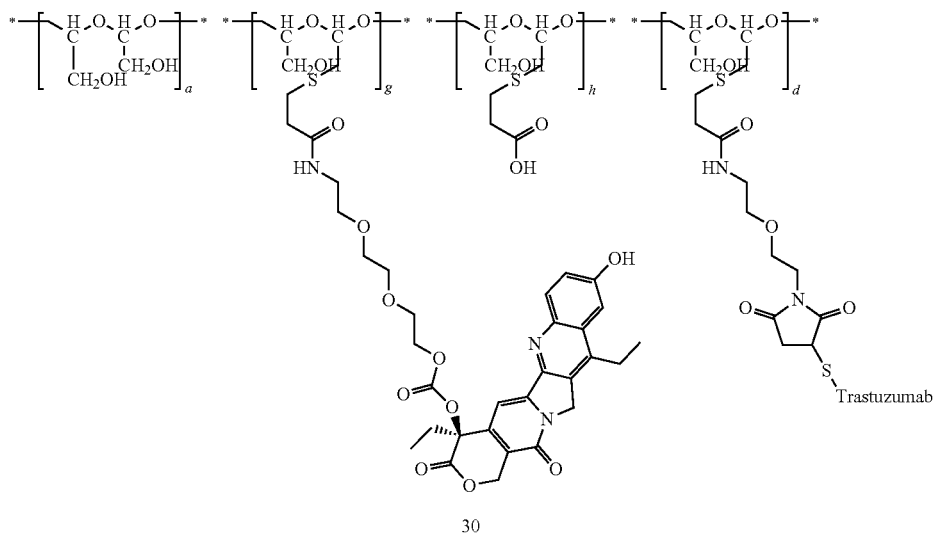

30

Tris(2-carboxyethyl)phosphine hydrochloride (TCEP, 120 μl, 0.241 μmol, 2.0 mM solution in TEAA, pH=7.4) was added into a solution of Trastuzumab (10 mg, 0.0687 μmol) in TEAA buffer (0.5 ml, pH=7.4) under Ar, and the solution was incubated at 37° C. for two hours. The reaction mixture was cooled to 0° C. The partially reduced Trastuzumab solution was added into a solution of poly(1-hydroxymethylethylene hydroxy-methyl formal)-SPA-(7-ethyl-10-hydroxy-camptothecin)-maleimide (compound 29, 19.0 mg) in deionized water (1.14 ml) and DMF (50 μl) at 0° C. The solution was stirred at 0° C. for 30 min, then warmed to room temperature and stirred for 4 hours. The reaction was quenched with an aqueous solution of cysteine hydrochloride (7 mg). The reaction mixture was stirred at room temperature for one hour. The product was purified by size-exclusion chromatography using Superose-6 column (eluant: PBS buffer, pH=7.0) to give poly(1-hydroxymethylethylene hydroxy-methyl formal)-SPA-(7-ethyl-10-hydroxy-camptothecin)-Trastuzumab (compound 30). Average ratio of 7-ethyl-10-hydroxy-camptothecin to Trastuzumab is about 16.

Example 28

Cell Viability Assay

Compounds and conjugates were tested for their activity using the Cell Viability Assay (CellTiter-Glo® Luminescent Cell Viability Assay from Promega), which measures the number of viable cells in culture after treatment with the inventive compounds or conjugates for 72 hours based on quantitation of the ATP present (Cell Viability. $IC_{50}$).

Three HER2 expressing breast cancer cell lines (BT474, HCC1954 and SK-BR-3) and HER2 expressing gastric cancer cell line NCI-N87 were used in the viability assay. The cells were placed in opaque-walled 96-well plate and allowed to adhere overnight at 37° C. in 5% CO$_2$ and 95% humidity atmosphere. Cell density per well: 7000 (BT474), 3000 (HCC1954), 5000 (NCI-N87), 4000 (SK-BR-3). The test compounds or conjugates were added to experimental wells, and incubate at 37° C. in 5% CO$_2$ and 95% humidity atmosphere for 72 hours. The plates were equilibrated at room temperature for 30 min. CellTiter-Glo® reagent equal to the volume of cell culture medium present in each well was added. After cell lysis on an orbital shaker for 2 min, the plate was incubated at room temperature for 10 min. Luminescence were recorded using EnVision® Multilabel Reader (PerkinElmer, 2104-0010A). GraphPad Prism 5.0 was used to analyze the data. The dose response curves were determined, and the IC$_{50}$ value was calculated.

Figure 2:
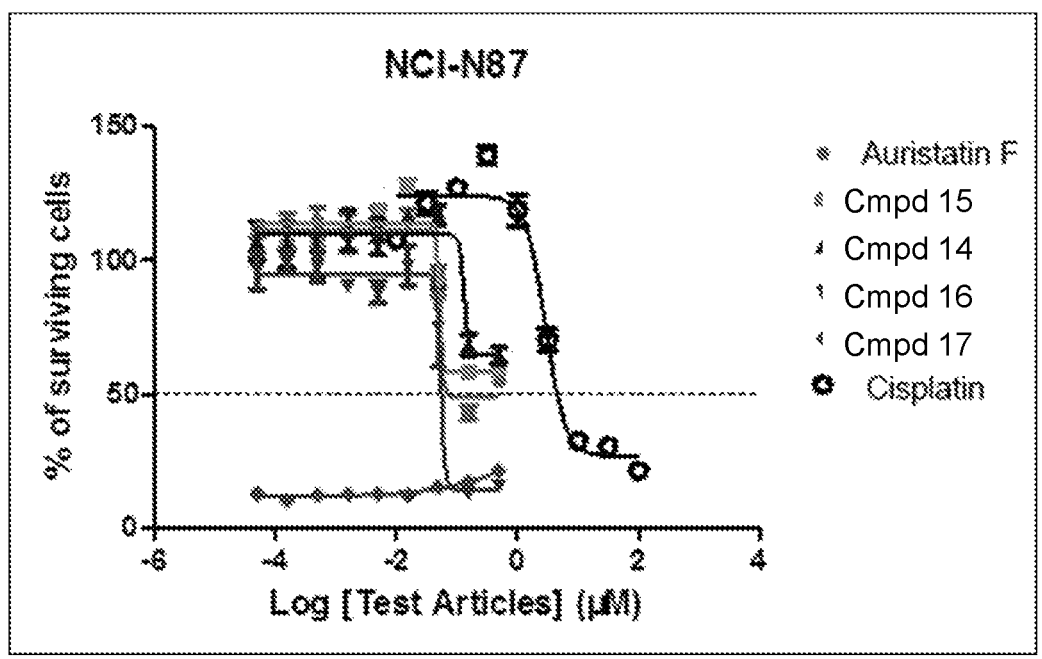
FIG. 2 depicts a dose response curve of the % surviving NCI-N87 cells treated with Auristatin F, Compounds 14-17 and Cisplatin.

Table 1 provides IC$_{50}$ data for Compounds 14-17 in the above cell lines with Auristatin F and Cisplatin as controls. See FIGS. 1-4

TABLE 1

| Cell Lines | IC$_{50}$ (nM) | | | | | |
| --- | --- | --- | --- | --- | --- | --- |
| | Auristatin F | Cmpd 15 | Cmpd 14 | Cmpd 16 | Cmpd 17 | Cisplatin |
| HCC1954 | 38.2 | 23.9 | 32.2 | 0.13 | <0.05 | 6051.8 |
| NCI-N87 | 69.8 | >500 | >500 | 55.6 | <0.05 | 4564.7 |
| SK-BR-3 | 51 | 37 | 48 | 22 | <0.05 | 1919 |
| BT-474 | 264.1 | 57.4 | 87.9 | 0.39 | <0.05 | >100000 |

This data demonstrates that a known antineoplastic agent in HER2 cancer cell lines, Auristatin F, is delivered to the cancer cells by the antibody-drug conjugates Compounds 16 and 17. Compounds 14 and 15 lack the antibody Trastuzumab so the Auristatin F is not targeted to the cancer cells. These two compounds have activity similar to free Auristatin F. However, when the antibody is present in Compounds 16 and 17, the inhibition of HER2 increases significantly, demonstrating the effectiveness of the disclosed antibody-drug conjugates in targeting treatment to specific cells.

Another assay measured the IC$_{50}$ values for compounds 24 and 25 on the same cell lines and MCF7 breast cancer cell. Table 2 provides IC$_{50}$ data for Compounds 24 and 25 in the above cell lines with Auristatin F, Trastuzumab and Cisplatin as controls. Compound 25 shows a significant increase in activity as compared to compound 24 which does not comprise a targeting moiety and each of the controls.

TABLE 2

| Cell Lines | IC$_{50}$ (nM) | | | | |
| --- | --- | --- | --- | --- | --- |
| | Auristatin F | Trastuzumab | Cmpd 24 | Cmpd 25 | Cisplatin |
| HCC1954 | 200.3 | 127.7 | 45.9 | 0.2 | 6234.9 |
| NCI-N87 | 386.3 | 69.5 | 91.5 | 0.3 | 1662.2 |
| SK-BR-3 | 232.6 | 122.3 | 56.6 | 0.1 | 870.7 |
| BT-474 | 1543.3 | 266.8 | 58.0 | 0.4 | 38517 |
| MCF7 | 1952.0 | 447.4 | 229.7 | 3.3 | 9151.0 |

The disclosures of each and every patent, patent application, and publication cited herein are hereby incorporated herein by reference in their entirety.

While the disclosure has referenced specific embodiments, it is apparent that other embodiments and variations may be devised by others skilled in the art without departing from the true spirit and scope of the invention. The appended claims are intended to be construed to include all such embodiments and equivalent variations.

The invention claimed is:

1. A compound of Formula (I) comprising blocks of polymerized monomers (a), (b), (d) and optionally (c):

(I)

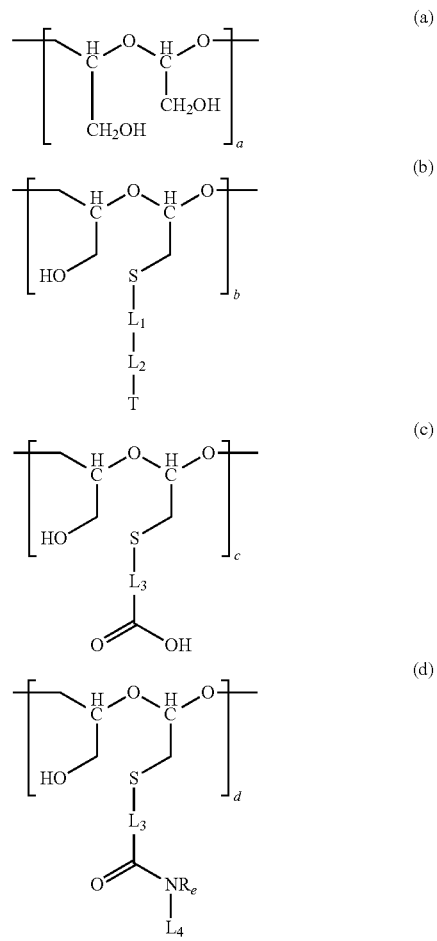

wherein L$_1$ is a linking group selected from alkylene, heteroalkylene, cycloalkylene, heterocyclylene, arylene, heteroarylene, amidoalkylene, amidoheteroalkylene, and any combination thereof;

L$_2$ is absent, or can be of the formula:

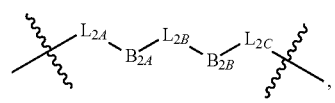

L$_{2A}$ is a linking group selected from alkylene, heteroalkylene, cycloalkylene, heterocyclylene, arylene, heteroarylene, —C(O)—, —NR$_c$—, and any combination thereof;

L$_{2B}$ and L$_{2C}$ are independently absent or a linker group selected from alkylene, heteroalkylene, cycloalkylene, heterocyclylene, arylene, heteroarylene, amidoalkylene, amidoheteroalkylene, —C(O)—, —NR$_c$—, and any combination thereof;

B$_{2A}$ and B$_{2B}$ are independently absent or a cleavable linker;

T is a therapeutic agent selected from the group consisting of chemotherapeutic agents, microtubule inhibitors, DNA-damaging agents and RNA transcription inhibitors;

$L_3$ is a linker group selected from alkylene, heteroalkylene, cycloalkylene, heterocyclylene, arylene, heteroarylene, amidoalkylene, amidoheteroalkylene, and any combination thereof;

$R_e$ is a substituent selected from hydrogen, alkyl and heteroalkyl;

$L_4$ is a group of the formula:

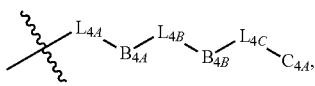

$L_{4A}$ is a linker group selected from alkylene, heteroalkylene, cycloalkylene, heterocyclylene, arylene, heteroarylene, —C(O)—, —NR$_c$—, and any combination thereof;

$L_{4B}$ and $L_{4C}$ are independently absent or a linker group selected from alkylene, heteroalkylene, cycloalkylene, heterocyclylene, arylene, heteroarylene, amidoalkylene, amidoheteroalkylene, —C(O)—, —NR$_c$—, and any combination thereof;

$B_{4A}$ and $B_{4B}$ are independently absent or a cleavable linker;

$C_{4A}$ is a group selected from

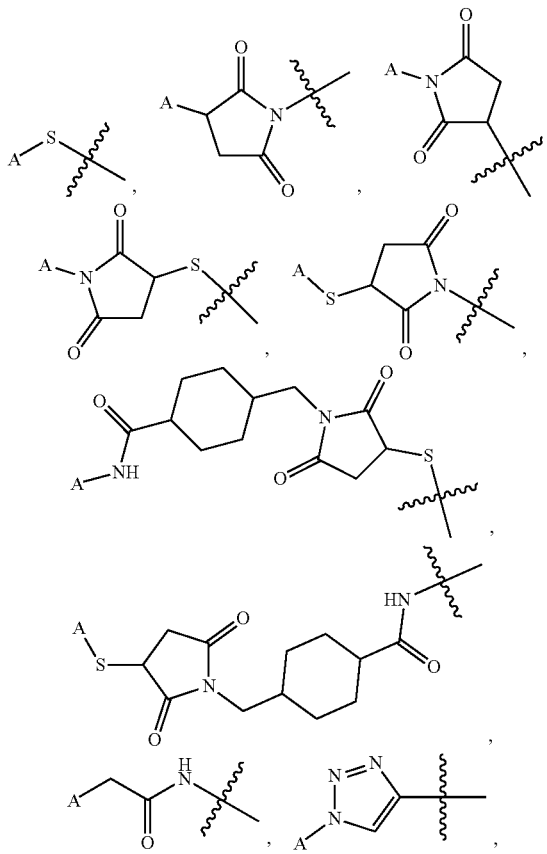

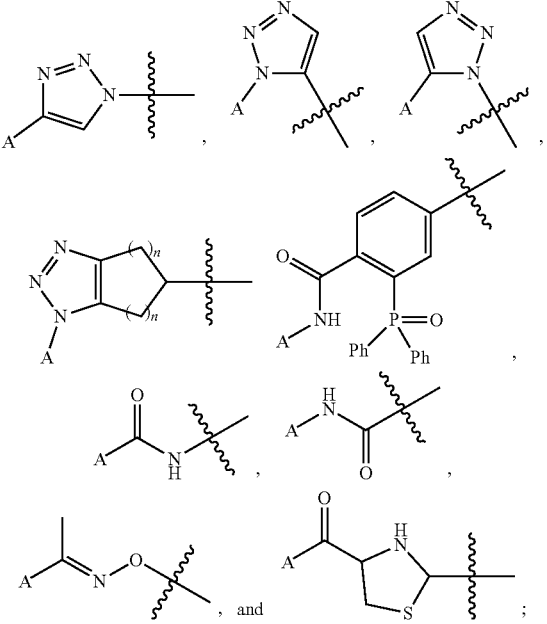

where
- A is —H or a targeting moiety selected from the group consisting of an antibody, a synthetically functionalized antibody, a peptide and a targeting ligand;
- "n" is independently at each occurrence an integer ranging from 0-5;
- $R_c$ and $R_d$ are independently selected at each occurrence from hydrogen, alkyl, heteroalkyl, cycloalkyl, and heterocyclyl;
- each cleavable linker $B_{2A}$, $B_{2B}$, $B_{4A}$ and $B_{4B}$, if present, is independently selected from —S—S—, —C(=O)O—, —OC(=O)—, —C(=O)NR$_c$—, —N(R$_c$)C(=O)—, —OC(=O)O—, —NR$_c$C(=O)O—, —OC(=O)N(R$_c$)— or —N(R$_c$)C(=O)N(R$_d$)—, —C(=O)N(R$_c$)C(=O)—, —C(=O)S—, —SC(=O)—, —SC(=O)S—, —OC(=O)S—, —SC(=O)O—, —OC(=S)O—, —SC(=S)S—, —N(R$_c$)SO$_2$—, —SO$_2$N(R$_c$)—, —N(R$_c$)SO$_2$N(R$_d$)—, —C(=O)N(R$_c$)N(R$_d$)—, —N(R$_c$)N(R$_d$)C(=O)—, —N(R$_c$)N(R$_d$)C(=O)O—, —OC(=O)N(R$_c$)N(R$_d$)—, —C(R$_c$)=N—NH—C(=O)—, —C(=O)NH—N=C(R$_c$)—, —C(R$_c$)=N—O—, —O—N=C(R$_c$)—,

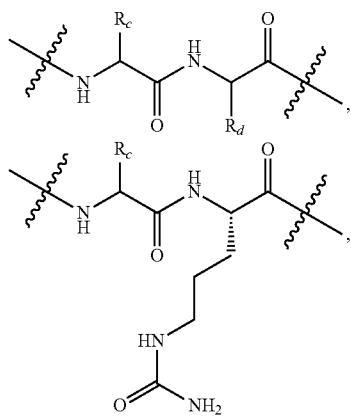

-continued

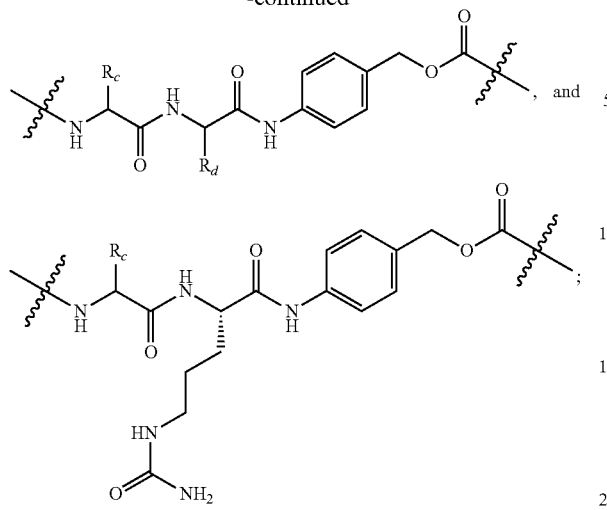

, and

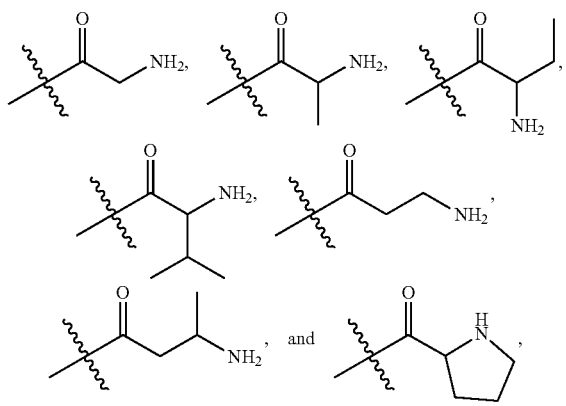

and "p" is an integer from 1-4.

4. The compound of claim 3, wherein $R_f$ comprises the point of attachment of said auristatin derivative to said compound.

5. The compound of claim 3, wherein $R_f$ is hydrogen or

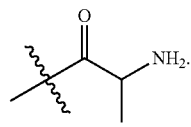

6. The compound of claim 1, wherein said therapeutic agent is a camptothecin derivative having the structure:

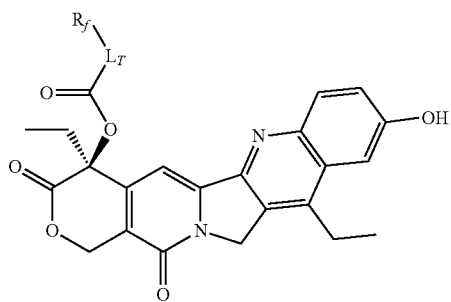

where each monomer is substituted independently from any additional monomer;

"a" is independently at each occurrence an integer from 1-1860;

"b" is independently at each occurrence an integer from 1-372;

"c" is absent or independently at each occurrence an integer from 1-465;

"d" is independently at each occurrence an integer from 1-186; and each block of monomer unit (a), (b), (c), and (d), is covalently attached to at least one block monomer unit (a), (b), (c), and/or (d) and each block of monomer units is independently substituted from any other block of monomer units;

with the proviso that the compound of Formula (I) contains one or more therapeutic agents, T, and one or more targeting moieties A.

2. The compound of claim 1, wherein the therapeutic agent T is a chemotherapeutic agent.

3. The compound of claim 1, wherein the therapeutic agent is an auristatin derivative of structure:

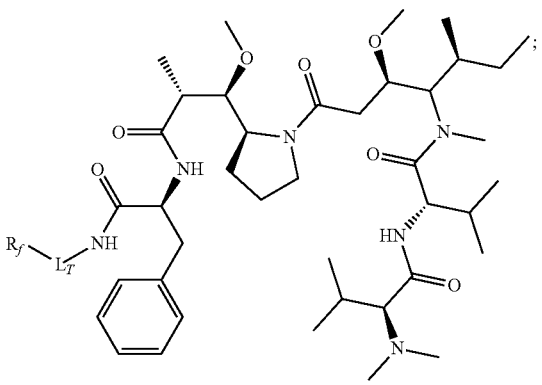

wherein $L_T$ is a linking moiety selected from —$(CH_2)_m$—, —$(OCH_2)_m$—, —$(CH_2O)_m$—, —$(OCH_2CH_2)_m$—, and —$(CH_2CH_2O)_m$—; "m" is an integer from 0 to 6; and $R_f$ is selected from hydrogen, —$NH_2$, —C(O)—$NH_2$, —$[C(R_c)(R_d)]_p$—$NH_2$, —C(O)—$[C(R_c)(R_d)]_p$—$NH_2$, wherein $L_T$ is a linking moiety selected from —$(CH_2)_m$—, —$(OCH_2)_m$—, —$(CH_2O)_m$—, —$(OCH_2CH_2)_m$—, and —$(CH_2CH_2O)_m$—; where "m" is an integer from 0 (i.e. $L_T$ is a bond) to 6; and $R_f$ is selected from hydrogen, —$NH_2$, —$[C(R_c)(R_d)]_p$—$NH_2$,

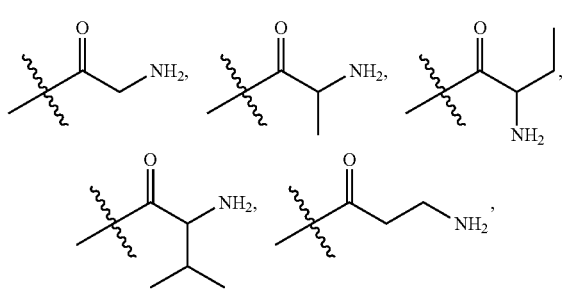

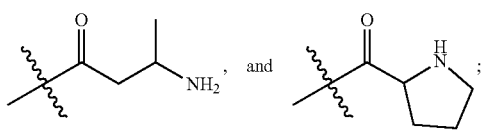

where "p" is an integer from 1-4.

7. The compound of claim 6, wherein $R_f$ comprises the point of attachment of said camptothecin derivative to said compound.

8. The compound of claim 6, wherein $R_f$ is hydrogen or

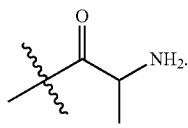 [SMILES: *C(=O)C(C)N]

9. The compound of claim 1, wherein the targeting moiety, A, is an antibody or a synthetically functionalized antibody specific for an antigen over expressed in cancer cells.

10. The compound of claim 9, wherein the targeting moiety, A, is an antibody or synthetically functionalized antibody specific for an antigen selected from the group consisting of HER-2, EGFR, GPNMB, CD56, TACSTD2 (TROP2), CEACAM5, folate receptor-a, mesothelin, ENPP3, guanylyl cyclase C, SLC44A4, NaPi2b, CD70, mucin 1, STEAP1, nectin 4, 5T4, SLTRK6, SC-16, LIV-1, P-Cadherin, PSMA, Fibronectin Extra-domain B, Endothelin receptor ETB, Tenascin c, Collagen IV, VEGFR2, Periostin, CD30, CD79b, CD19, CD22, CD138, CD37, CD33, CD74, CD19 and CD98.

11. The compound of claim 9, wherein the targeting moiety A is trastuzumab or a synthetically functionalized trastuzumab.

12. The compound of claim 1, wherein $L_2$ is absent.

13. The compound of claim 1, wherein $L_1$ is alkylene.

14. The compound of claim 13, wherein $L_1$ is methylene or ethylene.

15. The compound of claim 1, wherein monomer unit (b) has the structure:

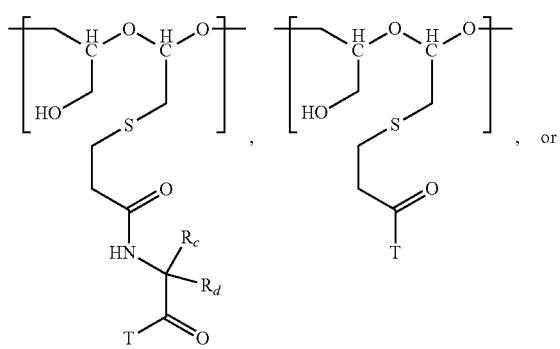

16. The compound of claim 15, wherein monomer unit (b) has the structure:

17. The compound of claim 1, wherein $C_{4A}$ is

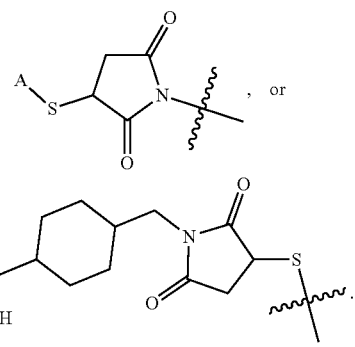

18. The compound of claim 1, wherein $L_4$ has the structure:

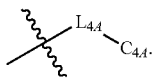

19. The compound of claim 1, wherein $L_{4A}$ is alkylene or heteroalkylene.

20. The compound of claim 1, wherein the mole ratio of T:A in said compound is greater than about 5:1.

21. The compound of claim 1, wherein the compound of Formula (I) is selected from the group consisting of compound 16, compound 17, compound 25, and compound 30:

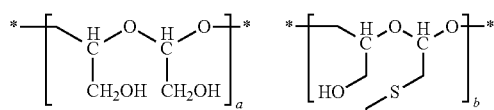 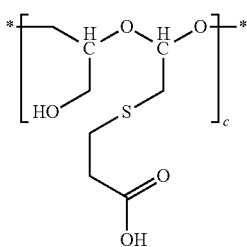
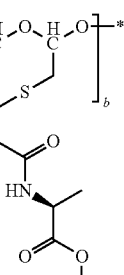
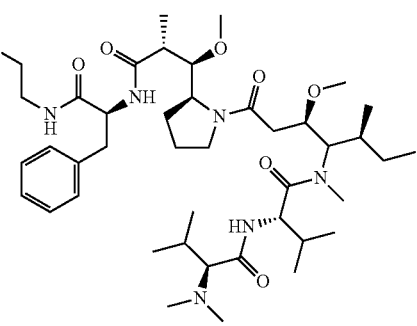
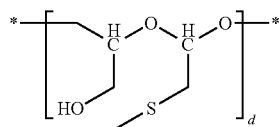
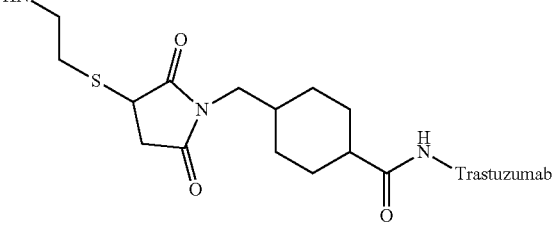
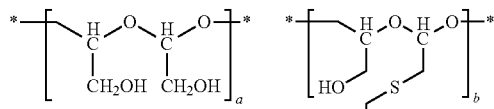 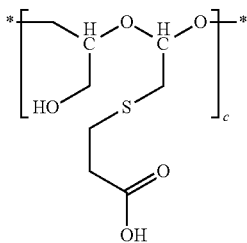
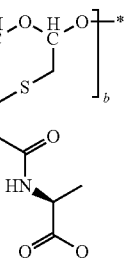
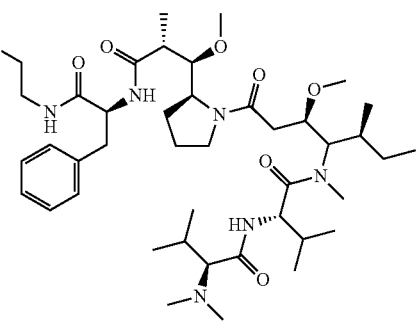

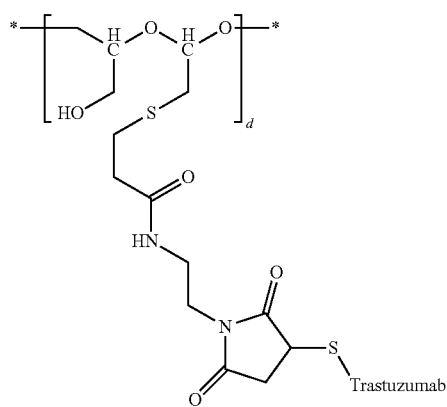
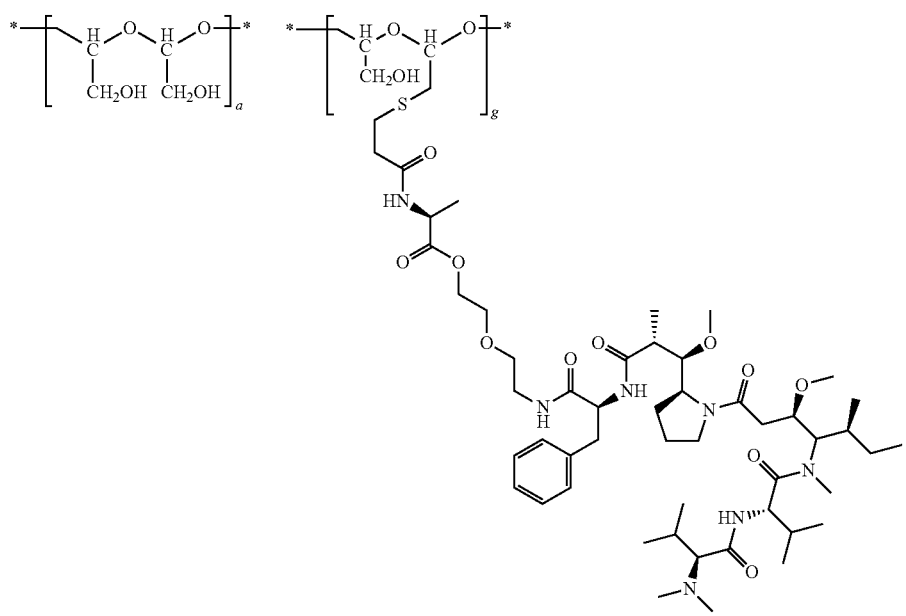
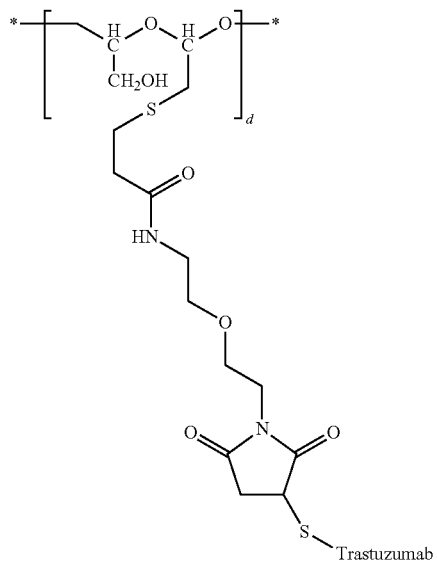

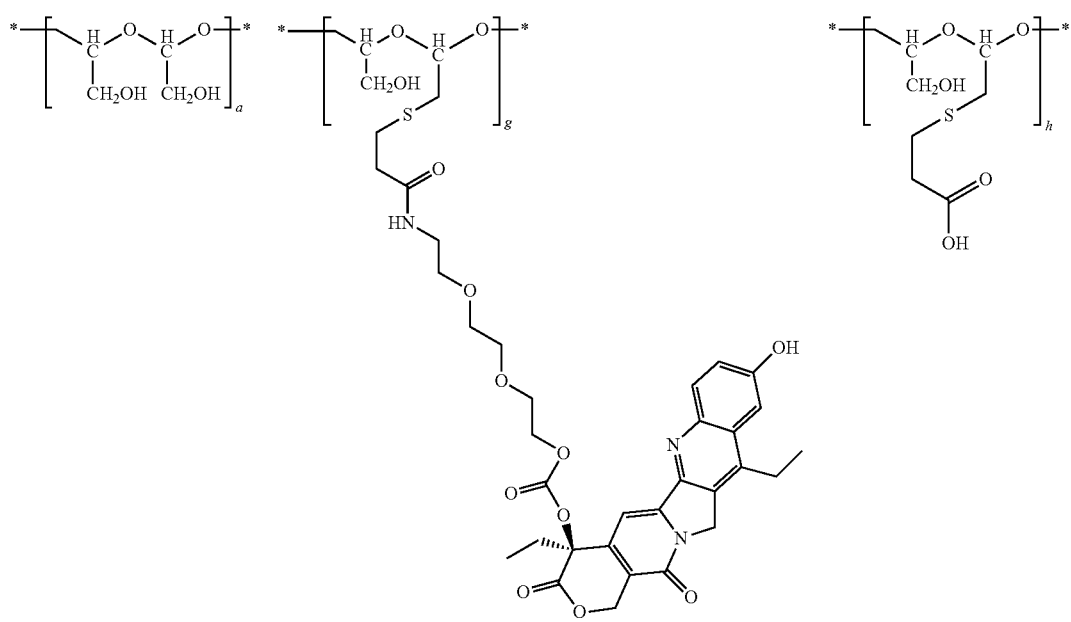
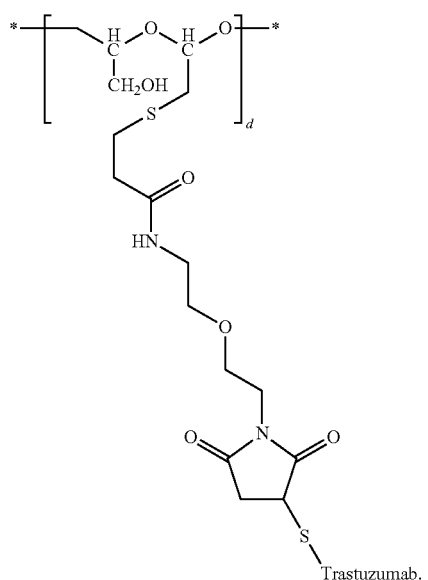
22. A compound of Formula (II) comprising blocks of polymerized monomers (a), (b), and (e):
(II)
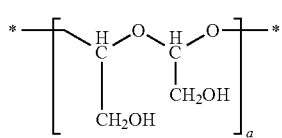
(a)
-continued
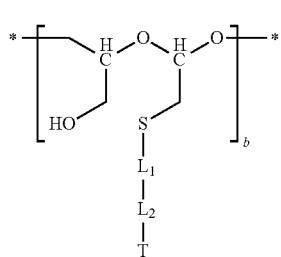
(b)

101
-continued

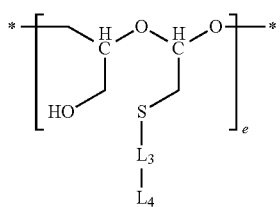
(e)

$L_1$ is a linking group selected from alkylene, heteroalkylene, cycloalkylene, heterocyclylene, arylene, heteroarylene, amidoalkylene, amidoheteroalkylene, and any combination thereof;

$L_2$ is absent, or can be of the formula:

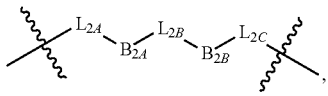

$L_{2A}$ is a linking group selected from alkylene, heteroalkylene, cycloalkylene, heterocyclylene, arylene, heteroarylene, —C(O)—, —N($R_C$)—, and any combination thereof;

$L_{2B}$ and $L_{2C}$ are independently absent or a linker group selected from alkylene, heteroalkylene, cycloalkylene, heterocyclylene, arylene, heteroarylene, amidoalkylene, amidoheteroalkylene, —C(O)—, —N($R_C$)—, and any combination thereof;

$B_{2A}$ and $B_{2B}$ are independently absent or a cleavable linker;

T is a therapeutic agent selected from the group consisting of chemotherapeutic agents, microtubule inhibitors, DNA-damaging agents and RNA transcription inhibitors;

$L_3$ is a linker group selected from alkylene, heteroalkylene, cycloalkylene, heterocyclylene, arylene, heteroarylene, amidoalkylene, amidoheteroalkylene, and any combination thereof;

$L_4$ is a group of the formula:

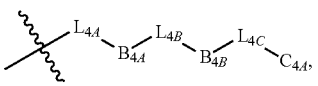

$L_{4A}$ is a linker group selected from alkylene, heteroalkylene, cycloalkylene, heterocyclylene, arylene, heteroarylene, and any combination thereof;

$L_{4B}$ and $L_{4C}$ are independently absent or a linker group selected from selected from alkylene, heteroalkylene, cycloalkylene, heterocyclylene, arylene, heteroarylene, amidoalkylene, amidoheteroalkylene, —C(O)—, —N($R_C$)—, and any combination thereof;

$B_{4A}$ and $B_{4B}$ are independently absent or a cleavable linker

102

$C_{4A}$ is a group selected from

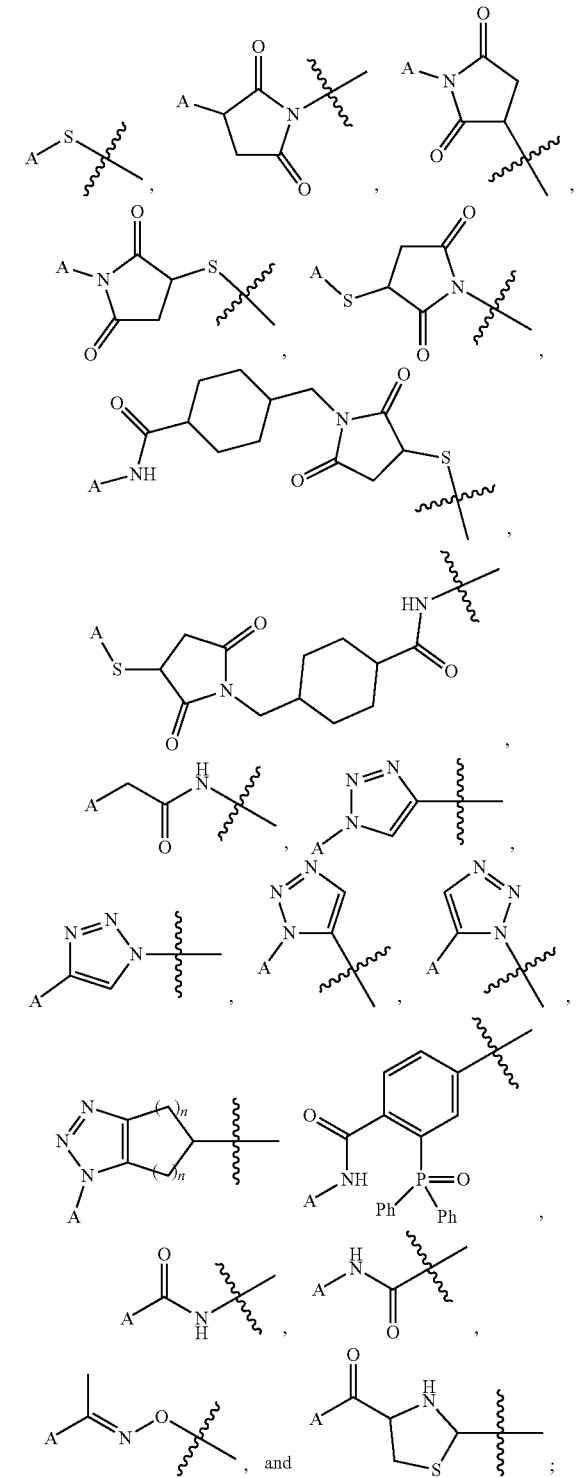

A is —H or a targeting moiety selected from the group consisting of an antibody, a synthetically functionalized antibody, a peptide and a targeting ligand;

"n" is independently at each occurrence an integer ranging from 0-5;

$R_c$ and $R_d$ are independently selected at each occurrence from hydrogen, alkyl, heteroalkyl, cycloalkyl, and heterocyclyl;

each cleavable linker $B_{2A}$, $B_{2B}$, $B_{4A}$ and $B_{4B}$, if present, is independently selected from —S—S—, —C(=O)O—, —OC(=O)—, —C(=O)NR$_c$—, —N(R$_c$)C(=O)—, —OC(=O)O—, —NR$_c$C(=O)O—, —OC(=O)N(R$_c$)— or —N(R$_c$)C(=O)N(R$_d$)—, —C(=O)N(R$_c$)C(=O)—, —C(=O)S—, —SC(=O)—, —SC(=O)S—, —OC(=O)S—, —SC(=O)O—, —SC(=S)O—, —SC(=S)S—, —N(R$_c$)SO$_2$—, —SO$_2$N(R$_c$)—, —N(R$_c$)SO$_2$N(R$_d$)—, —C(=O)N(R$_c$)N(R$_d$)—, —N(R$_c$)N(R$_d$)C(=O)—, —N(R$_c$)N(R$_d$)C(=O)O—, —OC(=O)N(R$_c$)N(R$_d$)—, —C(R$_c$)=N—NH—C(=O)—, —C(=O)NH—N=C(R$_c$)—, —C(R$_c$)=N—O—, —O—N=C(R$_c$)—,

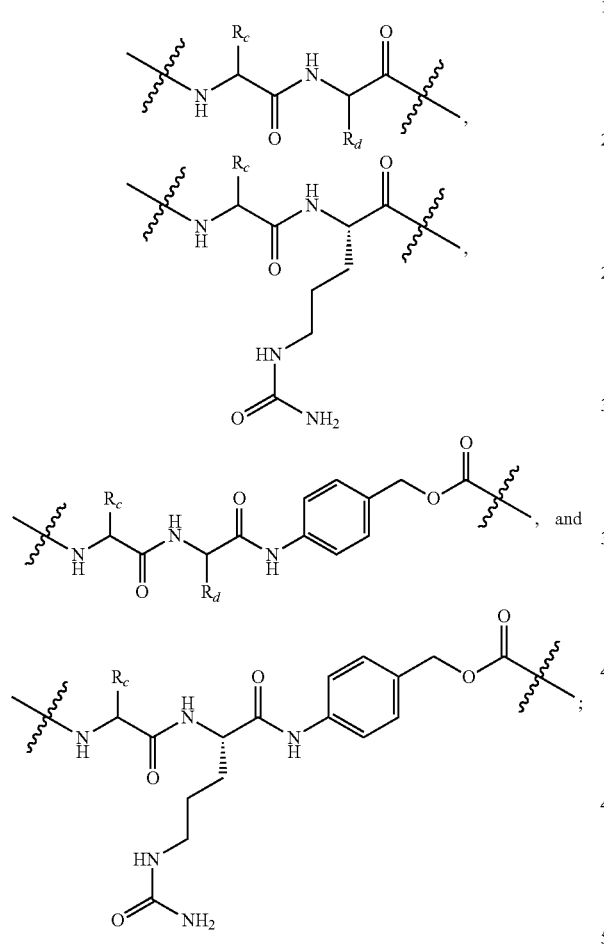

, and

;

where each monomer is substituted independently from any additional monomer;

"a" is independently at each occurrence an integer from 1-1860;

"b" is independently at each occurrence an integer from 1-372;

"e" is independently at each occurrence an integer from 1-186; and each block of monomer unit (a), (b), and (e), is covalently attached to at least one block monomer unit (a), (b), and/or (e); and each block of monomer units is independently substituted from any other block of monomer units; with the proviso that the compound of Formula (II) contains one or more therapeutic agent and one or more targeting moiety.

23. The compound of claim 22, wherein said therapeutic agent, T, is a chemotherapeutic agent.

24. The compound of claim 22, wherein the therapeutic agent is an auristatin derivative of structure:

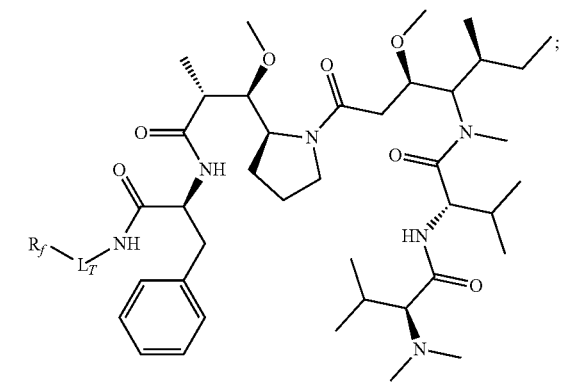

wherein $L_T$ is a linking moiety selected from —(CH$_2$)$_m$—, —(OCH$_2$)$_m$—, —(OCH$_2$CH$_2$)$_m$—, and —(CH$_2$CH$_2$O)$_m$—, "m" is an integer from 0 (i.e. $L_T$ is a bond) to 6; and $R_f$ is selected from hydrogen, —NH$_2$, —C(O)—NH$_2$, —[C(R$_c$)(R$_d$)]$_p$—NH$_2$, —C(O)—[C(R$_c$)(R$_d$)]$_p$—NH$_2$,

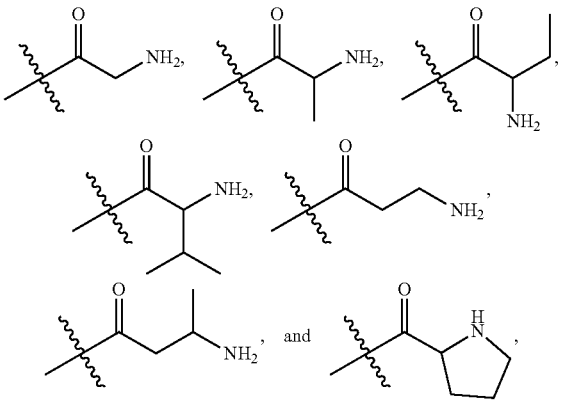

and "p" is an integer from 1-4.

25. The compound of claim 24, wherein $R_f$ comprises the point of attachment of said auristatin derivative to said compound.

26. The compound of claim 22, wherein said therapeutic agent is a camptothecin derivative having the structure:

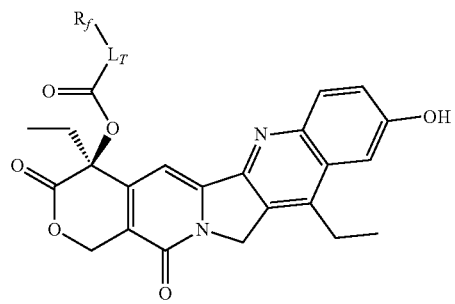

wherein $L_T$ is a linking moiety selected from —$(CH_2)_m$—, —$(OCH_2)_m$—, —$(CH_2O)_m$—, —$(OCH_2CH_2)_m$—, and —$(CH_2CH_2O)_m$—; where "m" is an integer from 0 to 6; and
$R_f$ is selected from hydrogen, —$NH_2$, —$[C(R_c)(R_d)]_p$—$NH_2$,
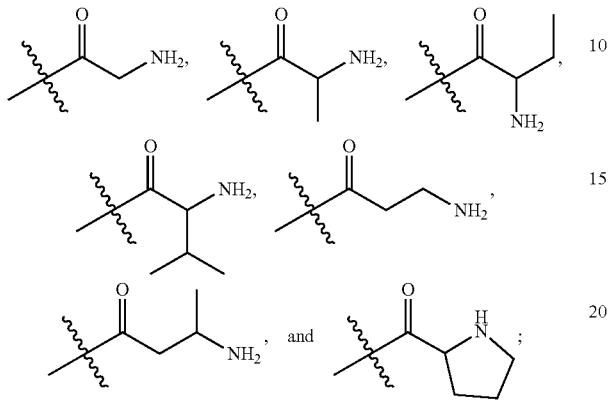
where "p" is an integer from 1-4.
27. The compound of claim 26, wherein $R_f$ comprises the point of attachment of said camptothecin derivative to said compound.
* * * * *